United States Patent
Sliwa, Jr. et al.

(10) Patent No.: US 8,057,465 B2
(45) Date of Patent: *Nov. 15, 2011

(54) METHODS AND DEVICES FOR ABLATION

(75) Inventors: John W. Sliwa, Jr., Los Altos, CA (US); Matthias Vaska, Palo Alto, CA (US); Jonathan L. Podmore, San Carlos, CA (US); Roxanne L. Richman, Los Gatos, CA (US); Scott C. Anderson, Sunnyvale, CA (US); Gerard Champsaur, Palo Alto, CA (US); John E. Crowe, Menlo Park, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1246 days.

This patent is subject to a terminal disclaimer.

(21) Appl. No.: 11/785,159

(22) Filed: Apr. 16, 2007

(65) Prior Publication Data

US 2007/0255276 A1 Nov. 1, 2007

Related U.S. Application Data

(63) Continuation of application No. 11/237,619, filed on Sep. 27, 2005, which is a continuation of application No. 10/006,088, filed on Dec. 5, 2001, now abandoned, which is a continuation of application No. 09/884,435, filed on Jun. 19, 2001, now Pat. No. 6,719,755, which is a continuation-in-part of application No. 09/614,991, filed on Jul. 12, 2000, now Pat. No. 6,805,128, which is a continuation-in-part of application No. 09/507,336, filed on Feb. 18, 2000, now abandoned, which is a continuation-in-part of application No. 09/356,476, filed on Jul. 19, 1999, now Pat. No. 6,311,692, which is a continuation-in-part of application No. 09/157,824, filed on Sep. 21, 1998, now Pat. No. 6,237,605, which is a continuation-in-part of application No. 08/943,683, filed on Oct. 15, 1997, now Pat. No. 6,161,543, which is a continuation-in-part of application No. 08/735,036, filed on Oct. 22, 1996, now abandoned.

(51) Int. Cl.
*A61B 18/18* (2006.01)
(52) U.S. Cl. .............................. 606/27; 606/34; 600/439
(58) Field of Classification Search .................... 606/27, 606/28, 32–34, 41; 601/2, 3; 600/439, 459, 600/461, 462; 607/101, 102
See application file for complete search history.

(56) References Cited

U.S. PATENT DOCUMENTS 984,756 A 2/1911 Frisch
(Continued)

FOREIGN PATENT DOCUMENTS

AU A-70522/96 11/1994
(Continued)

OTHER PUBLICATIONS

AFx, inc., "FLEX Surgical Ablation Device: Instructions for Use," Document No. 900044 Rev A; Mar. 28, 2000: 1-9.
(Continued)

*Primary Examiner* — Michael Peffley
(74) *Attorney, Agent, or Firm* — Wiley Rein LLP

(57) ABSTRACT

An ablating device has a cover which holds an interface material such as a gel. The cover contains the interface material during initial placement of the device. The ablating device may also have a removable tip or a membrane filled with fluid. In still another aspect, the ablating device may be submerged in liquid during operation.

22 Claims, 64 Drawing Sheets

U.S. PATENT DOCUMENTS

| | | |
|---|---|---|
| 3,369,550 A | 2/1968 | Armao et al. |
| 3,862,627 A | 1/1975 | Hans, Sr. |
| 4,022,215 A | 5/1977 | Benson |
| 4,072,152 A | 2/1978 | Linehan |
| 4,207,874 A | 6/1980 | Choy |
| 4,353,371 A | 10/1982 | Cosman |
| 4,375,818 A | 3/1983 | Suwaki et al. |
| 4,655,216 A | 4/1987 | Tischer |
| 4,736,749 A | 4/1988 | Lundback |
| 4,786,155 A | 11/1988 | Fantone et al. |
| 4,802,475 A | 2/1989 | Weshahy |
| 4,815,470 A | 3/1989 | Curtis et al. |
| 4,872,346 A | 10/1989 | Kelly-Fry et al. |
| 4,889,137 A | 12/1989 | Kolobow |
| 4,917,095 A | 4/1990 | Fry et al. |
| 4,936,281 A | 6/1990 | Stasz |
| 4,985,030 A | 1/1991 | Melzer et al. |
| 5,013,312 A | 5/1991 | Parins et al. |
| 5,080,102 A | 1/1992 | Dory |
| 5,108,390 A | 4/1992 | Potocky et al. |
| 5,109,830 A | 5/1992 | Cho |
| 5,147,355 A | 9/1992 | Friedman et al. |
| 5,190,541 A | 3/1993 | Abele et al. |
| 5,197,964 A | 3/1993 | Parins |
| 5,222,501 A | 6/1993 | Ideker et al. |
| 5,224,943 A | 7/1993 | Goddard |
| 5,231,995 A | 8/1993 | Desai |
| 5,254,116 A | 10/1993 | Baust et al. |
| 5,263,493 A | 11/1993 | Avitall |
| 5,269,291 A | 12/1993 | Carter |
| 5,277,201 A | 1/1994 | Stern |
| 5,281,215 A | 1/1994 | Milder |
| 5,290,286 A | 3/1994 | Parins |
| 5,295,484 A | 3/1994 | Marcus et al. |
| 5,323,781 A | 6/1994 | Ideker et al. |
| 5,324,255 A | 6/1994 | Passafaro et al. |
| 5,324,284 A | 6/1994 | Imran |
| 5,334,181 A | 8/1994 | Rubinsky et al. |
| 5,341,807 A | 8/1994 | Nardella |
| 5,348,554 A | 9/1994 | Imran et al. |
| 5,353,783 A | 10/1994 | Nakao et al. |
| 5,354,258 A | 10/1994 | Dory |
| 5,366,443 A | 11/1994 | Eggers et al. |
| 5,370,675 A | 12/1994 | Edwards et al. |
| 5,385,148 A | 1/1995 | Lesh et al. |
| 5,396,887 A | 3/1995 | Imran |
| 5,400,783 A | 3/1995 | Pomeranz et al. |
| 5,405,376 A | 4/1995 | Mulier et al. |
| 5,406,946 A | 4/1995 | Imran |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,437,664 A | 8/1995 | Cohen et al. |
| 5,443,463 A | 8/1995 | Stern et al. |
| 5,443,470 A | 8/1995 | Stern et al. |
| 5,450,843 A | 9/1995 | Moll et al. |
| 5,452,733 A | 9/1995 | Sterman et al. |
| 5,462,521 A | 10/1995 | Brucker et al. |
| 5,462,545 A | 10/1995 | Wang et al. |
| 5,465,717 A | 11/1995 | Imran et al. |
| 5,469,853 A | 11/1995 | Law et al. |
| 5,478,330 A | 12/1995 | Imran et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,500,012 A | 3/1996 | Brucker et al. |
| 5,501,698 A | 3/1996 | Roth et al. |
| 5,505,730 A | 4/1996 | Edwards |
| 5,520,682 A | 5/1996 | Baust et al. |
| 5,536,267 A | 7/1996 | Edwards et al. |
| 5,540,679 A | 7/1996 | Fram et al. |
| 5,540,681 A | 7/1996 | Strul et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,644 A | 9/1996 | Boyd et al. |
| 5,560,362 A | 10/1996 | Sliwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,584,803 A | 12/1996 | Stevens et al. |
| 5,588,432 A | 12/1996 | Crowley |
| 5,590,657 A | 1/1997 | Cain et al. |
| 5,595,183 A | 1/1997 | Swanson et al. |
| 5,607,462 A | 3/1997 | Imran |
| 5,617,854 A | 4/1997 | Munsif |
| 5,626,607 A | 5/1997 | Malecki et al. |
| 5,630,837 A | 5/1997 | Crowley |
| 5,637,090 A | 6/1997 | McGee et al. |
| 5,643,197 A | 7/1997 | Brucker et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | LaFontaine |
| 5,678,550 A | 10/1997 | Bassen et al. |
| 5,680,860 A | 10/1997 | Imran |
| 5,681,278 A | 10/1997 | Igo et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,925 A | 12/1997 | Taylor |
| 5,697,927 A | 12/1997 | Imran et al. |
| 5,697,928 A | 12/1997 | Walcott et al. |
| 5,697,949 A | 12/1997 | Giurtino et al. |
| 5,713,942 A | 2/1998 | Stern |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Larnard |
| 5,722,402 A | 3/1998 | Swanson et al. |
| 5,728,094 A | 3/1998 | Edwards |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,735,290 A | 4/1998 | Sterman et al. |
| 5,746,224 A | 5/1998 | Edwards |
| 5,755,760 A | 5/1998 | Maguire et al. |
| 5,782,828 A | 7/1998 | Chen et al. |
| 5,782,899 A | 7/1998 | Imran |
| 5,785,706 A | 7/1998 | Bednarek |
| 5,788,636 A | 8/1998 | Curley |
| 5,797,960 A | 8/1998 | Stevens et al. |
| 5,800,428 A | 9/1998 | Nelson et al. |
| 5,800,482 A | 9/1998 | Pomeranz et al. |
| 5,810,721 A | 9/1998 | Mueller et al. |
| 5,810,802 A | 9/1998 | Panescu et al. |
| 5,817,021 A | 10/1998 | Reichenberger |
| 5,827,216 A | 10/1998 | Igo et al. |
| 5,827,281 A | 10/1998 | Levin |
| 5,830,214 A | 11/1998 | Flom et al. |
| 5,836,947 A | 11/1998 | Fleischman et al. |
| 5,840,030 A | 11/1998 | Ferek-Petric et al. |
| 5,844,349 A | 12/1998 | Oakley et al. |
| 5,849,028 A | 12/1998 | Chen |
| 5,863,291 A | 1/1999 | Schaer |
| 5,871,523 A | 2/1999 | Fleischman et al. |
| 5,871,525 A | 2/1999 | Edwards et al. |
| 5,873,845 A | 2/1999 | Cline et al. |

| | | |
|---|---|---|
| 5,876,399 A | 3/1999 | Chia et al. |
| 5,879,295 A | 3/1999 | Li et al. |
| 5,879,296 A | 3/1999 | Ockuly et al. |
| 5,882,346 A | 3/1999 | Pomeranz et al. |
| 5,885,278 A | 3/1999 | Fleischman |
| 5,891,134 A | 4/1999 | Gobe et al. |
| 5,893,848 A | 4/1999 | Negus et al. |
| 5,895,417 A | 4/1999 | Pomeranz et al. |
| 5,897,554 A | 4/1999 | Chia et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,954,661 A | 9/1999 | Greenspon et al. |
| 5,971,980 A | 10/1999 | Sherman |
| 5,971,983 A | 10/1999 | Lesh |
| 5,993,447 A | 11/1999 | Blewett et al. |
| 6,007,499 A | 12/1999 | Martin et al. |
| 6,012,457 A | 1/2000 | Lesh |
| 6,016,811 A | 1/2000 | Knopp et al. |
| 6,023,638 A | 2/2000 | Swanson |
| 6,042,556 A | 3/2000 | Beach et al. |
| 6,068,629 A | 5/2000 | Haissaguerre et al. |
| 6,071,274 A | 6/2000 | Thompson et al. |
| 6,071,279 A | 6/2000 | Whayne et al. |
| 6,071,282 A | 6/2000 | Fleischman |
| 6,088,894 A | 7/2000 | Oakley |
| 6,113,592 A | 9/2000 | Taylor |
| 6,117,101 A | 9/2000 | Diederich et al. |
| 6,120,496 A | 9/2000 | Whayne et al. |
| 6,139,563 A | 10/2000 | Cosgrove et al. |
| 6,142,993 A | 11/2000 | Whayne et al. |
| 6,142,994 A | 11/2000 | Swanson et al. |
| 6,146,379 A | 11/2000 | Fleischman et al. |
| 6,152,920 A | 11/2000 | Thompson et al. |
| 6,161,543 A | 12/2000 | Cox et al. |
| 6,164,283 A | 12/2000 | Lesh |
| 6,206,831 B1 | 3/2001 | Suorsa et al. |
| 6,212,426 B1 | 4/2001 | Swanson |
| 6,214,754 B1 | 4/2001 | Stein |
| 6,217,528 B1 | 4/2001 | Koblish et al. |
| 6,217,576 B1 | 4/2001 | Tu et al. |
| 6,231,518 B1 | 5/2001 | Grabek et al. |
| 6,235,024 B1 | 5/2001 | Tu |
| 6,237,605 B1 | 5/2001 | Vaska et al. |
| 6,238,347 B1 | 5/2001 | Nix et al. |
| 6,241,722 B1 | 6/2001 | Dobak et al. |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,128 B1 | 6/2001 | Knopp et al. |
| 6,270,471 B1 | 8/2001 | Hechel et al. |
| 6,293,943 B1 | 9/2001 | Panescu et al. |
| 6,296,619 B1 | 10/2001 | Brisken et al. |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,325,797 B1 | 12/2001 | Stewart et al. |
| 6,325,798 B1 | 12/2001 | Edwards et al. |
| 6,332,881 B1 | 12/2001 | Carner et al. |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,720 B1 | 6/2002 | Hissong et al. |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,447,507 B1 | 9/2002 | Bednarek et al. |
| 6,454,758 B1 | 9/2002 | Thompson et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,477,396 B1 | 11/2002 | Mest et al. |
| 6,484,727 B1 | 11/2002 | Vaska et al. |
| 6,514,249 B1 | 2/2003 | Maguire et al. |
| 6,517,536 B2 | 2/2003 | Hooven et al. |
| 6,527,767 B2 | 3/2003 | Wang et al. |
| 6,544,262 B2 | 4/2003 | Fleischman |
| 6,546,934 B1 | 4/2003 | Ingle et al. |
| 6,582,423 B1 | 6/2003 | Thapliyal et al. |
| 6,599,288 B2 | 7/2003 | Maguire et al. |
| 6,605,084 B2 | 8/2003 | Acker et al. |
| 6,610,055 B1 | 8/2003 | Swanson et al. |
| 6,641,579 B1 * | 11/2003 | Bernardi et al. ............. 606/27 |
| 6,645,199 B1 | 11/2003 | Jenkins et al. |
| 6,645,202 B1 | 11/2003 | Pless et al. |
| 6,689,128 B2 | 2/2004 | Sliwa, Jr. et al. |
| 6,692,450 B1 | 2/2004 | Coleman |
| 6,701,931 B2 | 3/2004 | Sliwa, Jr. et al. |
| 6,740,080 B2 | 5/2004 | Jain et al. |
| 6,745,080 B2 | 6/2004 | Koblish |
| 6,771,996 B2 | 8/2004 | Bowe et al. |
| 6,805,128 B1 | 10/2004 | Pless et al. |
| 6,805,129 B1 | 10/2004 | Pless et al. |
| 6,840,936 B2 | 1/2005 | Sliwa et al. |
| 6,858,026 B2 | 2/2005 | Sliwa et al. |
| 6,942,661 B2 | 9/2005 | Swanson |
| 6,942,662 B2 | 9/2005 | Goble et al. |
| 7,213,601 B2 | 5/2007 | Stevens et al. |
| 7,338,486 B2 | 3/2008 | Sliwa et al. |
| 7,387,126 B2 | 6/2008 | Cox et al. |
| 2002/0019627 A1 | 2/2002 | Maguire et al. |
| 2002/0022839 A1 | 2/2002 | Stewart et al. |
| 2002/0026183 A1 | 2/2002 | Simpson |
| 2002/0042610 A1 | 4/2002 | Sliwa et al. |
| 2002/0062124 A1 | 5/2002 | Keane |
| 2002/0087151 A1 | 7/2002 | Mody et al. |
| 2002/0087208 A1 | 7/2002 | Koblish et al. |
| 2002/0111567 A1 | 8/2002 | Vanden Hoek et al. |
| 2002/0128639 A1 | 9/2002 | Pless et al. |
| 2002/0143326 A1 | 10/2002 | Foley et al. |
| 2007/0293855 A1 | 12/2007 | Sliwa et al. |
| 2007/0299496 A1 | 12/2007 | Podmore et al. |
| 2008/0045946 A1 | 2/2008 | Vaska |
| 2009/0192603 A1 | 7/2009 | Ryan |

FOREIGN PATENT DOCUMENTS

| | | |
|---|---|---|
| EP | 1181896 A1 | 2/2002 |
| GB | 2 094 636 | 9/1982 |
| GB | 2 289 510 A | 11/1995 |
| WO | WO 95/10318 | 4/1995 |
| WO | WO 95/10319 | 4/1995 |
| WO | WO 95/10321 | 4/1995 |
| WO | WO 95/10978 | 4/1995 |
| WO | WO 95/15115 | 6/1995 |
| WO | WO 95/17222 | 6/1995 |
| WO | WO 95/30380 A | 11/1995 |
| WO | WO 96/10961 | 4/1996 |
| WO | WO 96/26675 | 9/1996 |
| WO | WO 96/39966 | 12/1996 |
| WO | WO 97/06727 | 2/1997 |
| WO | WO 97/17904 | 5/1997 |
| WO | WO 97/18853 | 5/1997 |
| WO | WO 97/25916 | 7/1997 |
| WO | WO 97/25918 | 7/1997 |
| WO | WO 97/25919 | 7/1997 |
| WO | WO-97/29699 | 8/1997 |
| WO | WO 97/32525 | 9/1997 |
| WO | WO 97/33526 | 9/1997 |
| WO | WO 97/37607 | 10/1997 |

| WO | WO-97/38748 | 10/1997 |
| WO | WO 97/41793 | 11/1997 |
| WO | WO 97/43970 | 11/1997 |
| WO | WO 97/45156 | 12/1997 |
| WO | WO 98/17187 | 4/1998 |
| WO | WO 98/24488 | 6/1998 |
| WO | WO 98/26724 | 6/1998 |
| WO | WO 98/37822 | 9/1998 |
| WO | WO 98/48881 | 11/1998 |
| WO | WO 98/49957 | 11/1998 |
| WO | WO 99/02096 | 1/1999 |
| WO | WO-99/02096 | 1/1999 |
| WO | WO 99/04696 | 2/1999 |
| WO | WO 99/48421 A1 | 9/1999 |
| WO | WO 99/49788 | 10/1999 |
| WO | WO 99/56812 | 11/1999 |
| WO | WO 99/59486 | 11/1999 |
| WO | WO 00/45706 | 8/2000 |
| WO | WO 00/57495 | 9/2000 |
| WO | WO 01/03594 A1 | 1/2001 |
| WO | WO 01/05305 A1 | 1/2001 |
| WO | WO-01/05306 | 1/2001 |
| WO | WO 01/28623 A2 | 4/2001 |
| WO | WO 01/45550 A2 | 6/2001 |
| WO | WO 01/66189 A1 | 9/2001 |
| WO | WO 01/70112 A1 | 9/2001 |
| WO | WO 01/72234 A1 | 10/2001 |
| WO | WO 01/72373 A2 | 10/2001 |
| WO | WO-01/80708 | 11/2001 |
| WO | WO 01/82778 A2 | 11/2001 |
| WO | WO 02/05720 A1 | 1/2002 |
| WO | WO 02/05722 A1 | 1/2002 |
| WO | WO 02/05868 A2 | 1/2002 |
| WO | WO 02/30310 A1 | 1/2002 |
| WO | WO 02/09610 A1 | 2/2002 |
| WO | WO 02/21995 A2 | 3/2002 |
| WO | WO 02/24050 | 3/2002 |
| WO | WO 02/26142 A1 | 4/2002 |
| WO | WO 02/40093 | 5/2002 |
| WO | WO 02/45608 A2 | 6/2002 |
| WO | WO 02/077774 A2 | 10/2002 |
| WO | WO-02/102231 | 12/2002 |

OTHER PUBLICATIONS

AFx, inc., "AFx Microwave Generator, Series 1000; User's Manual," Document No. 900067/A/1310, (2000): 1-13.

AFx, inc., "FLEX10™: Accessory for the Afx Microwave Ablation Aystem; Instructions for Use," Document No. 900077/C/1638, (2001): 1-8. Supplemental Document No. 900106/A/1586.

Boston Scientific, EP Technologies, "Cobra® Electrosurgical Unit, Operator's Manual: 4810 & 4811," Document No. 11292-001 EAW Ver AC, Feb. 2000; pp. 1-1 thru 9-2.

Boston Scientific, EP Technologies, "Cobra® Surgical Probe; Directions for Use," Document No. 13954-001 Rev A, Oct. 2001: p. 3.

Boston Scientific, EP Technologies, "Cobra® RF System: The first surgical system for creating linear lesions." Document No. DEP-225 Rev A, Jan. 2002.

Caccitolo et al., "Open-Heart Endocardial Radiofrequency Ablation: . . . " *J of Surgical Research*, (2001); 97: 27-33.

Chevalier, et al., "Thoracoscopic Epicardial Radiofrequency Ablation for Vagal Atrial Fibrillation in Dogs," *PACE* Jun. 1999; 22 (Part I), 880-886.

Cox et al., "The Surgical Treatment of Atrial Fibrillation, IV Surgical Technique," *J Thorac Cardiovasc Surg*, 1991; 101: 584-592.

Demazumder et al., "Comparison of Irrigated Electrode Designs for Radiofrequency Ablation of Myocardium," *J of Interventional Cardiac Electrophysiology5*, (2001): 391-400.

Elvan et al., "Radiofrequency Catheter Ablation of the Atria Eliminates Pacing-Induced Sustained Atrial Fibrillation and Reduces Connexin in 43 Dogs," *Circulation*, 1997;96(5):1675-1685.

Fieguth et al., "Inhibition of Atrial Fibrillation by Pulmonary Vein Isolation and Auricular Resection—Experimental Study in a Sheep Model," *European Journal of Cardio-Thoracic Surgery*, 1997;11:714-721.

He et al., "Preliminary Results Using Ultrasound Energy for Ablation of the Ventricular Myocardium in Dogs," *Am J Card*, 1994;73:1029-1031.

He et al., "Application of Ultrasound Energy for Intracardiac Ablation of Arrhythmias," *The European Society of Cardiology*, 1995;16:961-966.

Hunt, John W., "Application of Microwave, Ultrasound and Radiofrequency Heating," *Natl Cancer Inst Monogr*, (1982); 61: 447-456.

Hynynen et al., "Cylindrical Ultrasonic Transducers for Cardiac Catheter Ablation," *IEEE Transactions on Biomedical Engineering*, 1997;44(2):144-151.

Inoue et al., "Video Assisted Thoracoscopic and Cardioscopic Radiofrequency Maze Ablation," *ASAIO Journal*, 1997;43:334-337.

Jumrussirikul et al., "Prospective Comparison of Temperature Guided Microwave and Radiofrequency Catheter Ablation in the Swine Heart," *PACE* (1998); 21:1364-1374.

Lee, et al., "High Intensity Focused Ultrasound Effect on Cardiac Tissues: Potential for Clinical Application," *Echocardiography*, (2000) vol. 17, No. 6, Part 1: 563-566.

Liem et al. "Microwave Catheter Ablation Using a Clinical Prototype System with a Lateral Firing Antenna Design," *PACE*, (1998); 21 [pt 1]: 714-721.

McRury, Ian D., Haines, David E., "Ablation for the Treatment of Arrhythmais," *Proceedings of the IEEE*, (1996); vol. 84, No. 3: 404-415.

Mitchell et al., "Morphological and Physiological Characterictics of Discontinuous Linear Atrial Ablations During Atrial Pacing and Atrial Fibrillation," *J Cardiovas Electrophysiol*, (1999); vol. 10: 378-386.

Mittleman et al., "Use of the Saline Electrode Catheter for Improved Energy Delivery and Increased Lesion Size in Radiofrequency Catherter Ablation," *PACE*, (1995); 18[Pt 1]: 1022-1027.

Ohkubo et al., "Experimental Study of Catheter Ablation Using Ultrasound Energy in Canine and Porcine Hearts," *Jpn Heart J*, (1998); 39: 399-409.

Olgin et al., "Electrophysical Effects of Long. Linear Atrial Lesions Placed Under Intracardiac Ultrasound Guidance," *Circulation*, 1997;96(8):2715-2721.

Petersen et al., "Tissue Temperatures and Lesion Size During Irrigated Tip Catheter Radiofrequency Ablation: . . . ," *PACE*, (2000); 23: 8-17.

Pfeiffer et al., "Epicardial Neodymium . . . ," *Am Heart J*, 1996;94(12):3221-3225.

Righetti et al., "Elastographic Characterization of HIFU-Induced Lesions in Canine Livers," *Ultrasound in Med. & Biol.*, (1999), vol. 25 No. 7; 1099-1113.

Sibille et al., "Characterization of Extracorporeal Ablation of Normal and Tumor-Bearing Liver Tissue by High Intensity Focused Ultrasound," *Ultrasound in Med. & Biol.*, (1993); vol. 19, No. 9: 803-813.

Sosa et al., "Radiofrequency Catheter Ablation of Ventricular Tachycardia Guided by Nonsurgical Epicardial Mapping in Chronic Chagasic heart Disease," *PACE*, Jan. 1999; 22 (Part I), 128-130.

Strickberger et al., "Extracardiac Ablation of the Canine Atrioventricular Junction by Use of High-Intensity Focused Ultrasound," *Circulation*, (1999); 100: 203-208.

Thomas et al., "Microwave Ablation of Myocardial Tissue: . . . " *J Cardiovasc Electrophysiol*, (1999); vol. 10: 72-78.

Vanderbrink et al., "Safety and Efficacy of a Steerable Temperature Monitoring Microwave Catheter System for Ventriculat Myocardial Ablation," *J Cardiovasc Electrophysiol*, (2000); vol. 11: 305-310.

Von Oppell et al., "Effectiveness of two radiofrequency ablation systems in atrial tissue," *Euro J of Cardio-thoracic Surg*, (2001); 20: 956-960.

Watanabe et al., "Experimental Application of Microwave Tissue Coagulation to Ventricular Myocardium," *Ann Thorac Surg*, (1999); 67: 666-671.

Weber, "Laser versus Radiofrequency Catheter Ablation of Ventricular Myocardium in Dogs: A Comparative Test," *Cardiology*, 1997: 88:346-352.

Whayne et al., "Microwave Catheter Ablation of Myocardium in Vitro . . . " *Circulation* (1994); 89: 2390-2395.

Williams et al., "Surgical Treatment of Atrial Fibrillation Using Radiofrequency Energy," *Ann Thorac Surg*, (2001); 71: 1939-1944.

Wonnell et al., "Evaluation of Microwave and Radio Frequency Catheter Ablation in a Myocardium-Equivalent Phantom Model," *IEEE Transactions on Biomedical Engineering*, 1992;39(10):1086-1095.

Zimmer et al., "The Feasibility of Using Ultrasound for Cardiac Ablation," *IEEE Transactions on Biomedical Engineering*, 1995;42(9):891-897.

Avitall et al., "A Thoracoscopic Approach to Ablate Atrial Fibrillation Via Linear Radiofrequency Lesion Generation on the Epicardium of Both Atria," PACE, Apr. 1996;19(Part 11):626,#241.

Jais et al., "Catheter Ablation for Paroxysmal Atrial Fibrillation: High Success Rates with Ablation in the Left Atrium," Circulation (Nov. 1996) 94:1-675,#3946.

Lee et al., "Minimally Invasive Epicardial Atrial Linear Ablation Using Cooled Radiofrequency Energy," Circulation (Nov. 1997) 96:577,I-576,#3221.

Lindsay et al., "Intraoperative Observations and Epicardial Mapping after Attempted Catheter Ablation of Atrial Fibrillation," Circulation (Nov. 1997) 96:450,#2517.

Nakagawa et al, "Use of Atrial Potential Attenuation to Identify Endpoint of Radiofrequency Application for Continuous, Transmural Linear Atrial Ablation," Circulation (Nov. 1997) 96:577,I-451,#2523.

Sharma et al., "A Comparison of Sequential with Simultaneous Delivery of RF Energy Application at Multiple Electrodes to Produce Linear Continuous Lesions," Circulation (Nov. 1997) 96:576,I-576,#3220.

Sie et al., "Radiofrequency Ablation of Atrial Fibrillation in Patients Undergoing Valve Surgery," Circulation (Nov. 1997) 84:I450,#2519.

Sie et al., "Radiofrequency Ablation of Atrial Fibrillation in Patients Undergoing Mitral Valve Surgery. First Experience," Circulation (Nov. 1996) 96:450,I-675,#3946.

Cox et al., The Surgical Treatment of Atrial Fibrillation. I. Summary of the Current Concepts of the Mechanisms of Atrial Flutter and Atrial Fibrillation, J. Thorac. Cardiovasc. Surgery, vol. 101, 402-05 (Mar. 1991). Published by the American Association for Thoracic Surgery and the Western Thoracic Surgical Association in Beverly, MA.

Cox et al., The Surgical Treatment of Atrial Fibrillation. II. Intraoperative Electrophysiologic Mapping and Description of the Electrophysiologic Basis of Atrial Flutter and Atrial Fibrillation, J. Thorac. Cardiovasc. Surgery, vol. 101, 406-26 (Mar. 1991). Published by the American Association for Thoracic Surgery and the Western Thoracic Surgical Association in Beverly, MA.

Cox et al., The Surgical Treatment of Atrial Fibrillation. III. Development of a Definitive Surgical Procedure, J. Thorac. Cardiovasc. Surgery, vol. 101, 569-83 (Apr. 1991). Published by the American Association for Thoracic Surgery and The Western Thoracic Surgical Association in Beverly, MA.

* cited by examiner

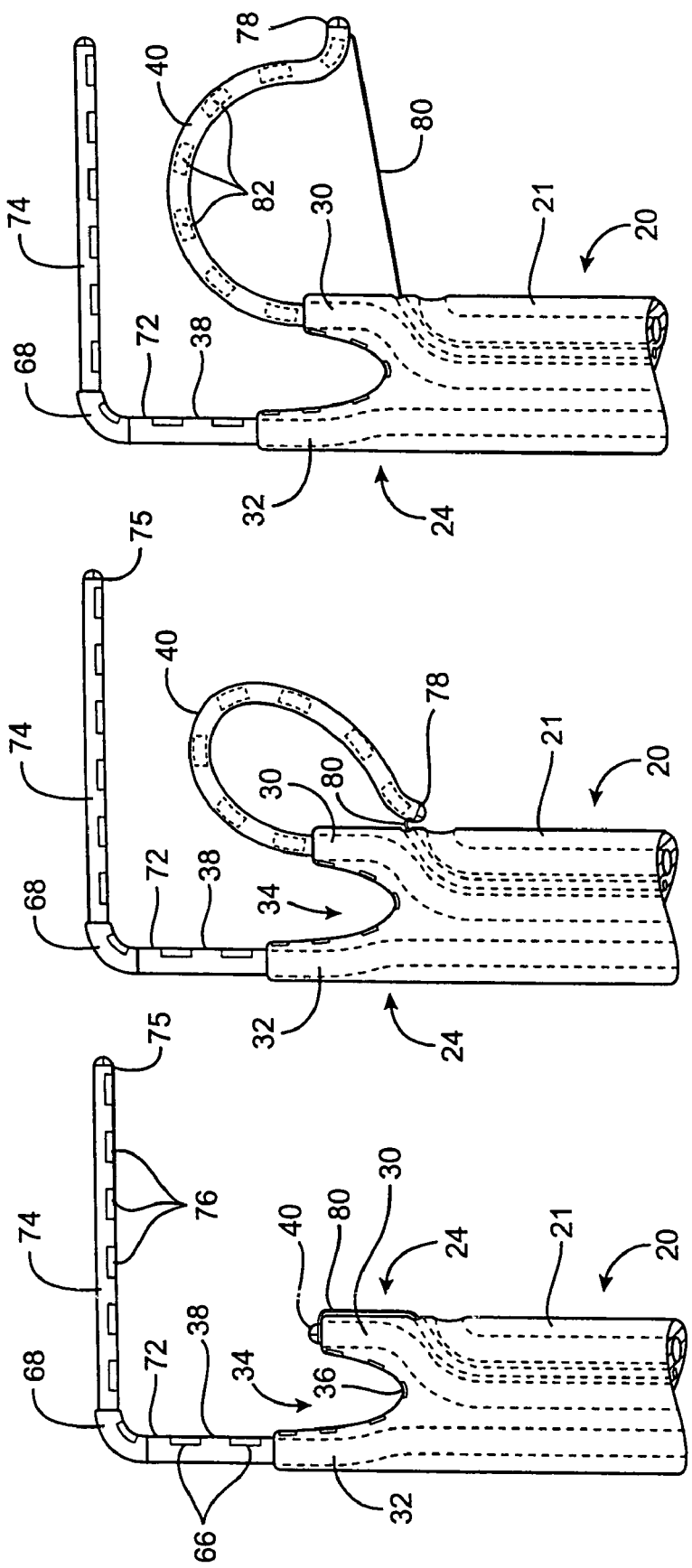

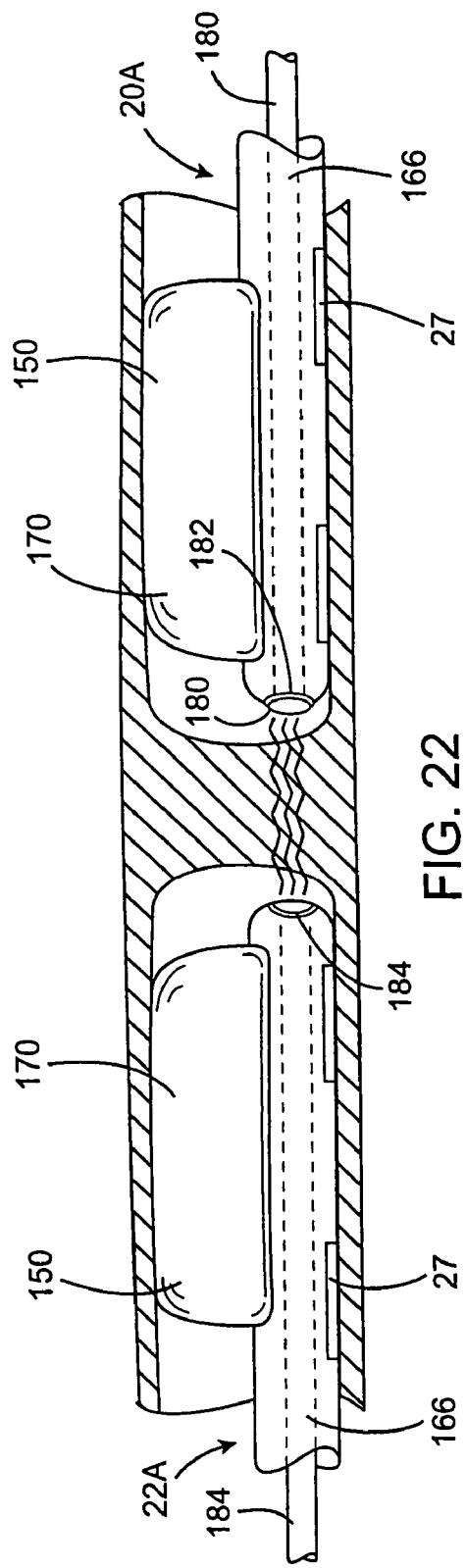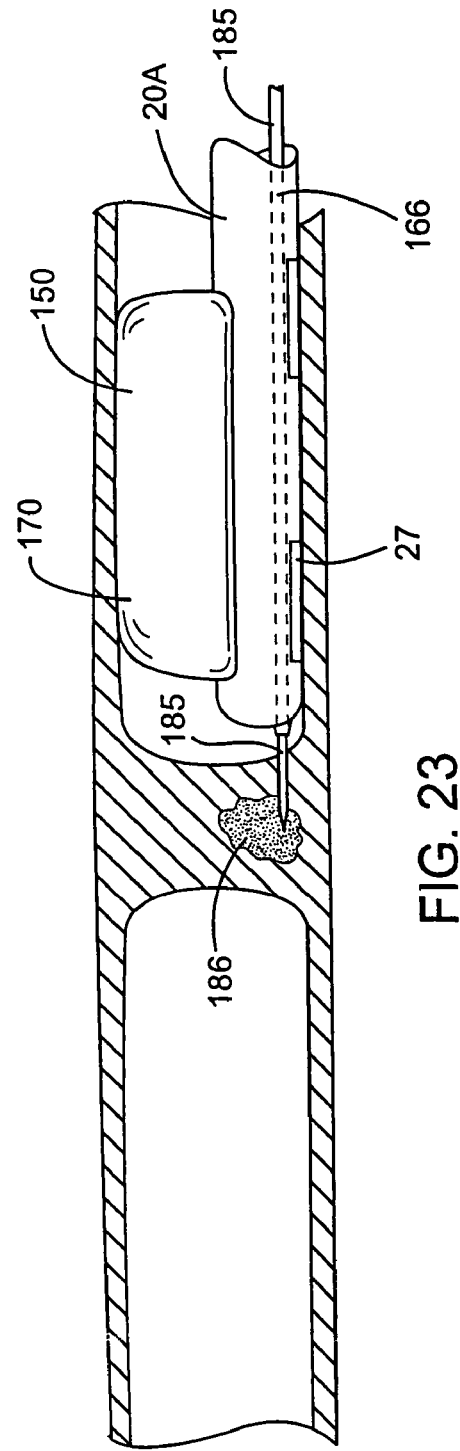

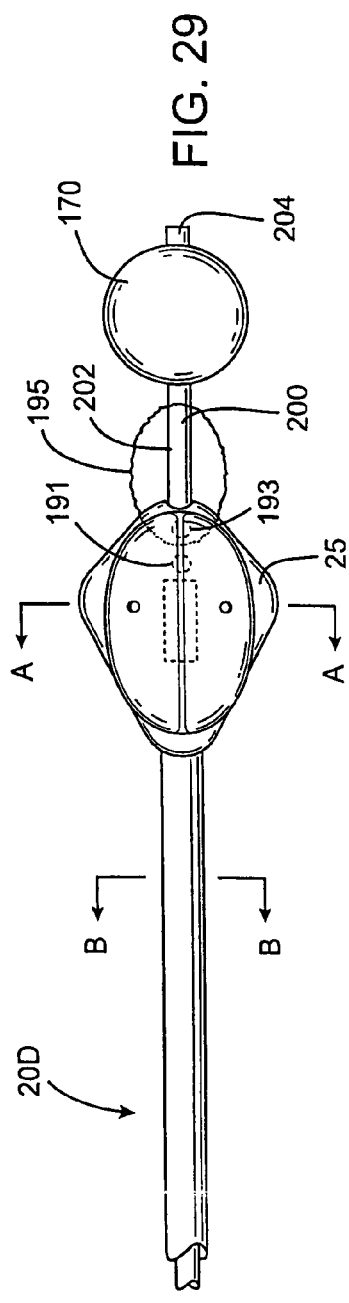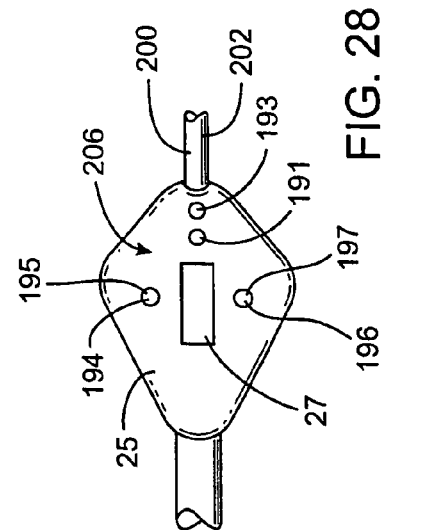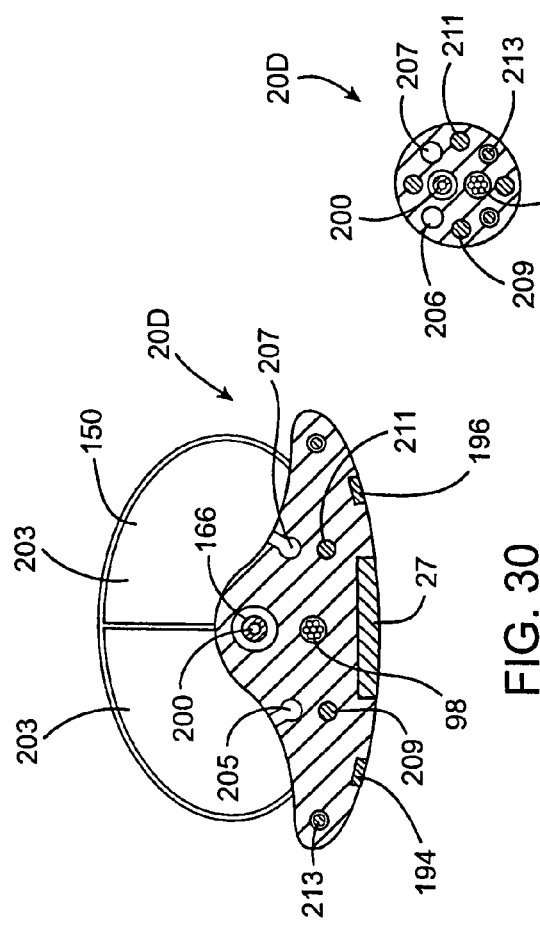

METHODS AND DEVICES FOR ABLATION

The present application is a continuation of application Ser. No. 11/237,619, filed Sep. 27, 2005, now pending, which is a continuation of application Ser. No. 10/006,088, filed Dec. 5, 2001, now abandoned, which is a continuation of application Ser. No. 09/884,435, filed Jun. 19, 2001, now U.S. Pat. No. 6,719,755, which is a continuation-in-part of application Ser. No. 09/614,991, filed Jul. 12, 2000, now U.S. Pat. No. 6,805,128, which is a continuation-in-part of application Ser. No. 09/507,336, filed Feb. 18, 2000, now abandoned, which is a continuation-in-part of application Ser. No. 09/356,476, filed Jul. 19, 1999, now U.S. Pat. No. 6,311,692, which is a continuation-in-part of application Ser. No. 09/157,824, filed Sep. 21, 1998, now U.S. Pat. No. 6,237,605, which is a continuation-in-part of application Ser. No. 08/943,683, filed Oct. 15, 1997, now U.S. Pat. No. 6,161,543, which is a continuation-in-part of application Ser. No. 08/735,036, filed Oct. 22, 1996, now abandoned, the full disclosures of which are incorporated herein by reference.

BACKGROUND OF THE INVENTION a. Field of the Invention

This invention relates generally to devices and methods for ablating tissue. The diagnosis and treatment of electrophysiological diseases of the heart, and more specifically to devices and methods for epicardial mapping and ablation for the treatment of atrial fibrillation, are described in connection with the devices and methods of the present invention.

b. Background Art

Atrial fibrillation results from disorganized electrical activity in the heart muscle, or myocardium. The surgical maze procedure has been developed for treating atrial fibrillation and involves the creation of a series of surgical incisions through the atrial myocardium in a preselected pattern so as to create conductive corridors of viable tissue bounded by scar tissue.

As an alternative to the surgical incisions used in the maze procedure, transmural ablation of the heart wall has been proposed. Such ablation may be performed either from within the chambers of the heart (endocardial ablation) using endovascular devices (e.g. catheters) introduced through arteries or veins, or from outside the heart (epicardial ablation) using devices introduced into the chest. Various ablation technologies have been proposed, including cryogenic, radiofrequency (RF), laser and microwave. The ablation devices are used to create elongated transmural lesions—that is, lesions extending through a sufficient thickness of the myocardium to block electrical conduction—which form the boundaries of the conductive corridors in the atrial myocardium. Perhaps most advantageous about the use of transmural ablation rather than surgical incisions is the ability to perform the procedure on the beating heart without the use of cardiopulmonary bypass.

In performing the maze procedure and its variants, whether using ablation or surgical incisions, it is generally considered most efficacious to include a transmural incision or lesion that isolates the pulmonary veins from the surrounding myocardium. The pulmonary veins connect the lungs to the left atrium of the heart, and join the left atrial wall on the posterior side of the heart. This location creates significant difficulties for endocardial ablation devices for several reasons. First, while many of the other lesions created in the maze procedure can be created from within the right atrium, the pulmonary venous lesions must be created in the left atrium, requiring either a separate arterial access point or a transeptal puncture from the right atrium. Second, the elongated and flexible endovascular ablation devices are difficult to manipulate into the complex geometries required for forming the pulmonary venous lesions and to maintain in such positions against the wall of the beating heart. This is very time-consuming and can result in lesions which do not completely encircle the pulmonary veins or which contain gaps and discontinuities. Third, visualization of endocardial anatomy and endovascular devices is often inadequate and knowing the precise position of such devices in the heart can be difficult, resulting in misplaced lesions. Fourth, ablation within the blood inside the heart can create thrombus which, in the right chambers, is generally filtered out by the lungs rather than entering the bloodstream. However, on the left side of the heart where the pulmonary venous lesions are formed, thrombus can be carried by the bloodstream into the coronary arteries or the vessels of the head and neck, potentially resulting in myocardial infarction, stroke or other neurologic sequelae. Finally, the heat generated by endocardial devices which flows outward through the myocardium cannot be precisely controlled and can damage extracardiac tissues such as the pericardium, the phrenic nerve and other structures.

What are needed, therefore, are devices and methods for forming lesions that isolate the pulmonary veins from the surrounding myocardium which overcome these problems. The devices and methods will preferably be utilized epicardially to avoid the need for access into the left chambers of the heart and to minimize the risk of producing thrombus.

Additional aspects of the present invention are directed to devices and methods for ablating tissue. Ablation of heart tissue and, specifically, ablation of tissue for treatment of atrial fibrillation is developed as a particular use of these other aspects of the present invention.

BRIEF SUMMARY OF THE INVENTION

The present invention meets these and other objectives by providing epicardial ablation devices and methods useful for creating transmural lesions for the treatment of atrial fibrillation.

In a first embodiment, a method of forming a transmural lesion in a wall of the heart adjacent to the pulmonary veins comprises the steps of placing at least one ablation device through a thoracic incision and through a pericardial penetration so that at least one ablation device is disposed in contact with an epicardial surface of the heart wall; positioning at least one ablation device adjacent to the pulmonary veins on a posterior aspect of the heart while leaving the pericardial reflections intact; and ablating the heart wall with at least one ablating device to create at least one transmural lesion adjacent to the pulmonary veins. While the method may be performed with the heart stopped and circulation supported with cardiopulmonary bypass, the method is preferably performed with the heart beating so as to minimize morbidity, mortality, complexity and cost.

In another aspect of the invention, an apparatus for forming a transmural lesion in the heart wall adjacent to the pulmonary veins comprises, in a preferred embodiment, an elongated flexible shaft having a working end and a control end; an ablation device attached to the working end for creating a transmural lesion in the heart wall; a control mechanism at the control end for manipulating the working end; and a locating device near the working end configured to engage one or more of the pulmonary veins, or a nearby anatomical structure such as a pericardial reflection, for positioning the working end adjacent to the pulmonary veins. The locating device may comprise a catch, branch, notch or other structure at the working end configured to engage one or more of the pulmonary veins or other anatomical structure such as the inferior vena cava, superior vena cava, aorta, pulmonary artery, left atrial appendage, right atrial appendage, or one of the pericardial reflections. The ablation device may be a radiofrequency electrode, microwave transmitter, cryogenic element, laser, ultrasonic transducer or any of the other known types of ablation devices suitable for forming transmural lesions. Preferably, the apparatus includes a plurality of such ablation devices arranged along the working end in a linear pattern suitable for forming a continuous, uninterrupted lesion around or on the pulmonary veins.

The working end may additionally include one or more movable elements that are manipulated from the control end and which may be moved into a desired position after the working end has been located near the pulmonary veins. Slidable, rotatable, articulated, pivotable, bendable, preshaped or steerable elements may be used. Additional ablation devices may be mounted to these movable elements to facilitate formation of transmural lesions. The movable elements may be deployed to positions around the pulmonary veins to create a continuous transmural lesion which electrically isolates the pulmonary veins from the surrounding myocardium.

In addition, a mechanism may be provided for urging all or part of the working end against the epicardium to ensure adequate contact with the ablation devices. This mechanism may be, for example, one or more suction holes in the working end through which suction may be applied to draw the working end against the epicardium, or an inflatable balloon mounted to the outer side of the working end such that, upon inflation, the balloon engages the inner wall of the pericardium and forces the working end against the epicardium. This also functions to protect extracardiac tissues such as the pericardium from injury by retracting such tissues away from the epicardial region which is being ablated, and, in the case of the balloon, providing an insulated barrier between the electrodes of the ablation probe and the extracardiac tissues.

The apparatus may be either a single integrated device or two or more devices which work in tandem. In either case, the apparatus may have two or more tips at the working end which are positioned on opposing sides of a tissue layer such as a pericardial reflection. A device may be provided for approximating the two free ends on opposing sides of the tissue layer, such as an electromagnet mounted to one or both of the free ends. In this way, a continuous lesion may be created in the myocardium from one side of the pericardial reflection to the other without puncturing or cutting away the pericardial reflection.

The apparatus may further include a working channel through which supplemental devices may be placed to facilitate visualization, tissue manipulation, supplementary ablation, suction, irrigation and the like.

The apparatus and methods of the invention are further useful for mapping conduction pathways in the heart (local electrograms) for the diagnosis of electrophysiological diseases. Any of the electrodes on the apparatus may be individually selected and the voltage may be monitored to determine the location of conduction pathways. Alternatively, the apparatus of the invention may be used for pacing the heart by delivering current through one or more selected electrodes at levels sufficient to stimulate heart contractions.

Additionally, although the ablation apparatus and methods of the invention are preferably configured for epicardial use, the principles of the invention are equally applicable to endocardial ablation catheters and devices. For example, an endocardial ablation apparatus according to the invention would include a locating device configured to engage an anatomical structure accessible from within the chambers of the heart such as the coronary sinus (from the right atrium), pulmonary artery (from the right ventricle), or the pulmonary veins (from the left atrium), and the ablation device would be positionable in a predetermined location relative to the locating device. The endocardial apparatus could further include suction holes, expandable balloons, or other mechanisms for maintaining contact between the ablation device and the interior surface of the heart wall.

In another aspect of the present invention, an anchor is used to hold part of the device while displacing another part of the device. The anchor is preferably a balloon but may also be tines, a suction port or a mechanically actuated device. After actuating the anchor, a proximal portion of the device may be moved by simply manipulating the device or by advancement or withdrawal of a stylet.

The present invention is also related to a method of creating a continuous ablation lesion in tissue underlying a pericardial reflection without penetrating the pericardial reflection. First and second ablating devices are introduced into the space between the pericardium and the epicardium. The first ablating device is positioned on one side of the pericardial reflection and the second ablating device is positioned on the other side of the pericardial reflection. Tissue beneath the pericardial reflection is then ablated with one or both of the devices to create a continuous lesion beneath the pericardial reflection. The devices may be aligned across the pericardial reflection by any suitable method such as with magnetic force, use of an emitter and sensor, or by marking the pericardial reflection on one side and locating the mark from the other side of the pericardial reflection. The emitter and sensor may work with electromagnetic radiation such as light, ultrasound, magnetic field, and radiation.

In yet another aspect of the invention, the ablating device may have a guide portion which aligns the device between the pericardium and epicardium. The guide portion may be a continuous strap or a number of discrete guide portions. The guide portions may be fins, wings or one or more laterally extending elements such as balloons. The guide portions may be individually actuated to align the device and ablate discrete locations of the tissue along the ablating device.

The ablating device may also be advanced into position over a guide. The guide is preferably a guidewire but may be any other suitable structure. The guide may also lock into position with a coaxial cable or locking arm. The guide is advanced ahead of the ablation device and positioned along the desired ablation path. The ablating device is then advanced or retracted along the guide. The ablating device preferably includes a device for locating previously formed lesions so that subsequent lesions will merge with a previously formed lesion to create a continuous, transmural lesion. The device for locating previously created lesions may be pacing and sensing electrodes or electrodes which simply measure electrical impedance.

Although cutting through the pericardial reflections has certain risks, the methods and devices of the present invention may, of course, be practiced while cutting through the pericardial reflections. After penetrating through the pericardial reflection, the ablating device may interlock with another part of the same device or with a separate device.

In another method and device of the present invention, another ablating device is provided which may be used to ablate any type of tissue including heart tissue for the reasons described herein. The ablating device has a suction well and an ablating element. The suction well adheres the device to the tissue to be ablated. The device is preferably used to ablate cardiac tissue from an epicardial location to form a transmural lesion. The device preferably includes a number of cells which each have a suction well and at least one ablating element. The cells are coupled together with flexible sections which permit the cells to displace and distort relative to one another. The device preferably has about 5-30 cells, more preferably about 10-25 cells and most preferably about 16 cells. The suction well has an inner lip and an outer lip. The inner lip forms a closed wall around the ablating element.

The device also has a fluid inlet and a fluid outlet for delivering and withdrawing fluid from within the closed wall formed by the inner lip. The fluid is preferably a conductive fluid, such as hypertonic saline, which conducts energy from the ablating element, such as an RF electrode, to the tissue. The fluid is preferably delivered along a short axis of the ablating element so that the temperature change across the ablating element is minimized.

The ablating elements are preferably controlled by a control system. One or more temperature sensors on the device are coupled to the control system for use as now described. The control system may control ablation in a number of different ways. For example, the control system may activate one or more pairs of adjacent cells to form continuous lesions between the adjacent cells. After ablation at the one or more adjacent cells, another pair of adjacent cells is activated to form another continuous ablation segment. This process is continued until a continuous lesion of the desired geometry is produced. In another mode of operation, the control system may activate every other or every third cell. Still another mode of operation is to activate only the ablating elements which have low temperatures by using a multiplexer coupled to the temperature sensors.

The control system may also conduct a thermal response analysis of the tissue to be ablated to determine the appropriate ablation technique. The tissue to be ablated is heated, or cooled, and the temperature response of the tissue over time is recorded. The temperature response is then analyzed to determine the appropriate ablation technique. The analysis may be a comparison of the temperature response against a database of temperature responses or may be a calculation which may require user input as described below.

In a further aspect of the invention, the ablating element preferably produces focused ultrasound in at least one dimension. An advantage of using focused ultrasound is that the energy can be concentrated within the tissue. Another advantage of using focused ultrasound is that the energy diverges after reaching the focus thereby reducing the possibility of damaging tissue beyond the target tissue as compared to collimated ultrasonic energy. When ablating epicardial tissue with collimated ultrasound, the collimated ultrasound energy not absorbed by the target tissue travels through blood and remains concentrated on a relatively small area when it reaches another surface such as the endocardial surface on the other side of a heart chamber. The present invention reduces the likelihood of damage to other structures since the ultrasonic energy diverges beyond the focus and is spread over a larger area. The focused ultrasound has a focal length of about 2 to 20 mm, more preferably about 2 to 12 mm and most preferably about 8 mm in at least one dimension. The focused ultrasound also forms an angle of 10 to 170 degrees, more preferably 30 to 90 degrees and most preferably about 60 degrees as defined relative to a focal axis. The focused ultrasound preferably emits over 90%, and more preferably over 99%, of the energy within the angles and focal lengths described above. The focused ultrasound may be produced in any manner and is preferably produced by a curved transducer with a curved layer attached thereto. The ultrasound is preferably not focused, and may even diverge, when viewed along an axis transverse to the focal axis.

The ultrasound transducers are preferably operated while varying one or more characteristics of the ablating technique such as the frequency, power, ablating time, and/or location of the focal axis relative to the tissue. In a first treatment method, the transducer is activated at a frequency of 2-7 MHz, preferably about 3.5 MHz, and a power of 80-140 watts, preferably about 110 watts, in short bursts. For example, the transducer may be activated for 0.01-1.0 second and preferably about 0.4 second. The transducer is inactive for 2-90 seconds, more preferably 5-80 seconds, and most preferably about 45 seconds between activations. Treatment at this frequency in relatively short bursts produces localized heating at the focus. Energy is not absorbed as quickly in tissue at this frequency as compared to higher frequencies so that heating at the focus is less affected by absorption in the tissue.

In a second treatment method, the transducer is operated for longer periods of time, preferably about 1-4 seconds and more preferably about 2 seconds, to distribute more ultrasound energy between the focus and the near surface. The frequency during this treatment is also 2-14 MHz, more preferably 3-7 MHz and preferably about 6 MHz. The transducer is operated for 0.7-4 seconds at a power of 20-60 watts, preferably about 40 watts. The transducer is inactive for at least 3 seconds, more preferably at least 5 seconds and most preferably at least 10 seconds between each activation.

In a third treatment method, the ultrasonic transducer is activated at a higher frequency to heat and ablate the near surface. The transducer is preferably operated at a frequency of at least 6 MHz and more preferably at least 10 MHz and most preferably about 16 MHz. The transducer is operated at lower power than the first and second treatment methods since ultrasound is rapidly absorbed by the tissue at these frequencies so that the near surface is heated quickly. In a preferred method, the transducer is operated at 2-10 watts and more preferably about 5 watts. The transducer is preferably operated until the near surface NS temperature reaches 70-85 degrees C.

In general, the treatment methods described above deliver energy closer and closer to the near surface NS with each subsequent treatment method. Such a treatment method may be practiced with other devices without departing from this aspect of the invention and, as mentioned below, may be automatically controlled by the control system.

The device preferably has a number of cells with each cell having at least one ablating element. After ablating tissue with all of the cells, gaps may exist between adjacent ablations. The tissue in the gaps is preferably ablated by moving at least one of the ablating elements. In one method, the entire device is shifted so that each cell is used a second time to ablate one of the adjacent gaps. Yet another method of ablating tissue in the gaps is to tilt one or more of the ablating elements to direct the ultrasound energy at the gaps between cells. The ablating element may be moved, tilted or pivoted in any suitable manner and is preferably tilted with an inflatable membrane. The transducer may also simply be configured to direct ultrasound energy to tissue lying beneath the gaps between adjacent transducers. In this manner, the device does not need to be moved or tilted.

The device may be adhered to tissue with suction although suction is not required. The device may also have a membrane filled with a substance which transmits the ultrasound energy to the tissue. The membrane conforms to the tissue and eliminates air gaps between the device and tissue to be ablated. Alternatively, the device may have a solid element which contacts the tissue and transmits the ultrasound energy to the tissue. The device may also be used with a gel applied to the tissue which transmits the ultrasound energy and eliminates air gaps.

The device may also have a number of ultrasound transducers with varying characteristics. For example, the device may have cells which provide focused ultrasound having different focal lengths or which are intended to operate at different frequencies or power. In this manner, the user may select the appropriate cell to ablate a particular tissue structure. For example, it may be desirable to select an ablating element with a small focal length and/or low power when ablating thin tissue.

An advantage of using ultrasound for ablating tissue is that the transducer may be used for other measurements. For example, the transducer may be used to provide temperature, tissue thickness, thickness of fat or muscle layers, and blood velocity data. The ultrasound transducer may also be used to assess the adequacy of contact between the device and the tissue to be ablated. These features find obvious use in the methods described herein and all uses of ultrasound mentioned here, such as temperature feedback control, may be accomplished using other methods and devices.

In another aspect of the invention, the ablating device has a cover which extends over the bottom surface of the ablating device. A fluid cavity is defined by a space between the cover and bottom surface. A flowable material is positioned in the cavity. The device is positioned in the desired ablation position and the cover is then moved to expose the bottom surface while leaving the flowable material positioned between the ablating device and the tissue to be ablated.

In still another aspect of the present invention, the device has a flexible tip which facilitates advancement of the device. The tip preferably extends for at least two inches and is free of any ablating elements. The tip is also preferably removable so that the tip also does not interfere with creating a closed loop.

In yet another aspect of the present invention, a fluid environment is created around the heart and the ablating device is submerged in the fluid environment. The fluid environment helps to ensure that no air bubbles or gaps are present and also can help to regulate the temperature by controlling the fluid temperature.

In still another aspect, a fluid-filled membrane is provided at the contact or bottom surface of the device. The membrane preferably conforms to the shape of the tissue to be ablated and may form a convex contact surface. A fluid may also be circulated through the membrane to provide cooling as necessary. The membrane may also have holes or may be permeable to permit some of the fluid to leak from the membrane into contact with the tissue being ablated.

Other aspects and advantages of the invention are disclosed in the following detailed description and in the accompanying drawings.

BRIEF DESCRIPTION OF THE DRAWING FIGURES

FIGS. 2A-2F are side views of a working end of the left ablation probe of FIG. 1A in various configurations thereof.

Figure 1A:
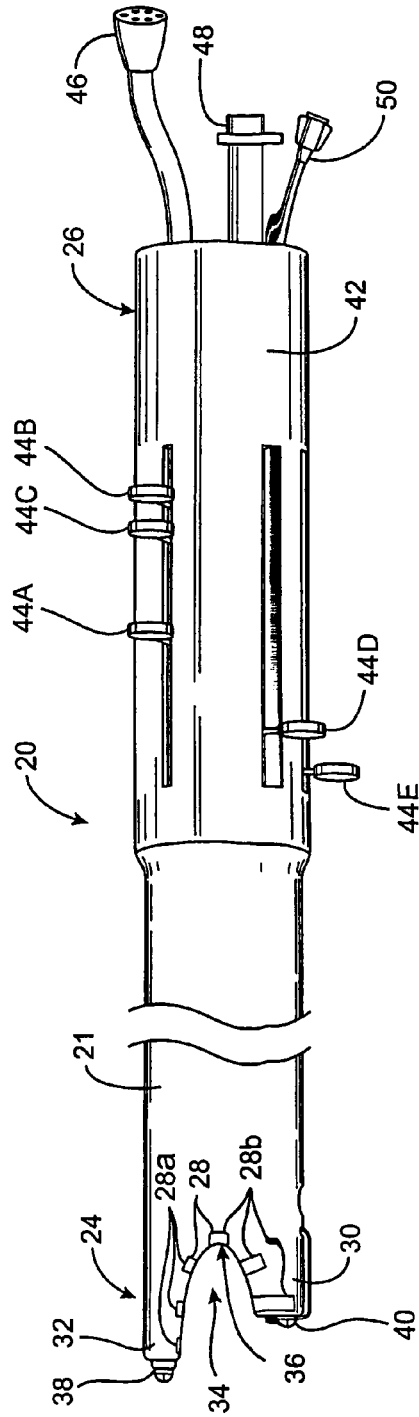
FIG. 1A is side view of a left ablation probe according to the invention.
Figures 5A, 5B, 5C:
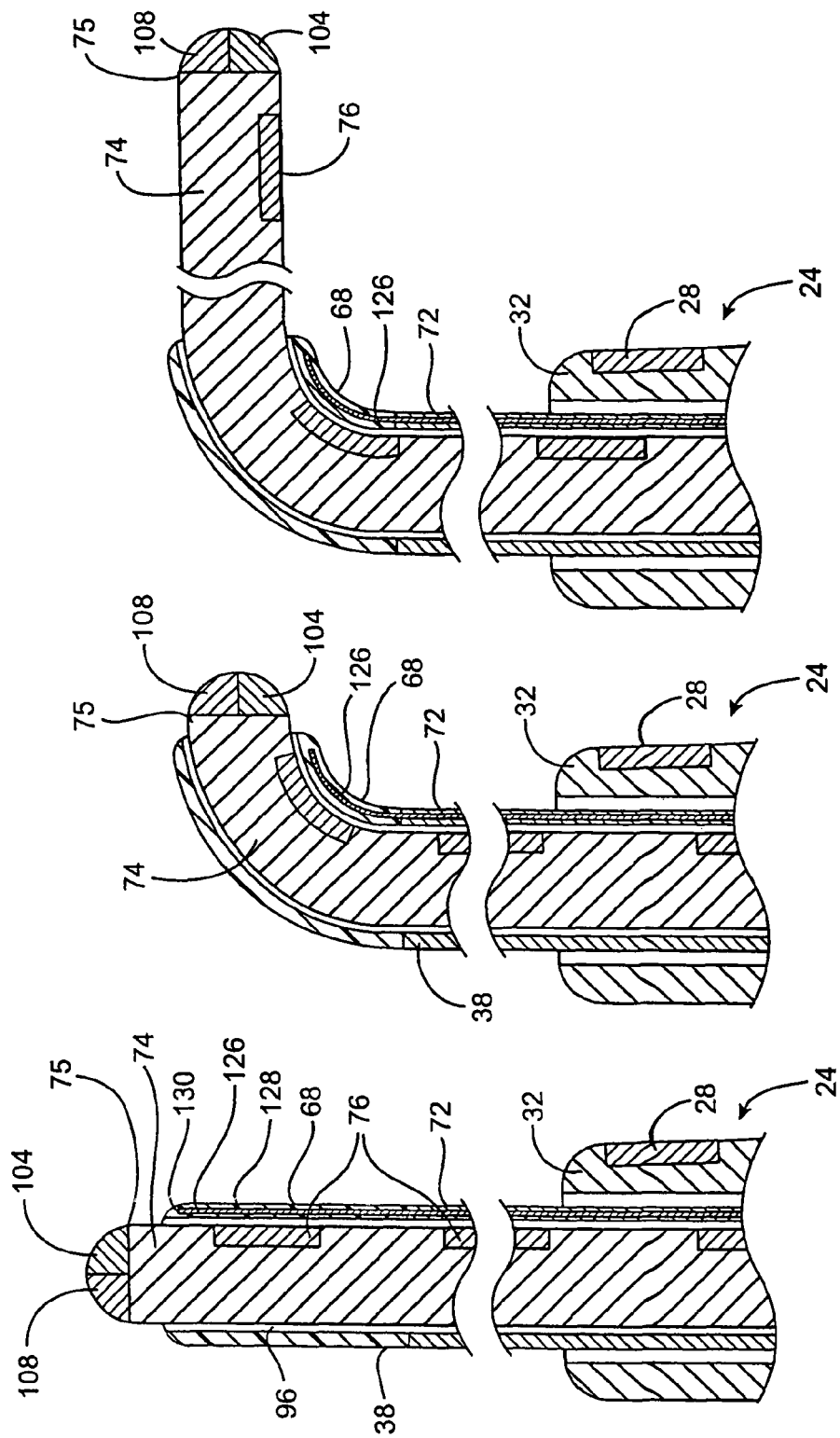

FIGS. 5A-C are partial side cross-sections of the working end of the left ablation probe of FIG. 1A, showing the deployment of a superior sub-probe and inner probe thereof.

Figure 6:
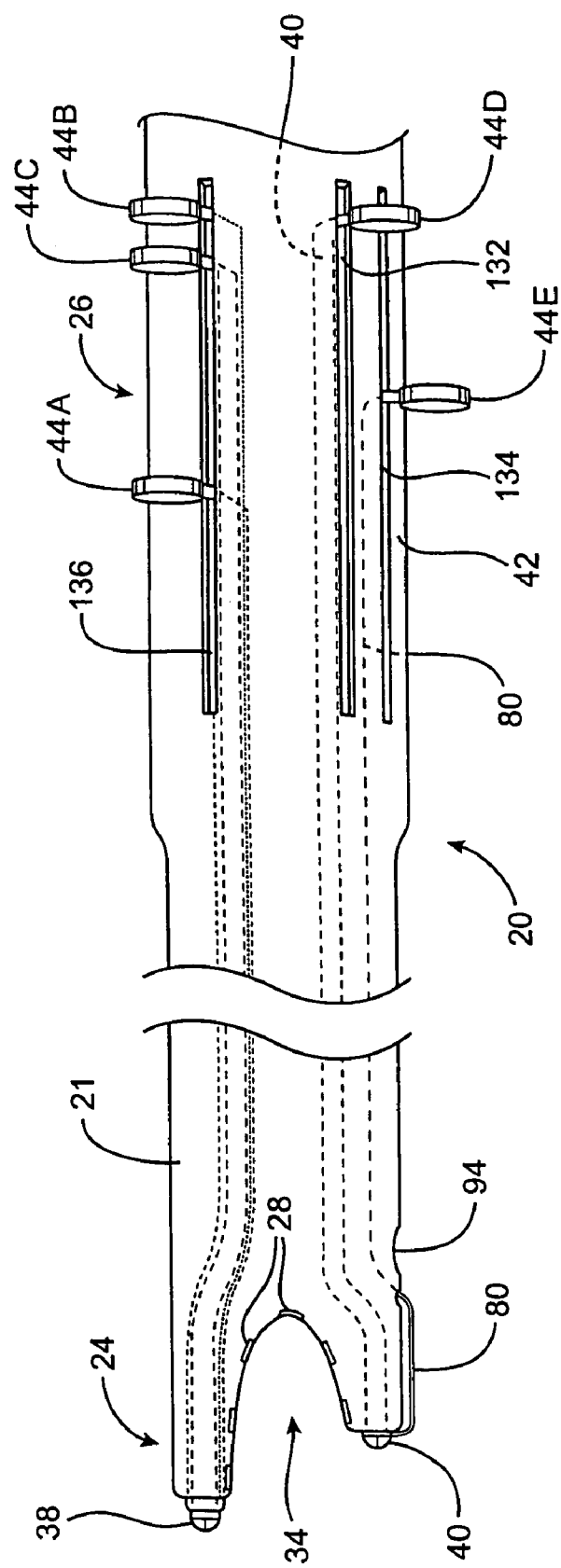

FIG. 6 is a side view of the left ablation probe of FIG. 1A.

Figure 7:
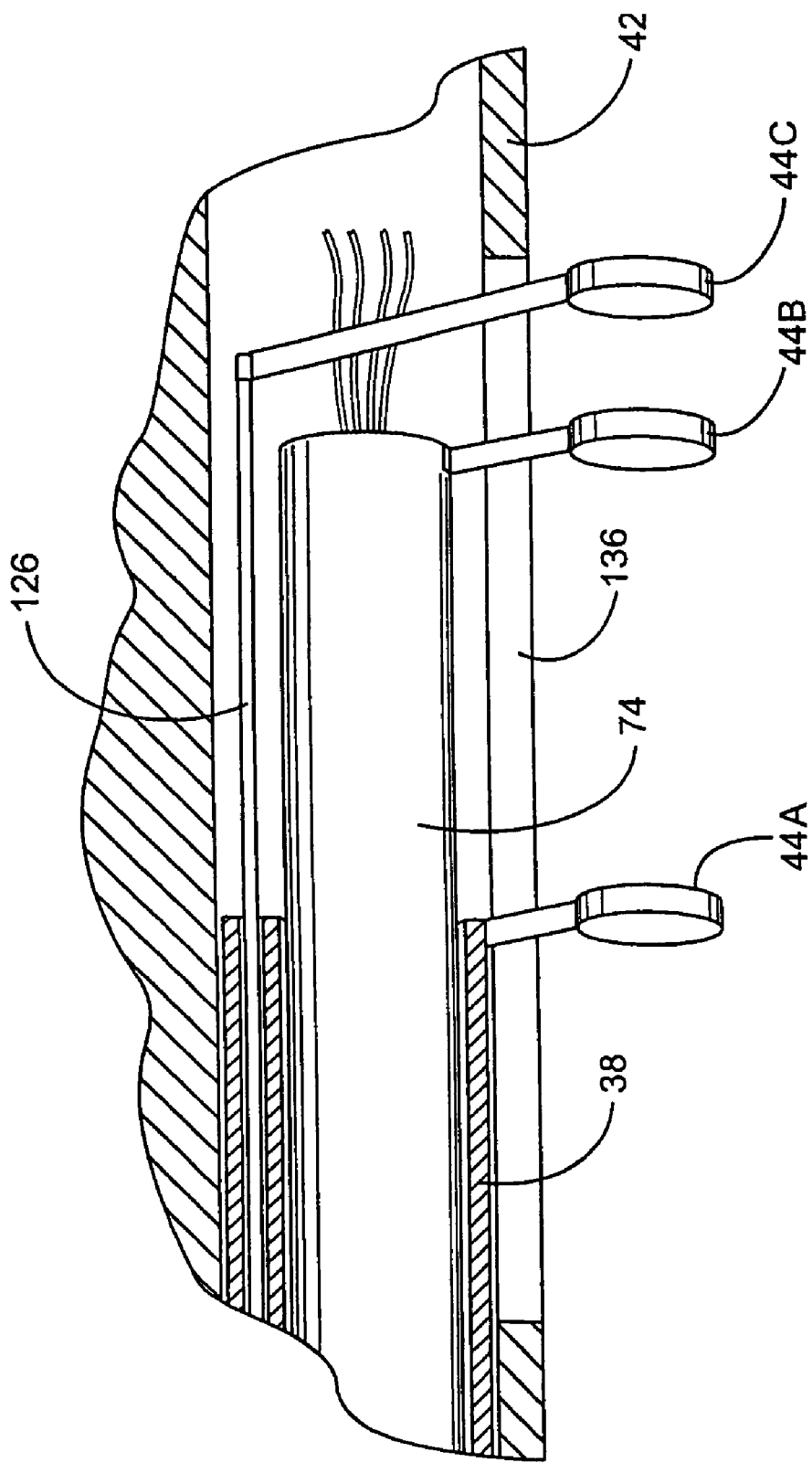

FIG. 7 is a partial side cross-section of the handle of the left ablation probe of FIG. 1A.

Figure 8:
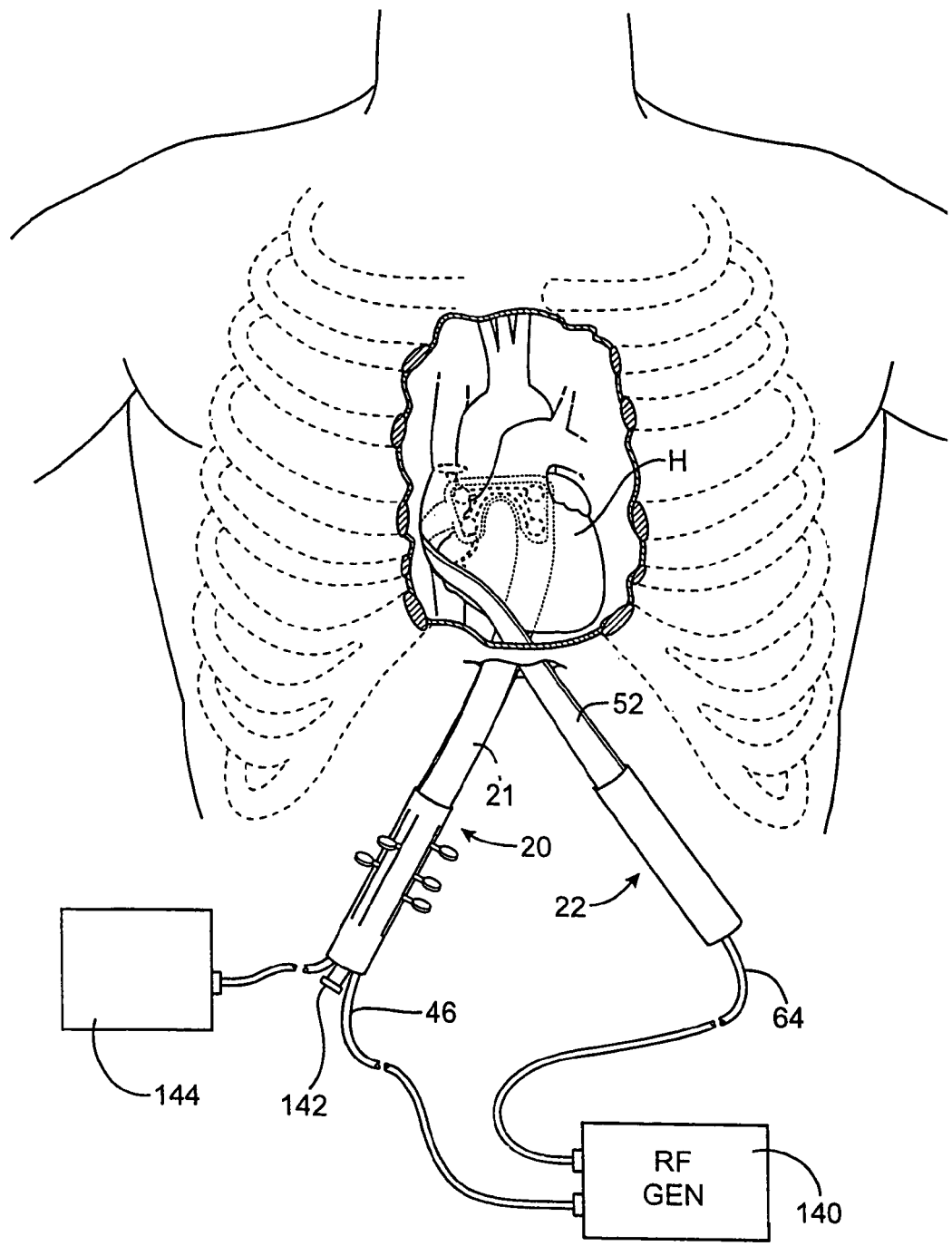

FIG. 8 is an anterior view of the thorax of a patient illustrating the positioning of the left and right ablation probes according to the method of the invention.

Figure 9:
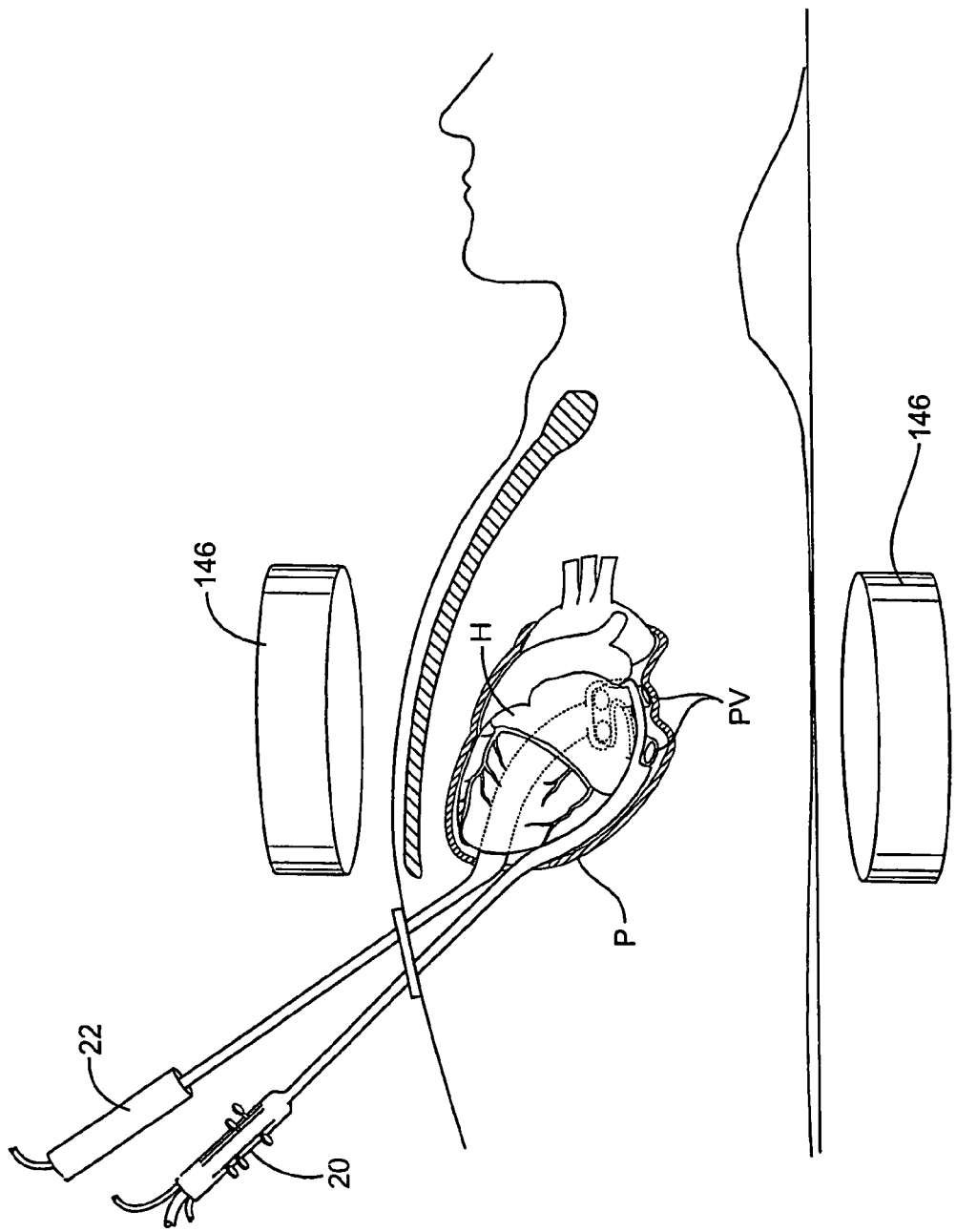

FIG. 9 is a side view of the interior of a patient's thorax illustrating the positioning of the left and right ablation probes according to the method of the invention.

Figure 10:
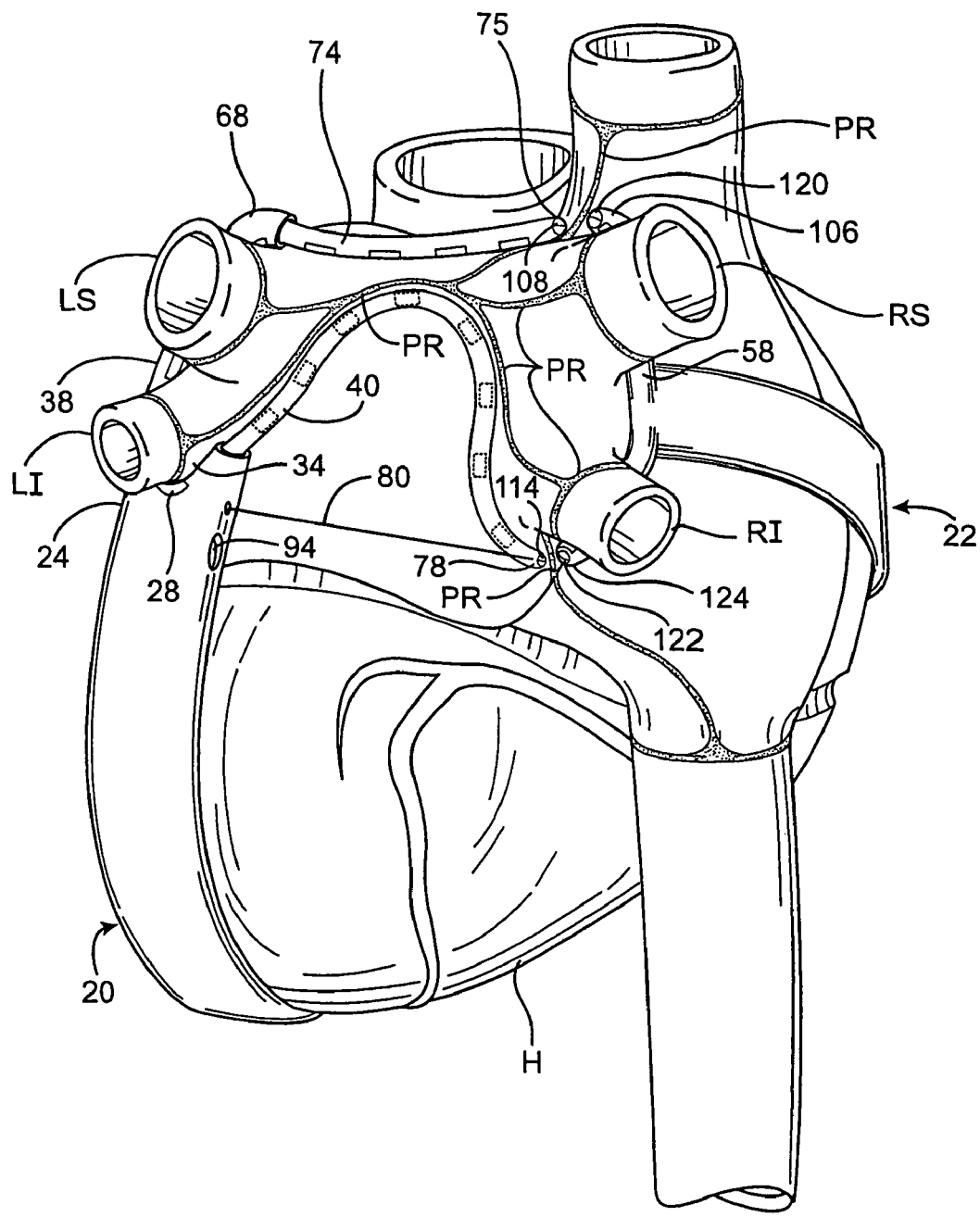

FIG. 10 is a posterior view of a patient's heart illustrating the use of the left and right ablation probes according to the method of the invention.

Figure 11:
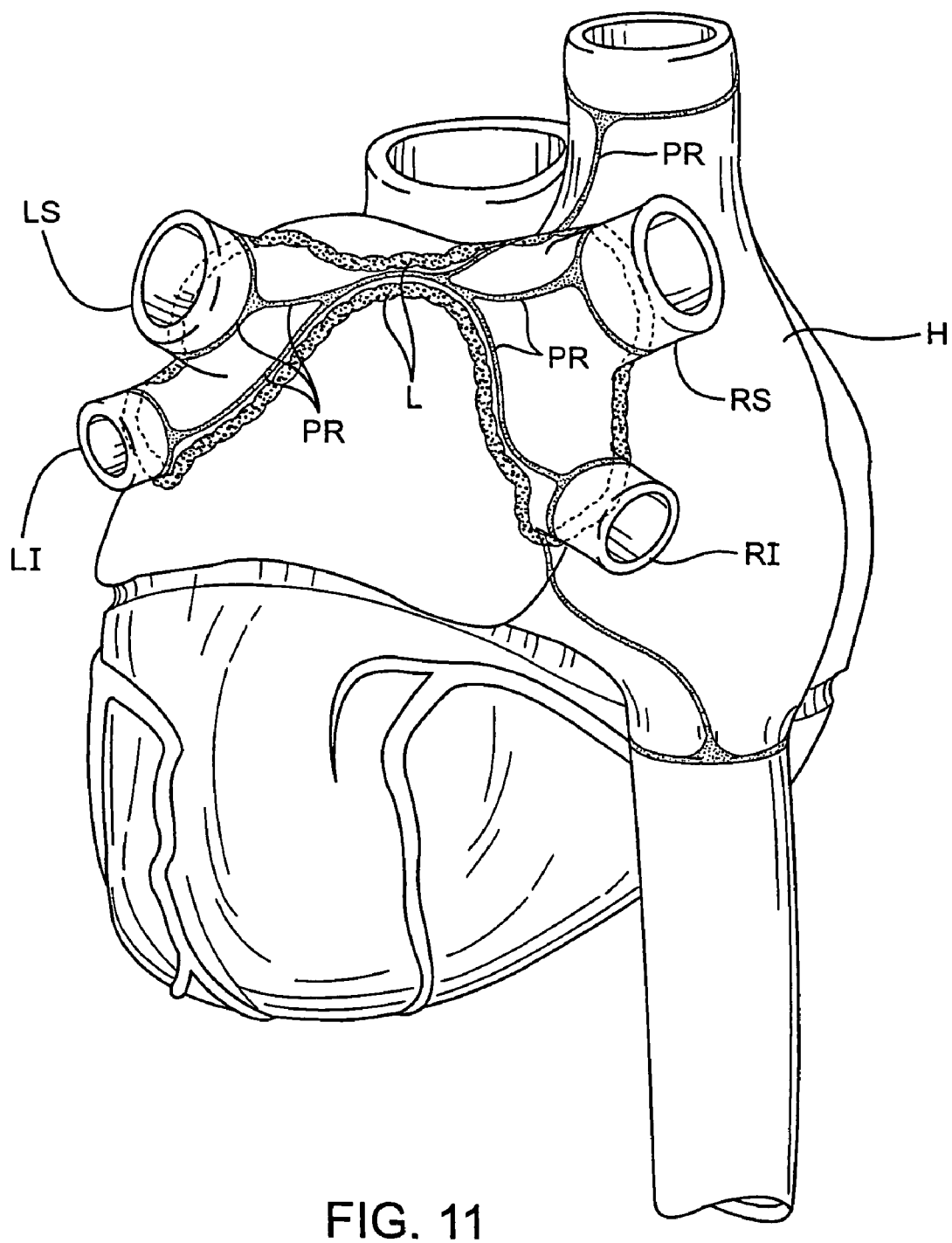

FIG. 11 is a posterior view of a patient's heart illustrating a transmural lesion formed according to the method of the invention.

Figure 12:
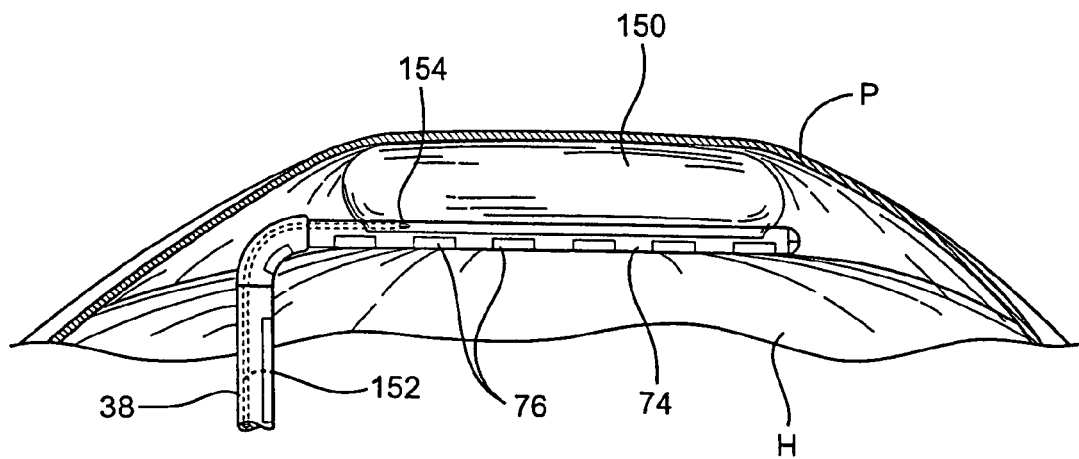
Figure 13:
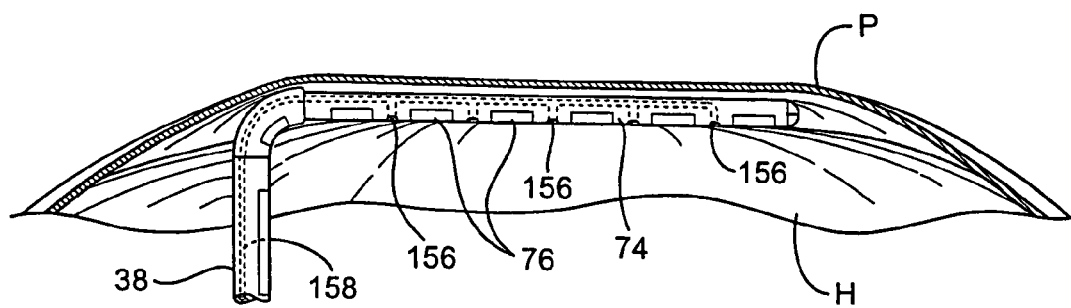

FIGS. 12 and 13 are side views of the left ablation probe of the invention positioned on a patient's heart, showing a balloon and suction ports, respectively, on the inner probe.

Figure 14A:
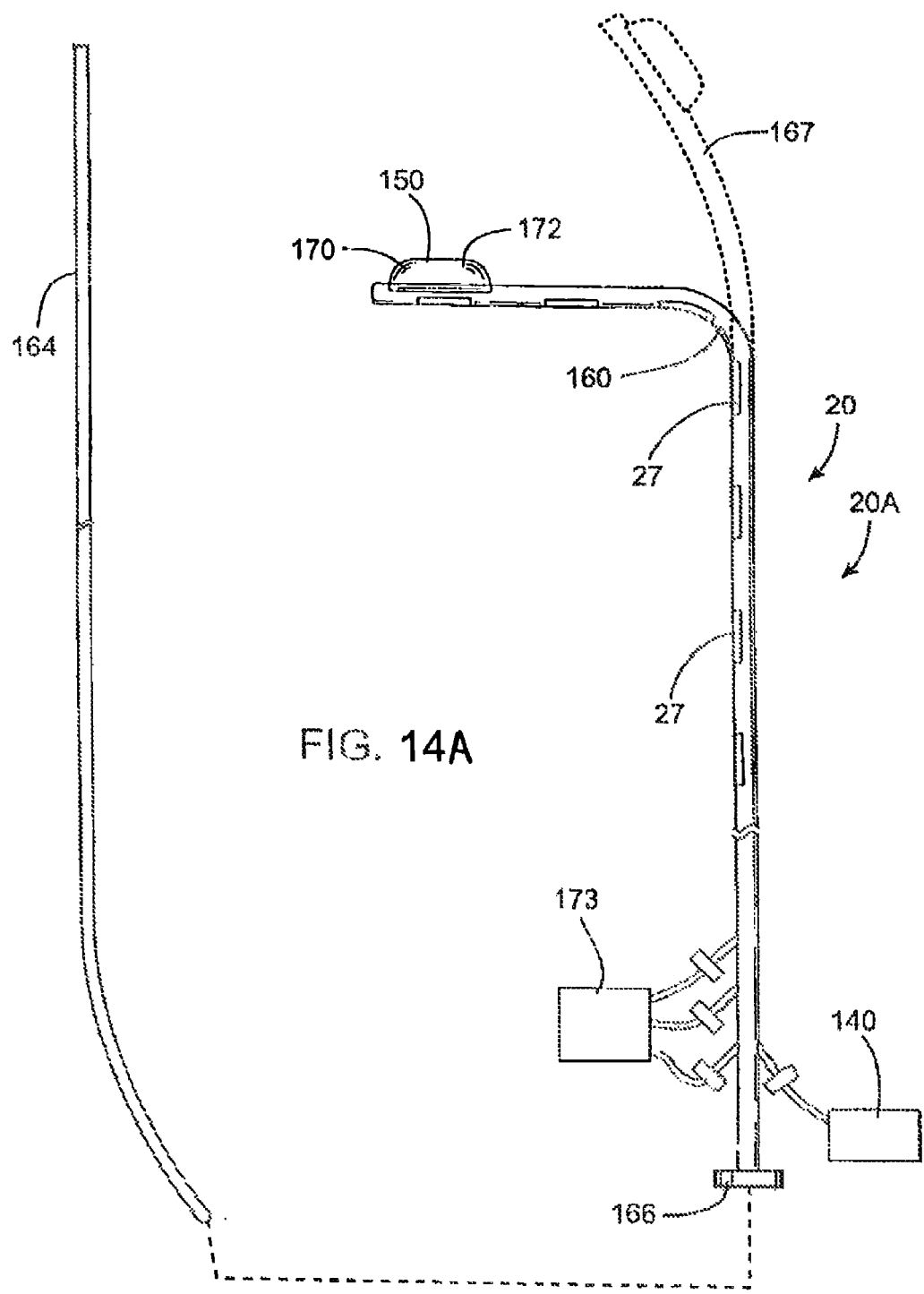

FIG. 14A shows the ablating device having a pre-shaped distal portion.

Figure 14B:
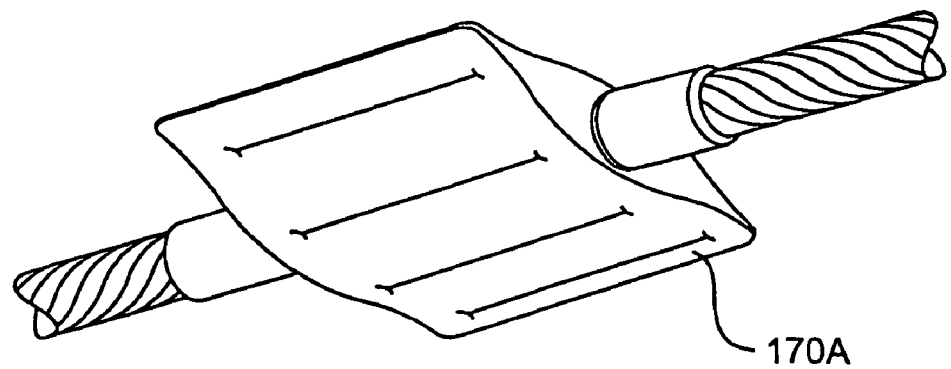

FIG. 14B shows an alternative anchor.

Figure 14C:
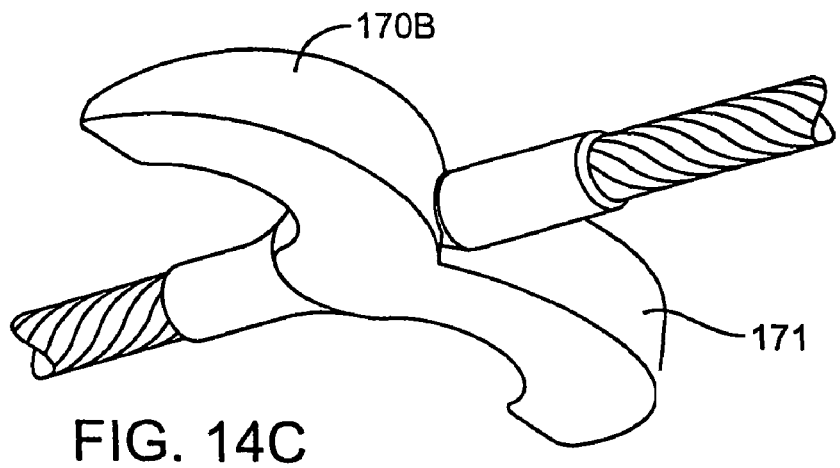

FIG. 14C shows another anchor.

Figure 14D:
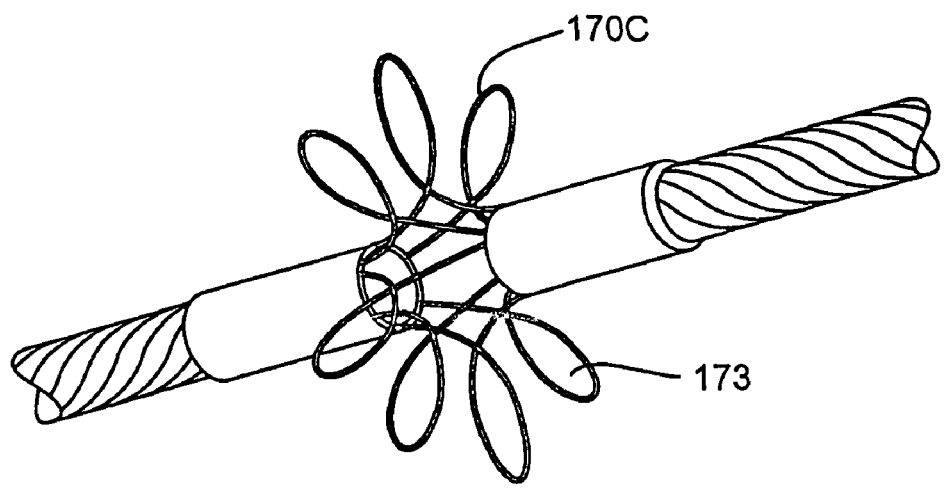

FIG. 14D shows still another anchor.

Figure 15:
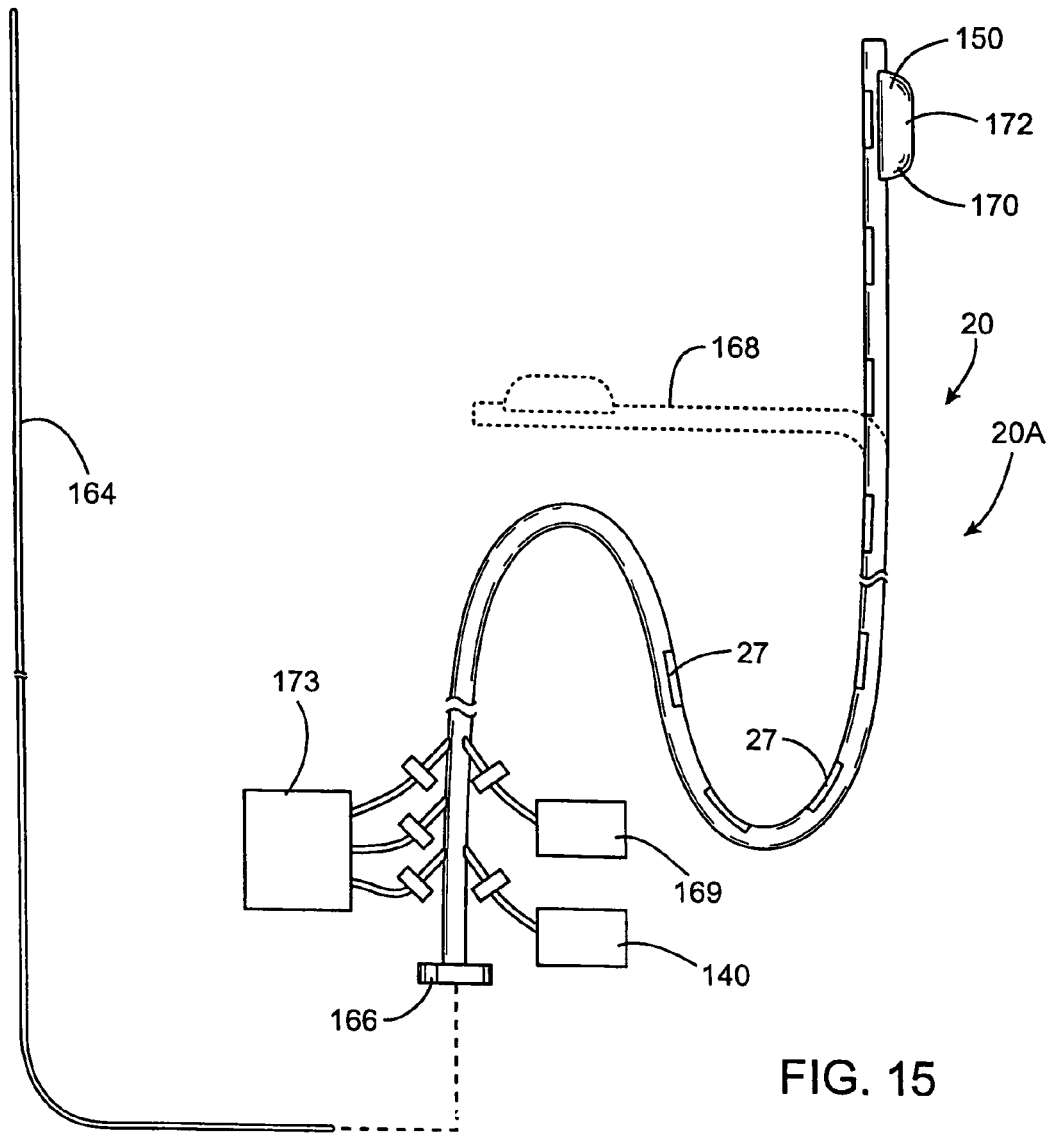

FIG. 15 shows the ablating device having a flexible distal portion which is shaped with a stylet.

Figure 16:
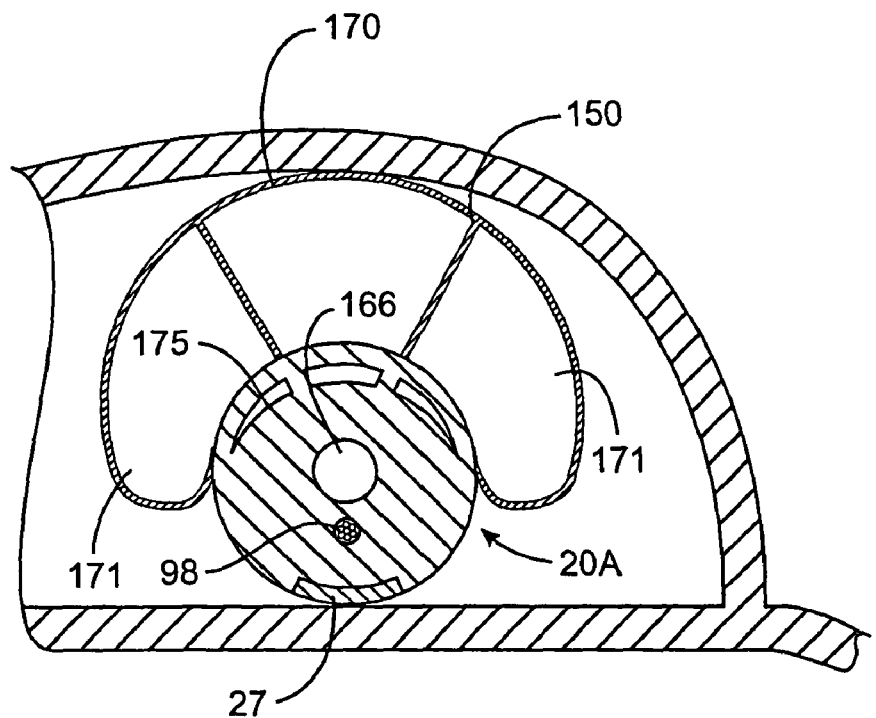

FIG. 16 is a cross-sectional view of the ablating device of FIGS. 14 and 15 with three chambers of the balloon inflated.

Figure 17:
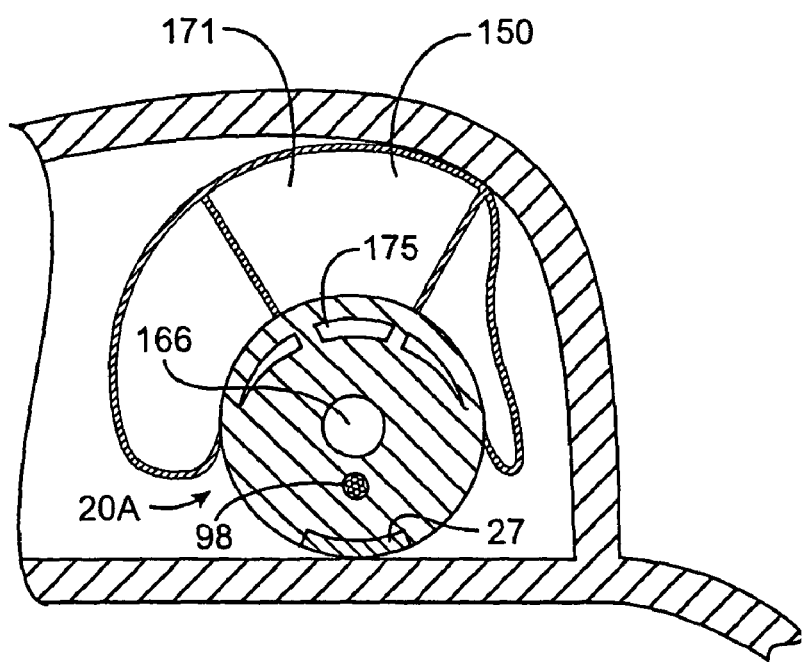

FIG. 17 is a cross-sectional view of the ablating device of FIGS. 14 and 15 with two chambers of the balloon inflated.

Figure 18:
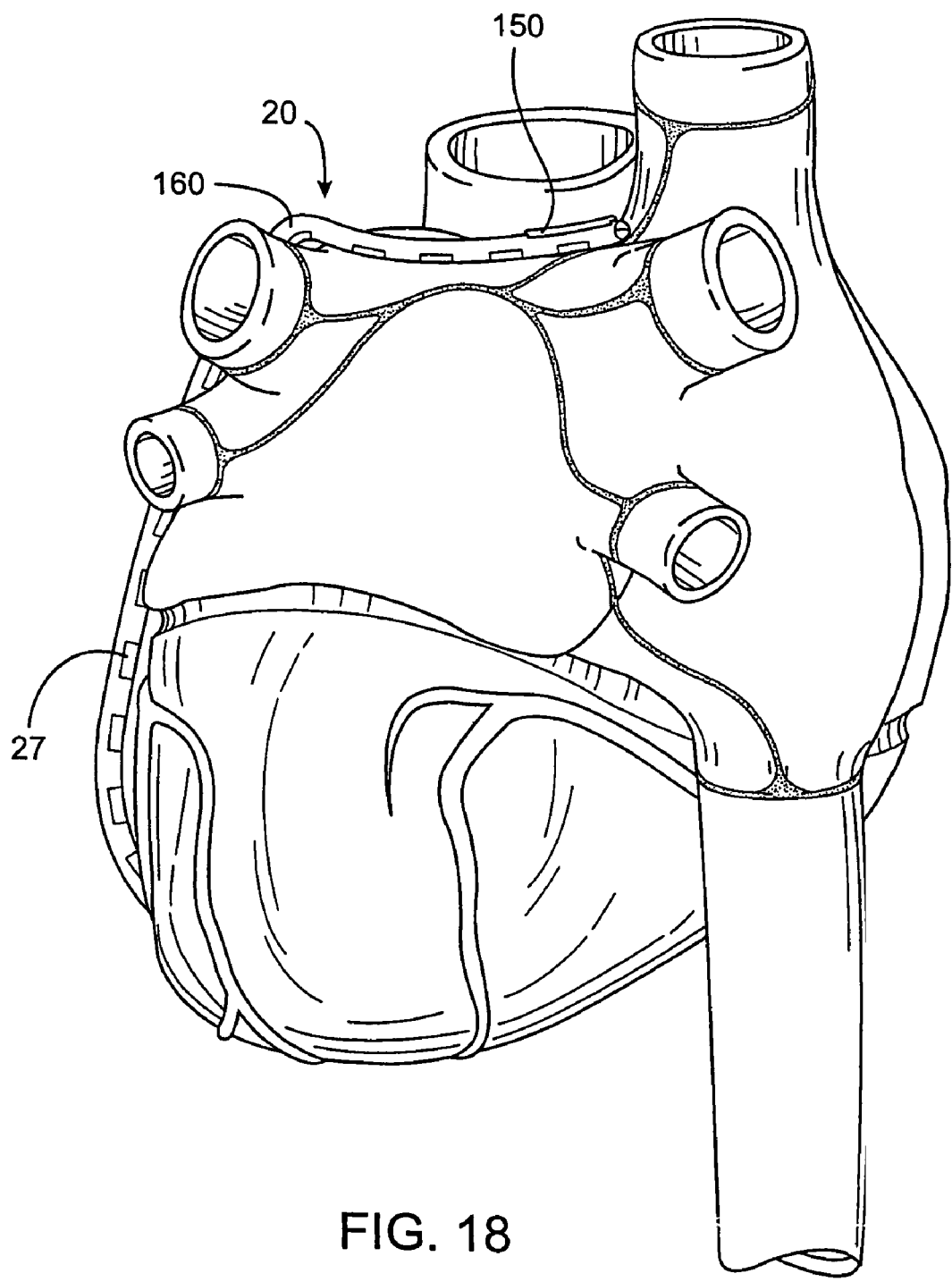

FIG. 18 shows the ablating device advanced into the transverse pericardial sinus with the balloon deflated.

Figure 19:
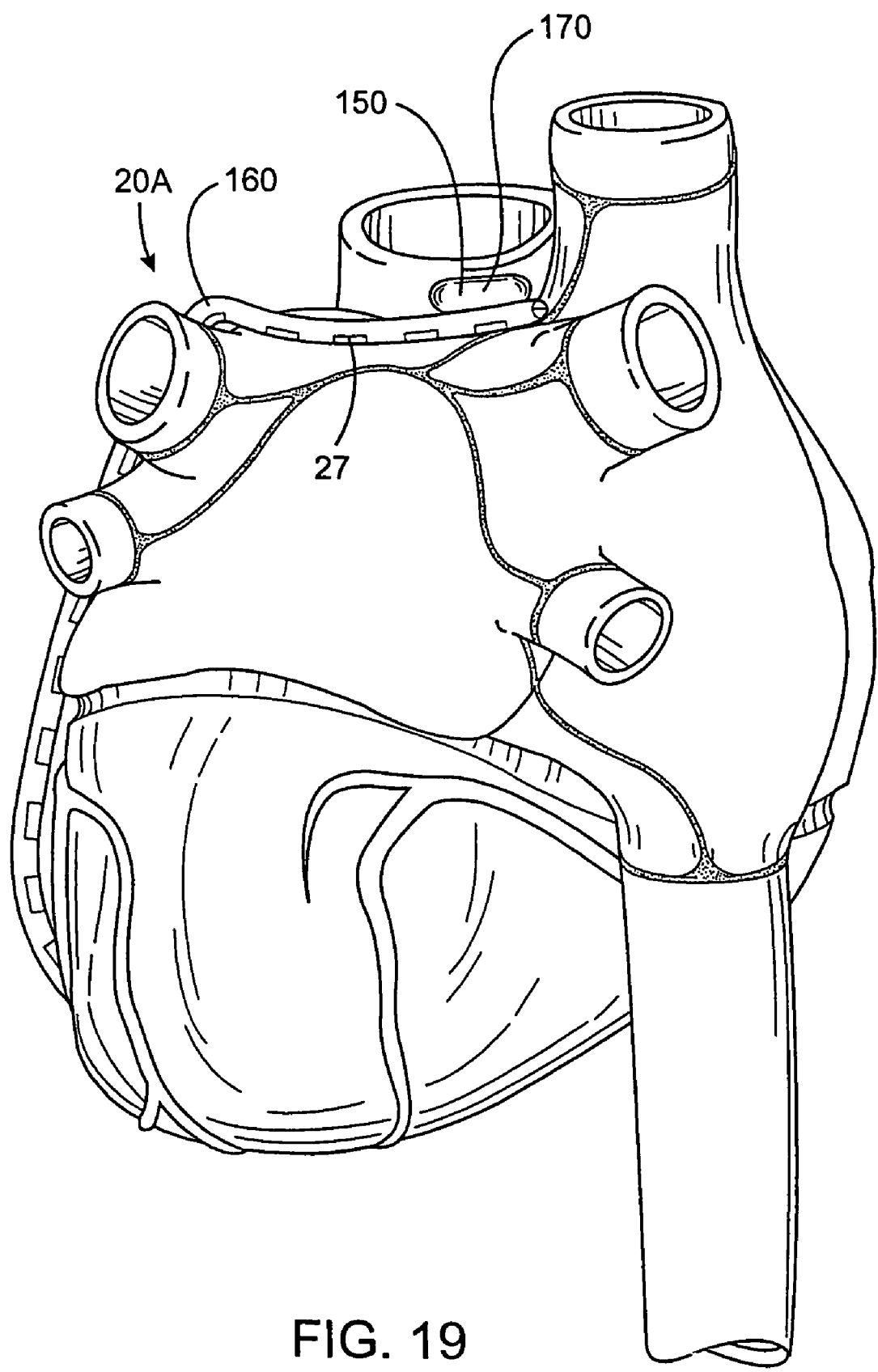

FIG. 19 shows the ablating device advanced into the transverse pericardial sinus with the balloon inflated.

Figure 20:
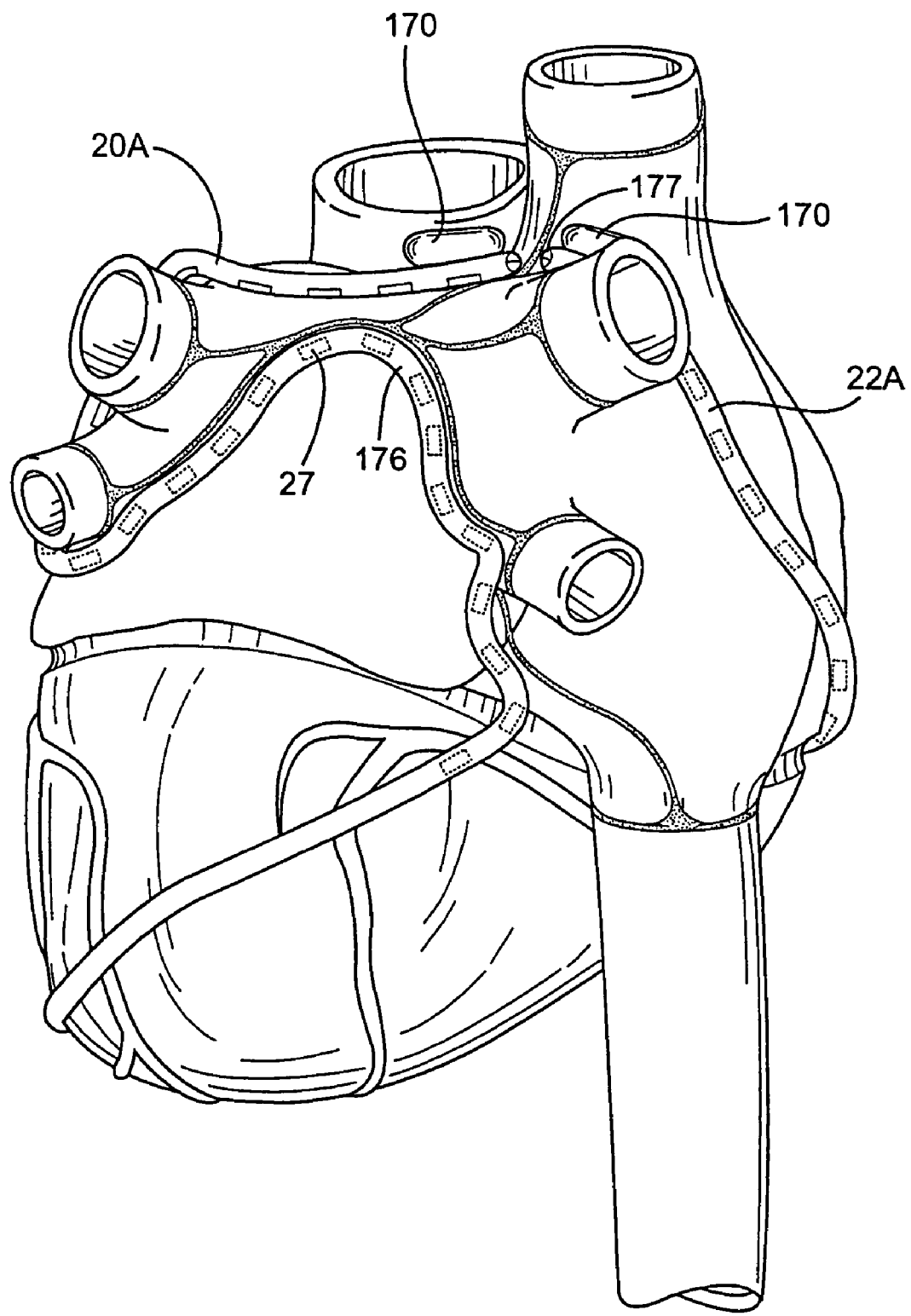

FIG. 20 shows the ablating device extending between the left and right inferior pulmonary veins and another ablating device having an end superior to the right superior pulmonary vein.

Figure 21:
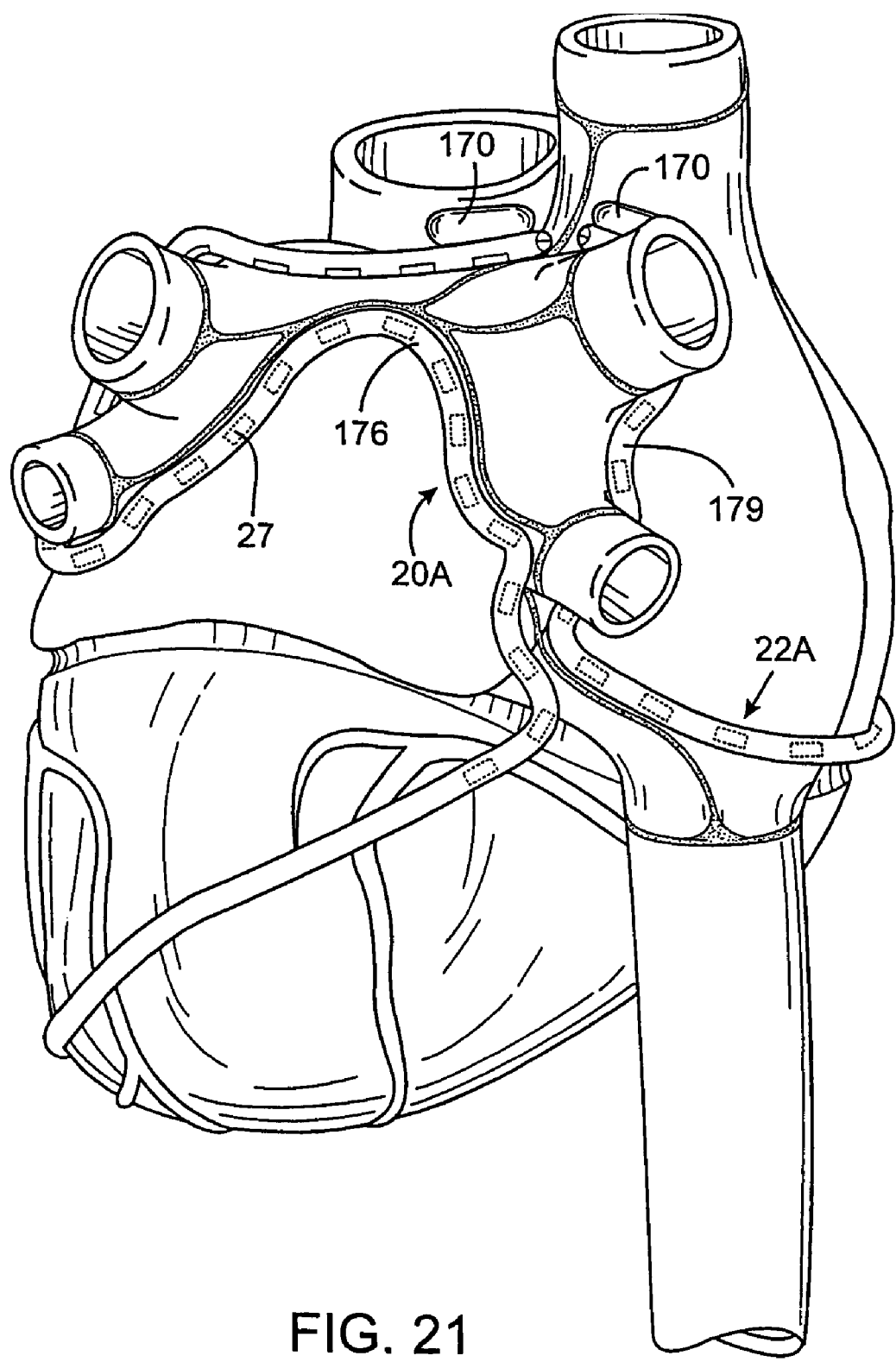

FIG. 21 shows the ablating device moved toward the right superior and right inferior pulmonary veins.

FIG. 22 shows one of the ablating devices having an emitter and the other ablating device having a sensor for aligning the devices across a pericardial reflection.

FIG. 23 shows the ablating device having a needle to deliver a marker which is located on the other side of the pericardial reflection.

Figure 24:
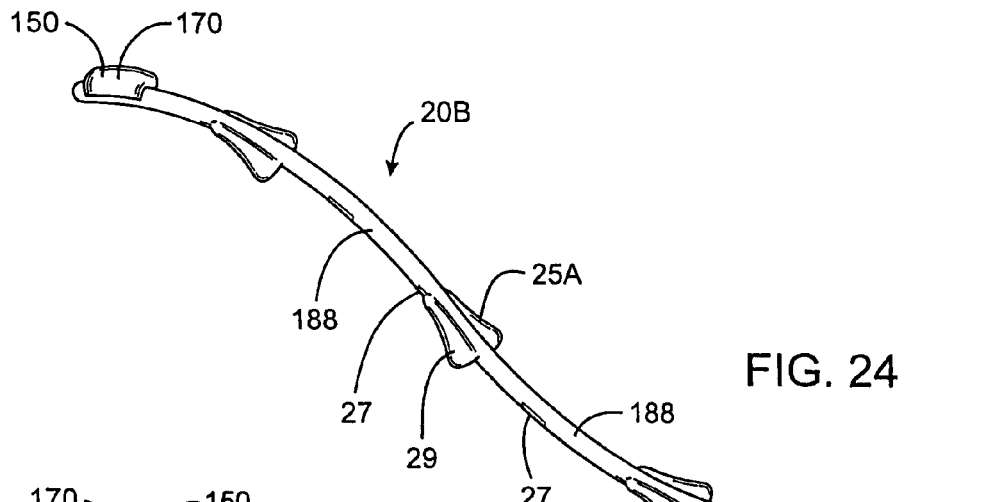

FIG. 24 shows the ablating device having a number of discrete guide portions.

Figure 25:
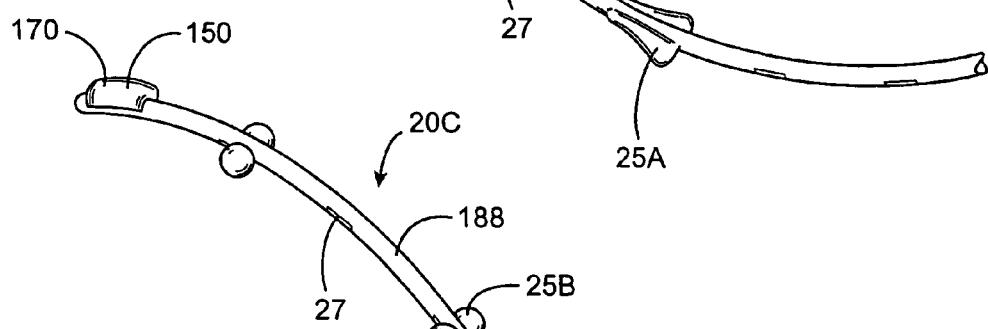

FIG. 25 shows the guide portions being inflatable balloons.

Figure 26:
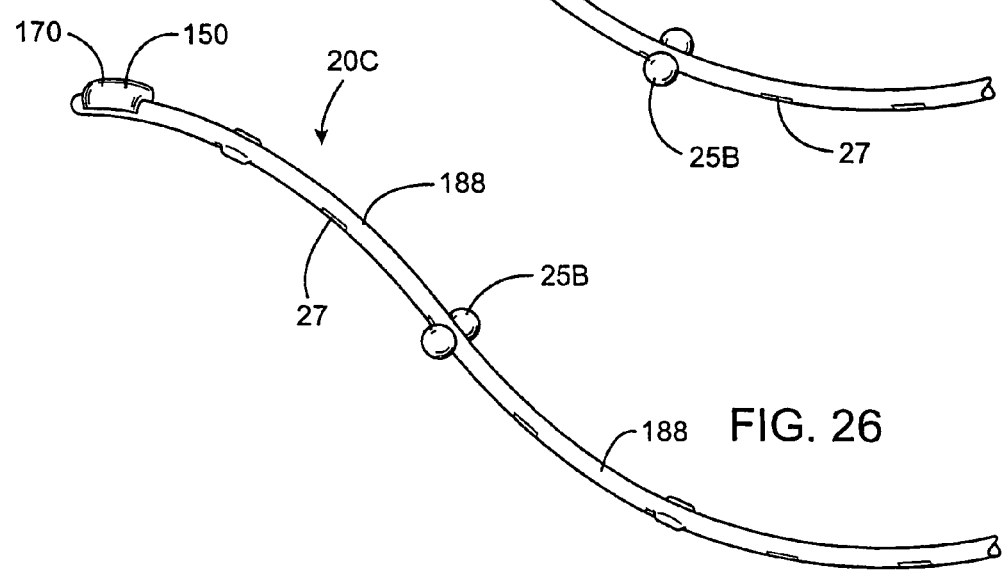

FIG. 26 shows selective inflation of the balloons for selective ablation along the ablating device.

Figure 27A:
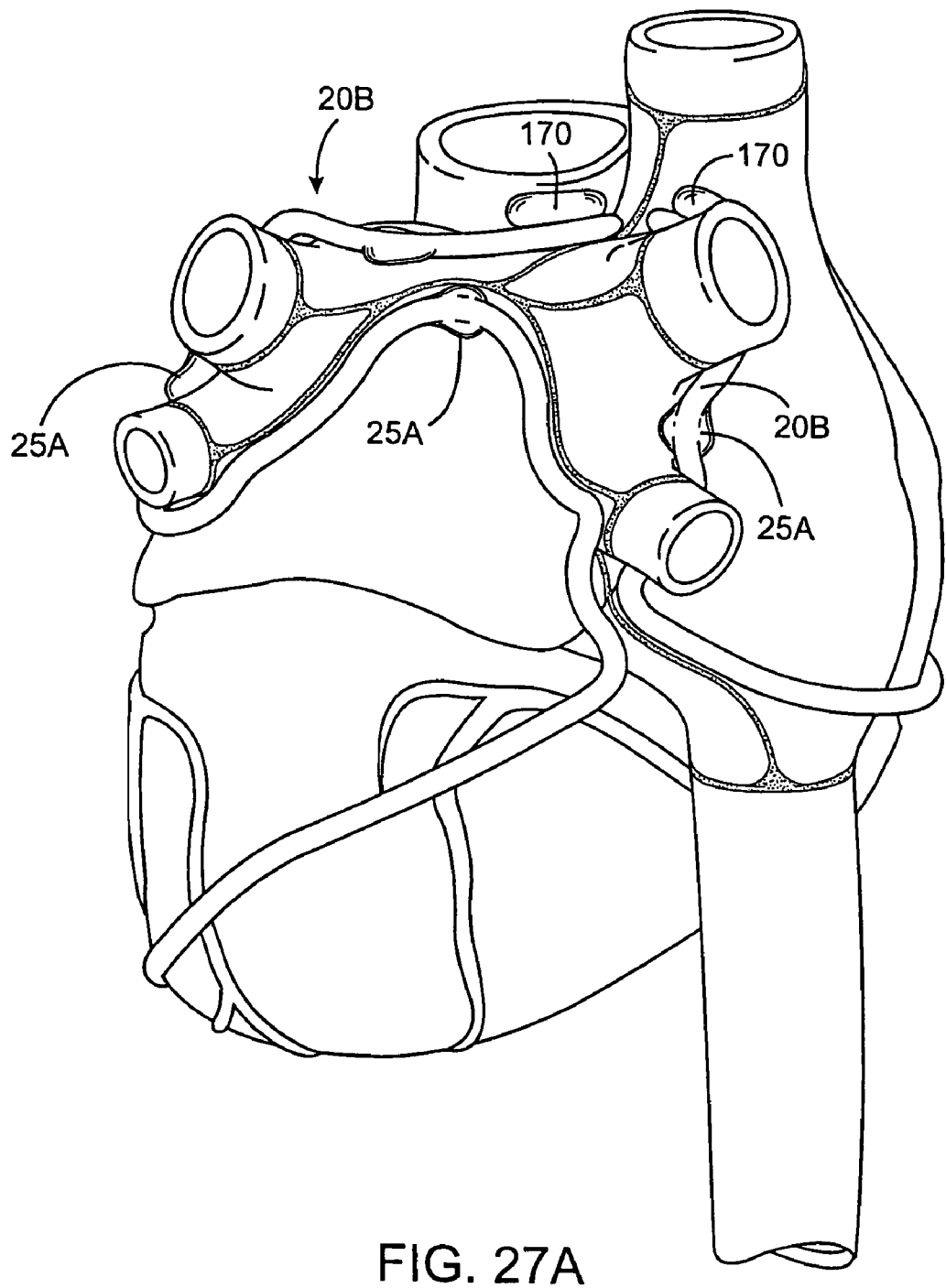

FIG. 27A shows the guide portions used when ablating around the pulmonary veins.

Figure 27B:
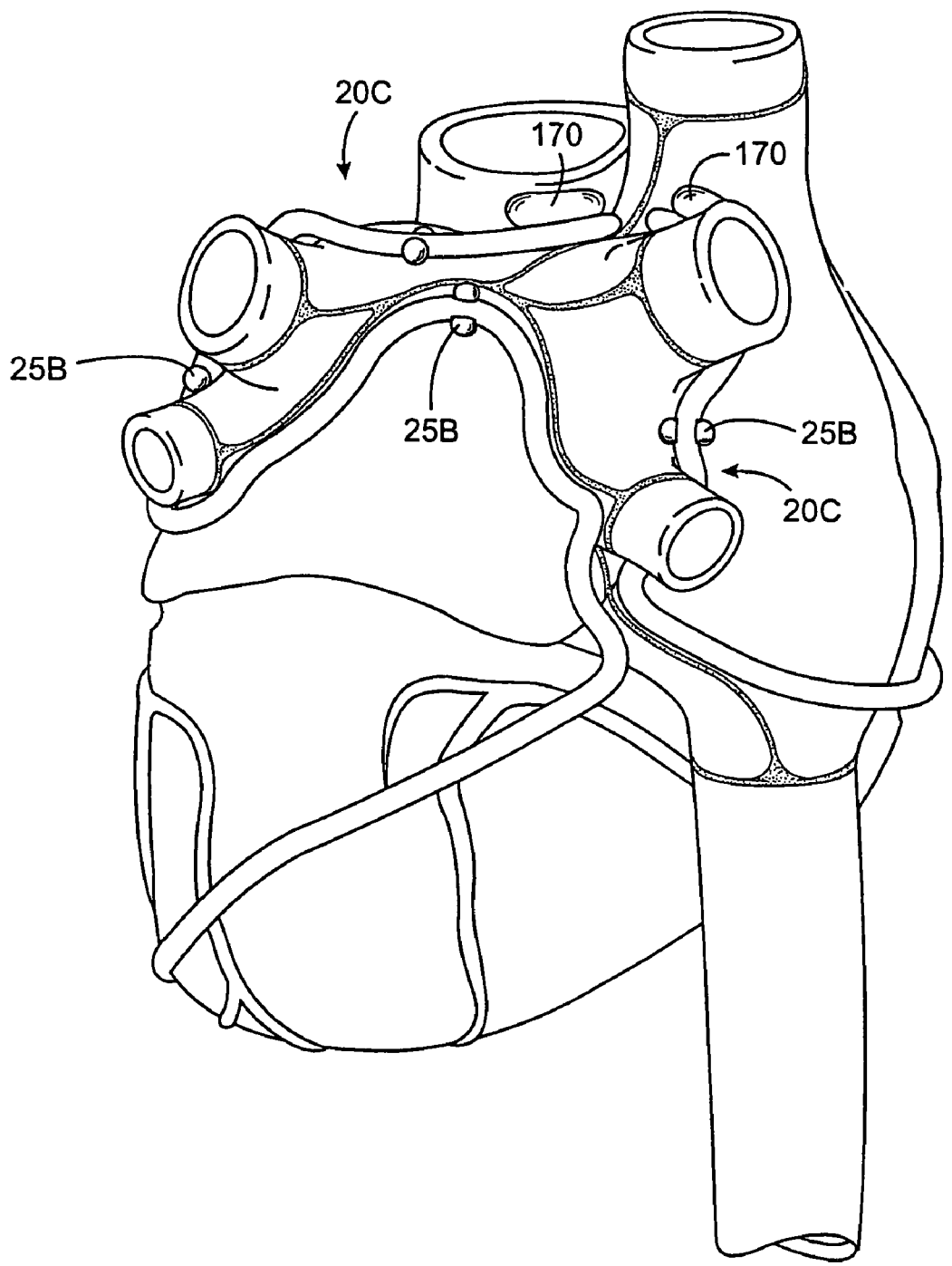

FIG. 27B shows the guide portions being inflatable when ablating around the pulmonary veins.

FIG. 28 is a bottom view of another ablating device which is advanced over a guide.

FIG. 29 is a top view of the ablating device of FIG. 28.

FIG. 30 is a cross-sectional view of the ablating device of FIGS. 28 and 29 along line A-A of FIG. 29.

FIG. 31 is another cross-sectional view of the ablating device of FIGS. 28 and 29 along line B-B of FIG. 29.

Figure 32:

FIG. 32 shows the guide advanced to a desired location with the balloon deflated.

Figure 33:
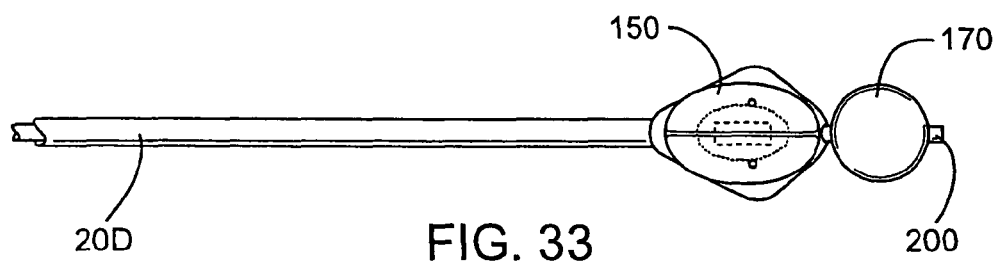

FIG. 33 shows the ablating device advanced over the guide and creating a first lesion.

Figure 34:
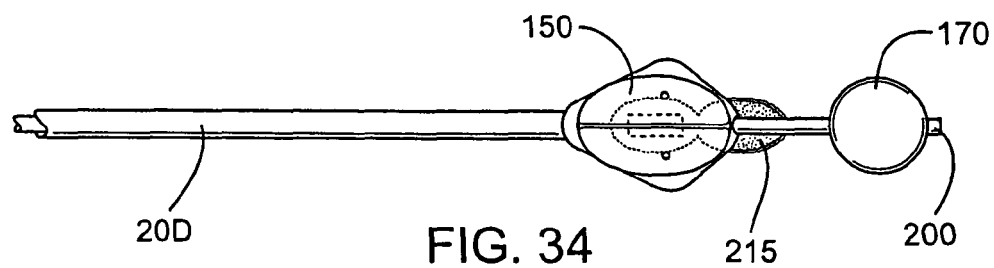

FIG. 34 shows the ablating device creating a second lesion continuous with the first lesion.

Figure 35:
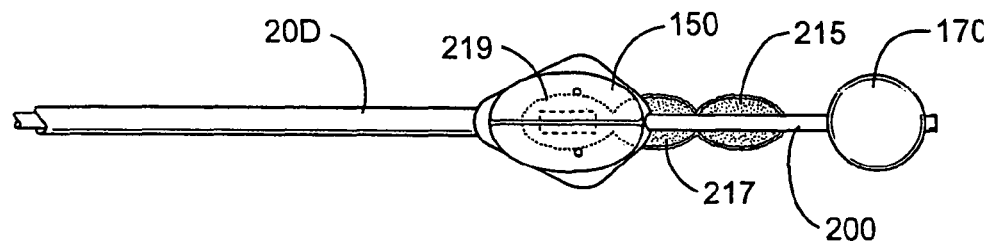

FIG. 35 shows the ablating device creating a third lesion continuous with the second lesion.

Figure 36:
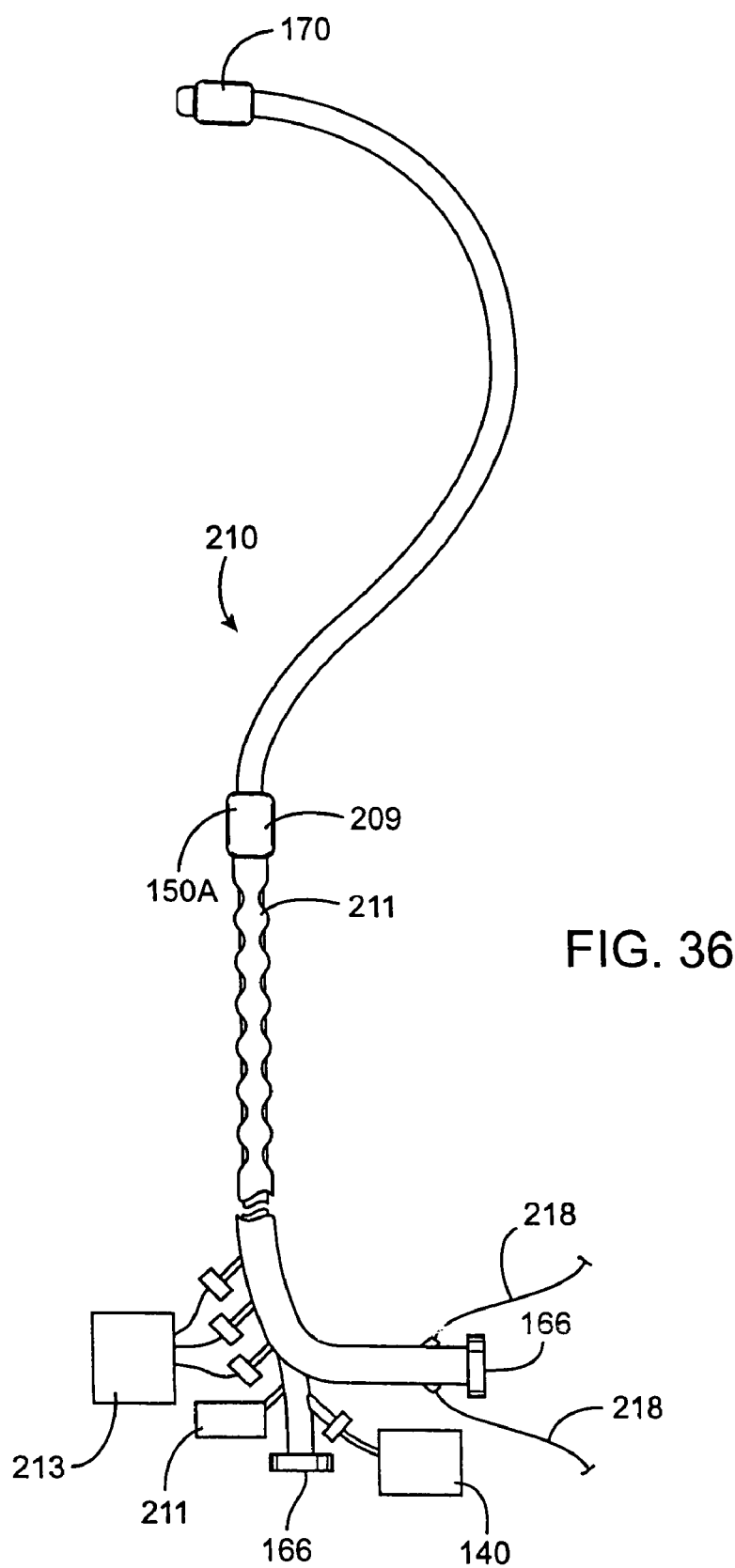

FIG. 36 shows another ablating device having an expandable device movable thereon.

Figure 37:
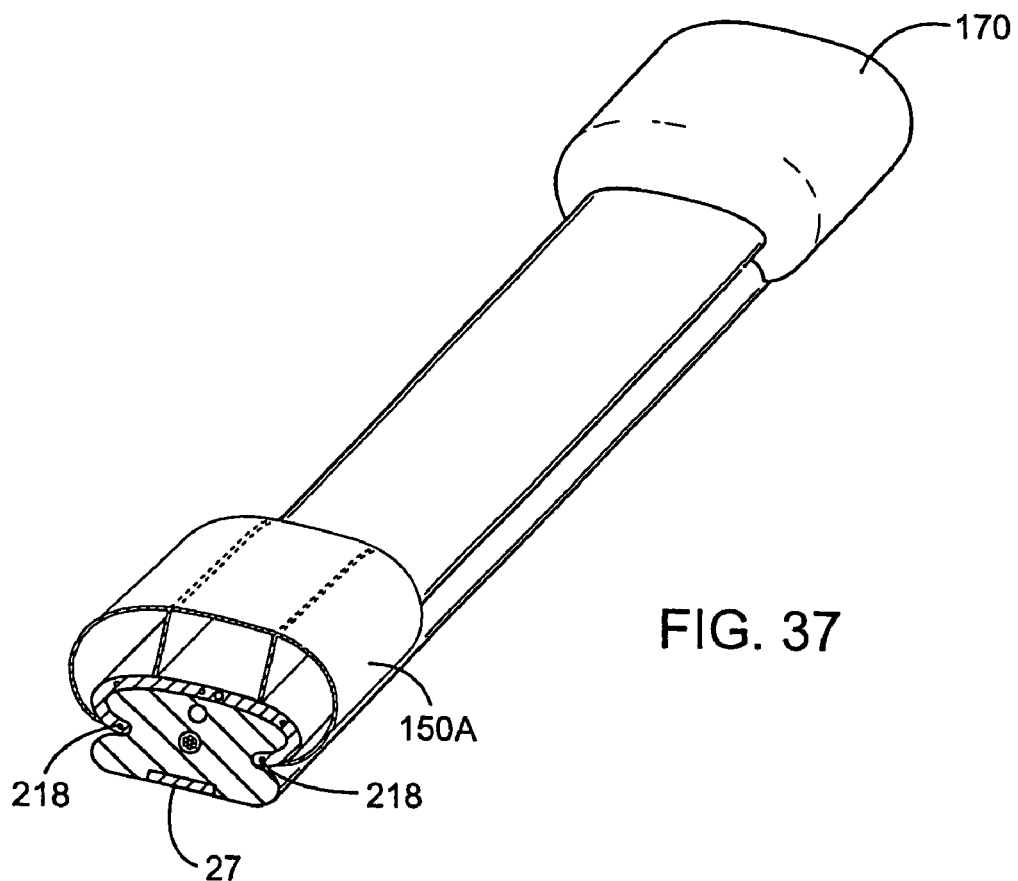

FIG. 37 is a cross-sectional view of the ablating device of FIG. 36.

Figure 38:
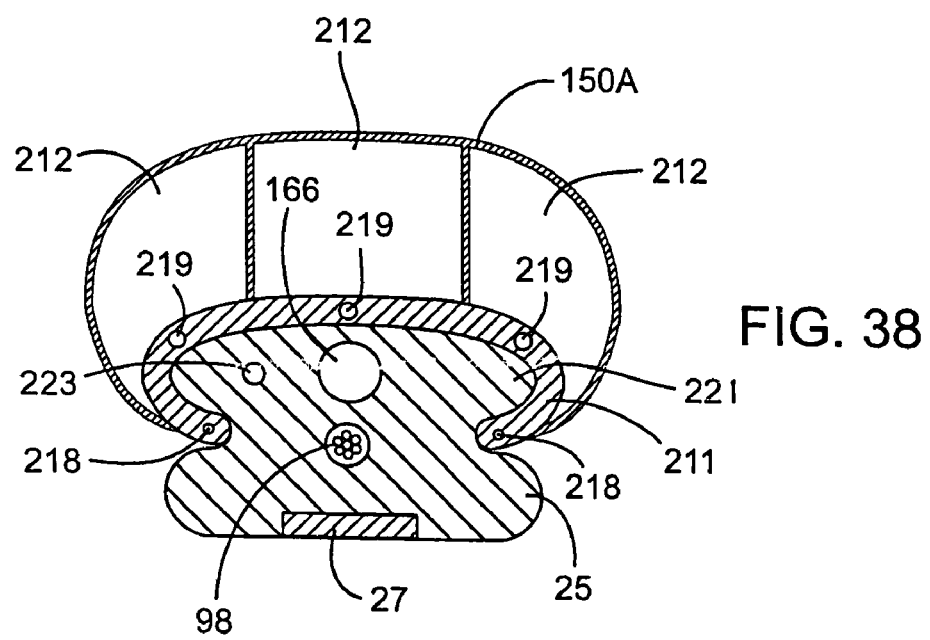

FIG. 38 is an enlarged view of the cross-sectional view of FIG. 37.

Figure 39:
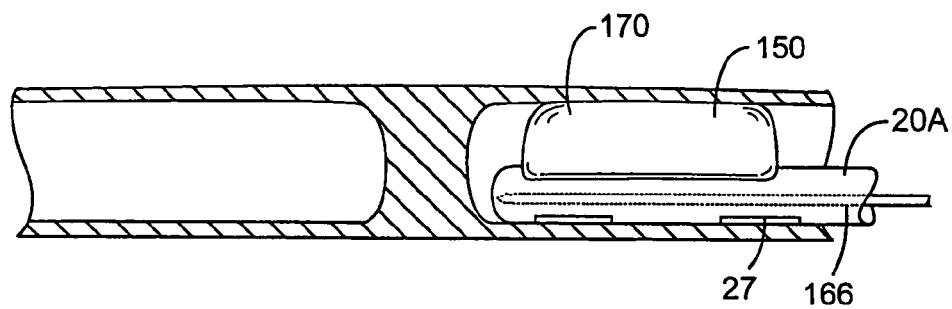

FIG. 39 shows the ablating device with a piercing element in a retracted position.

Figure 40:
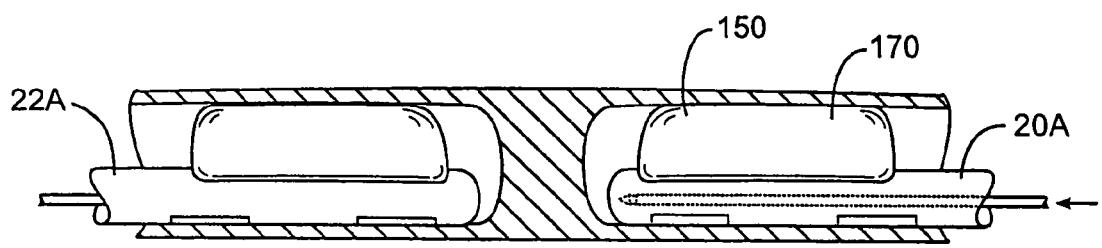

FIG. 40 shows the ablating device aligned across the pericardial reflection.

Figure 41:
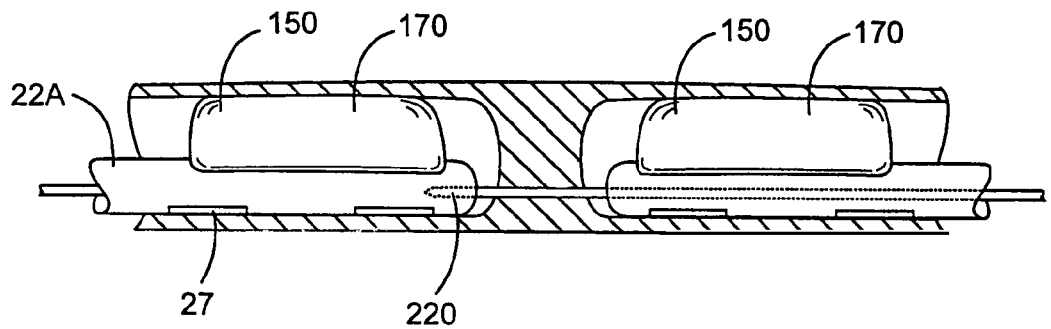

FIG. 41 shows the ablating device interlocked with another ablating device on opposite sides of the pericardial reflection.

Figure 42:
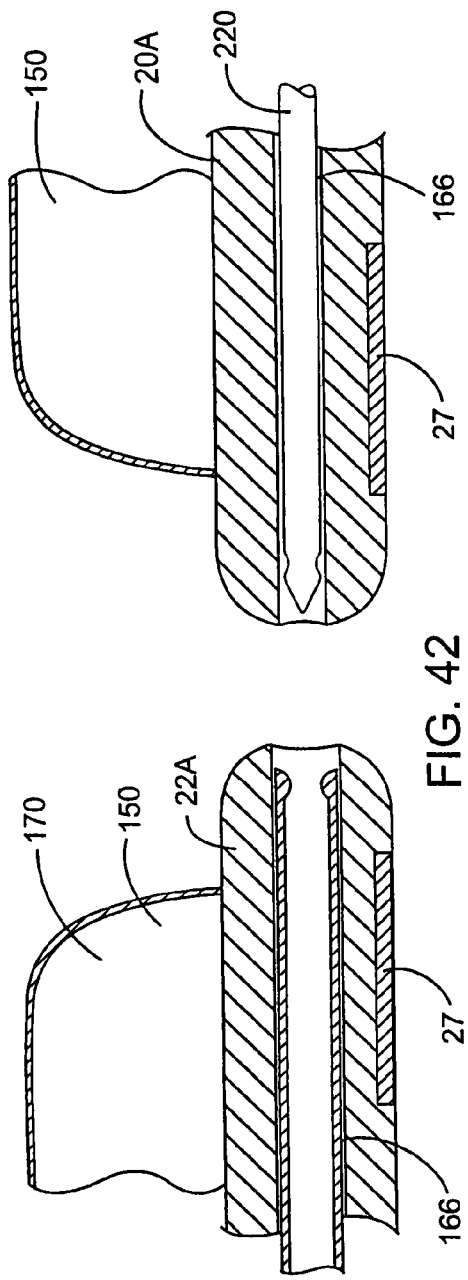

FIG. 42 shows a mechanism for locking the first and second ablating devices together.

Figure 43:
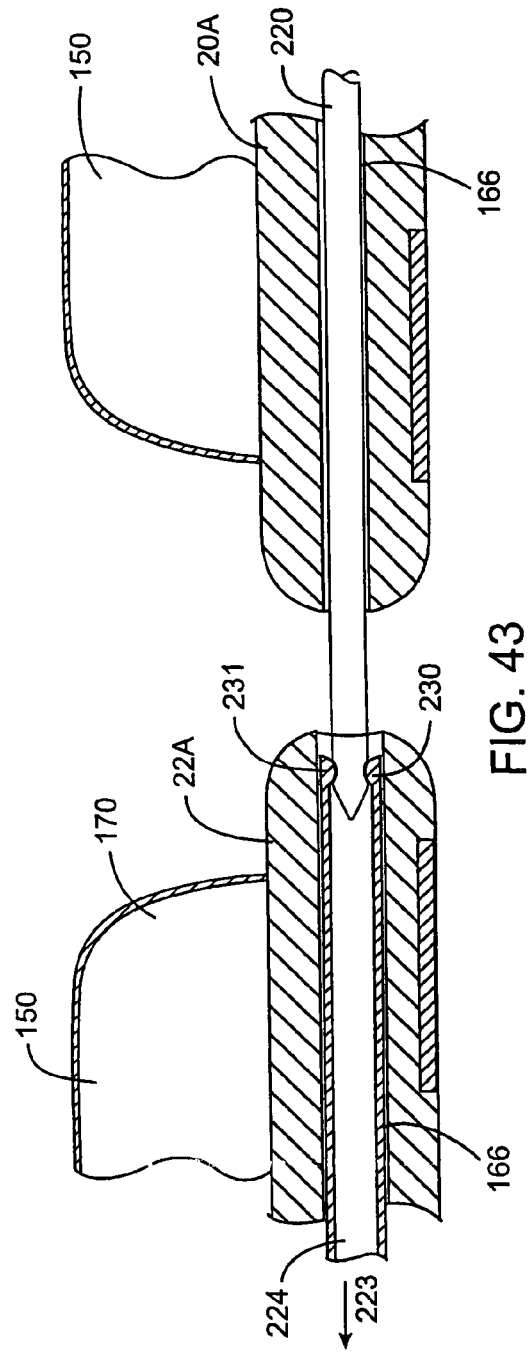

FIG. 43 shows the piercing element engaging a lock on the other ablating device.

Figure 44:
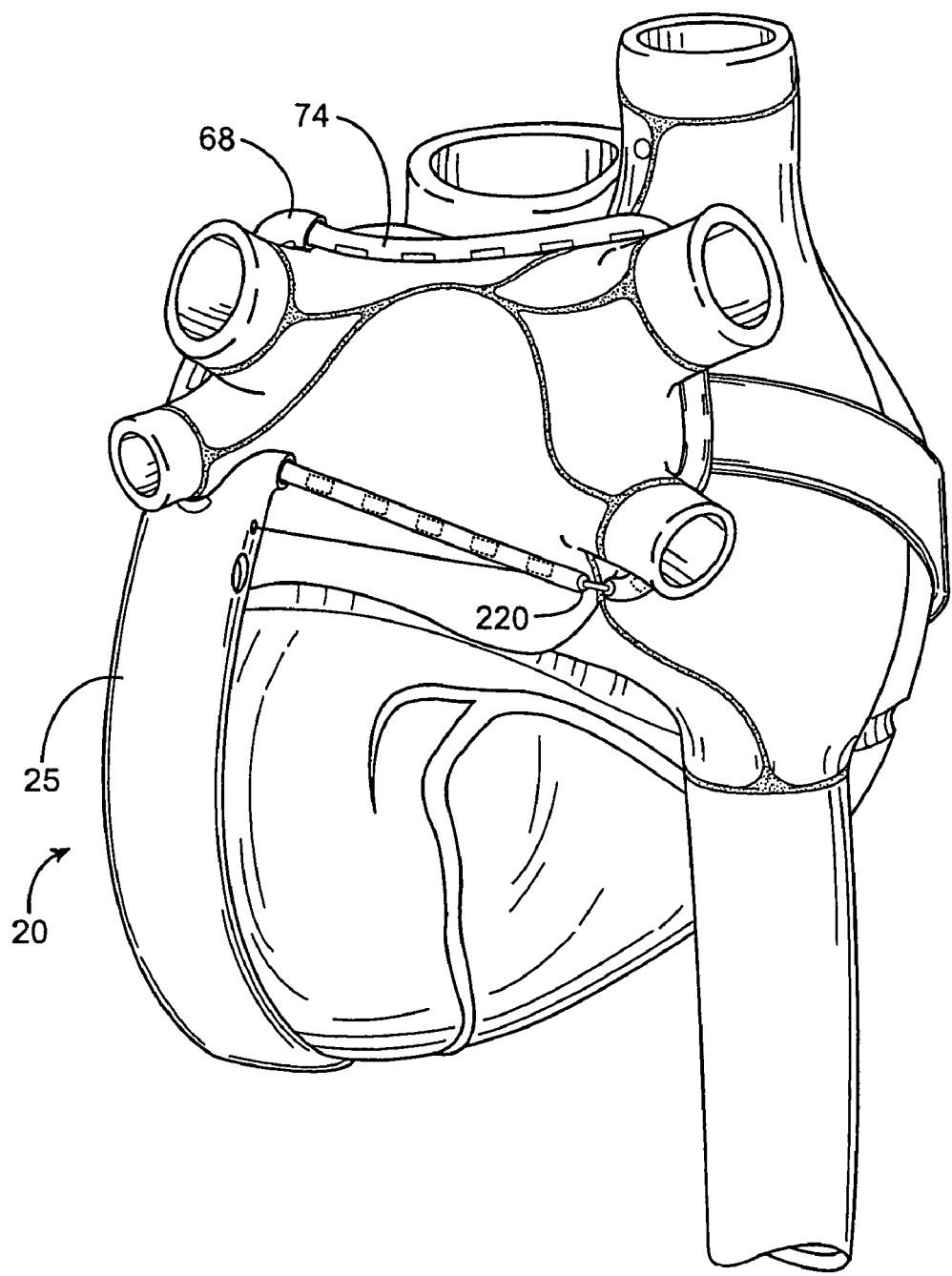

FIG. 44 shows the ablating device passing through the pericardial reflection and interlocking with itself.

Figure 45:
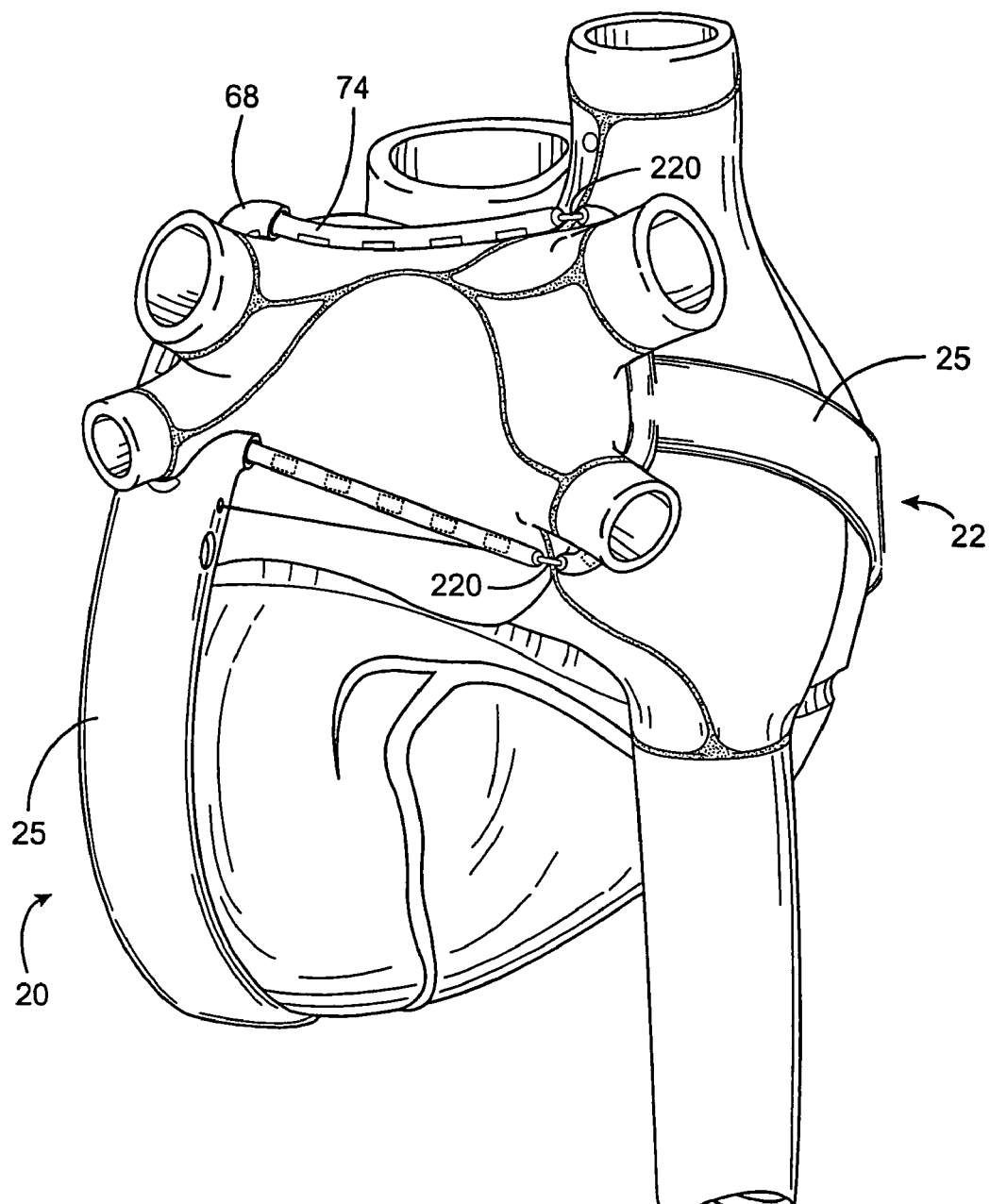

FIG. 45 shows the ablating devices interlocked across the pericardial reflections.

Figure 46:
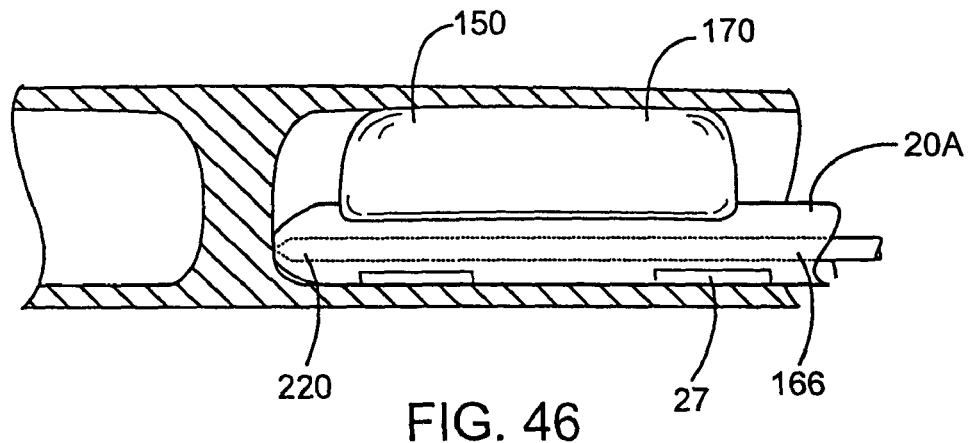

FIG. 46 shows the ablating device adhered to a pericardial reflection with suction.

Figure 47:
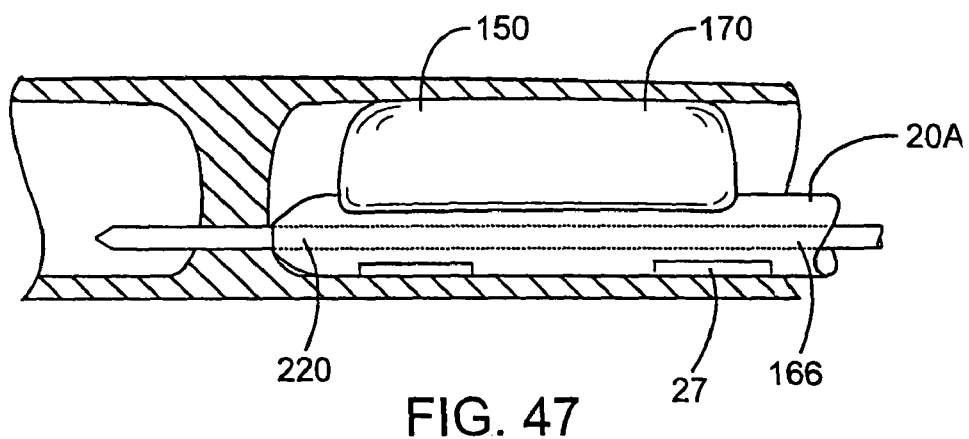

FIG. 47 shows the penetrating element penetrating the pericardial reflection.

Figure 48:
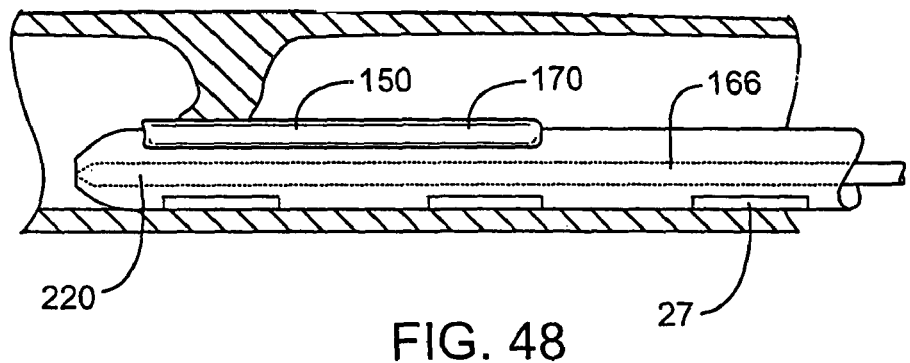

FIG. 48 shows the ablating device passing through the pericardial reflection.

Figure 49:
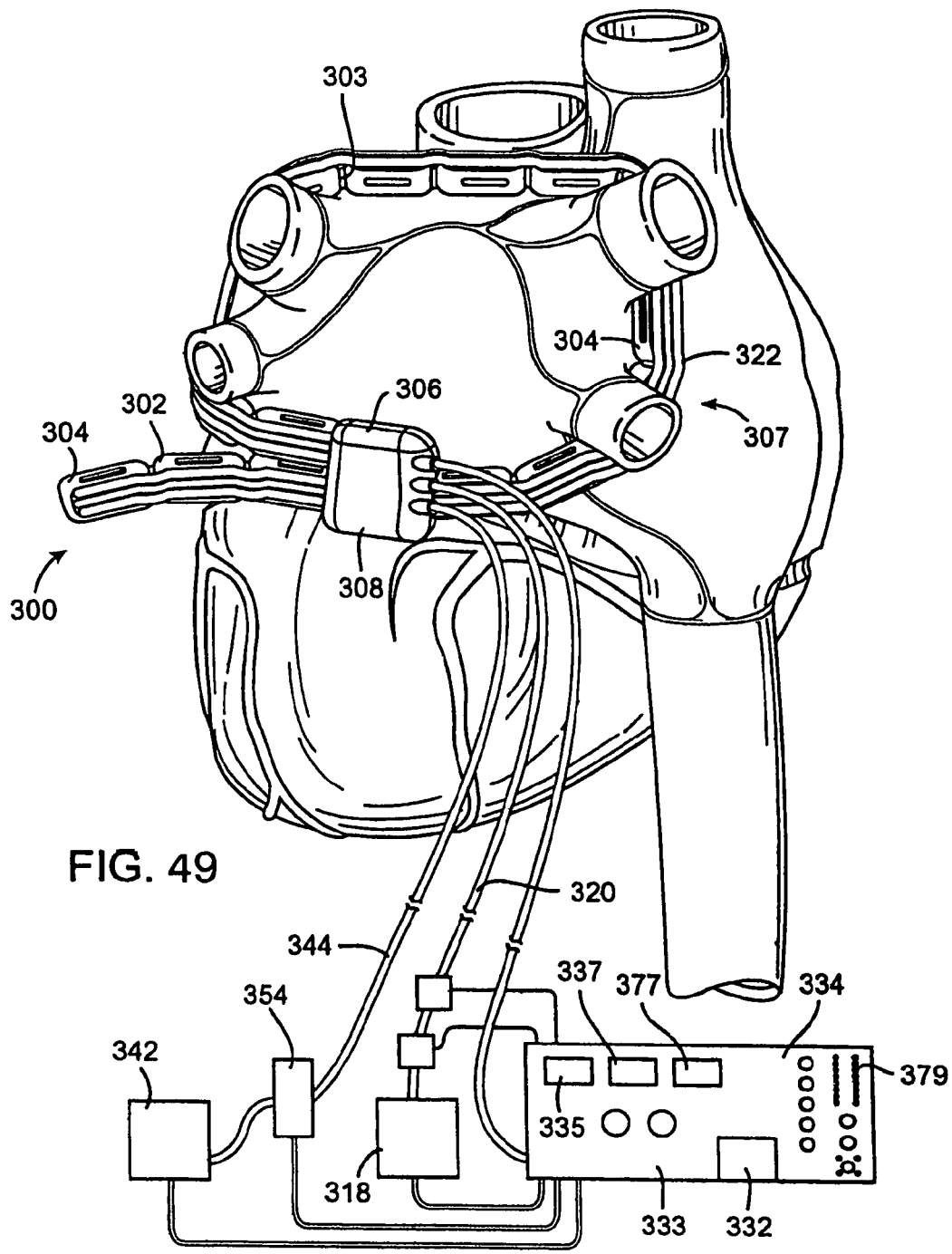

FIG. 49 shows another ablating device.

Figure 50:
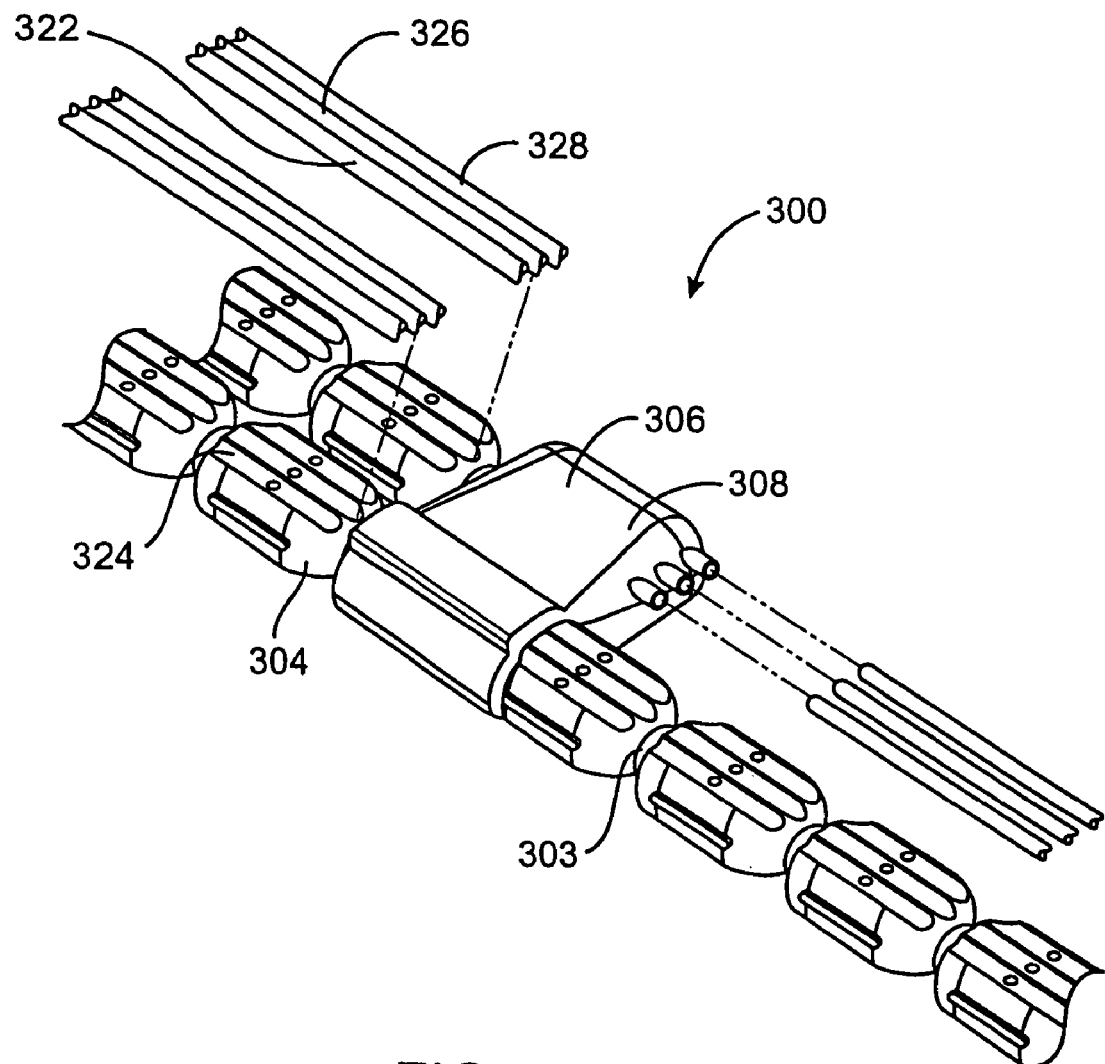

FIG. 50 shows a buckle for forming a closed loop with the ablating device.

Figure 51:
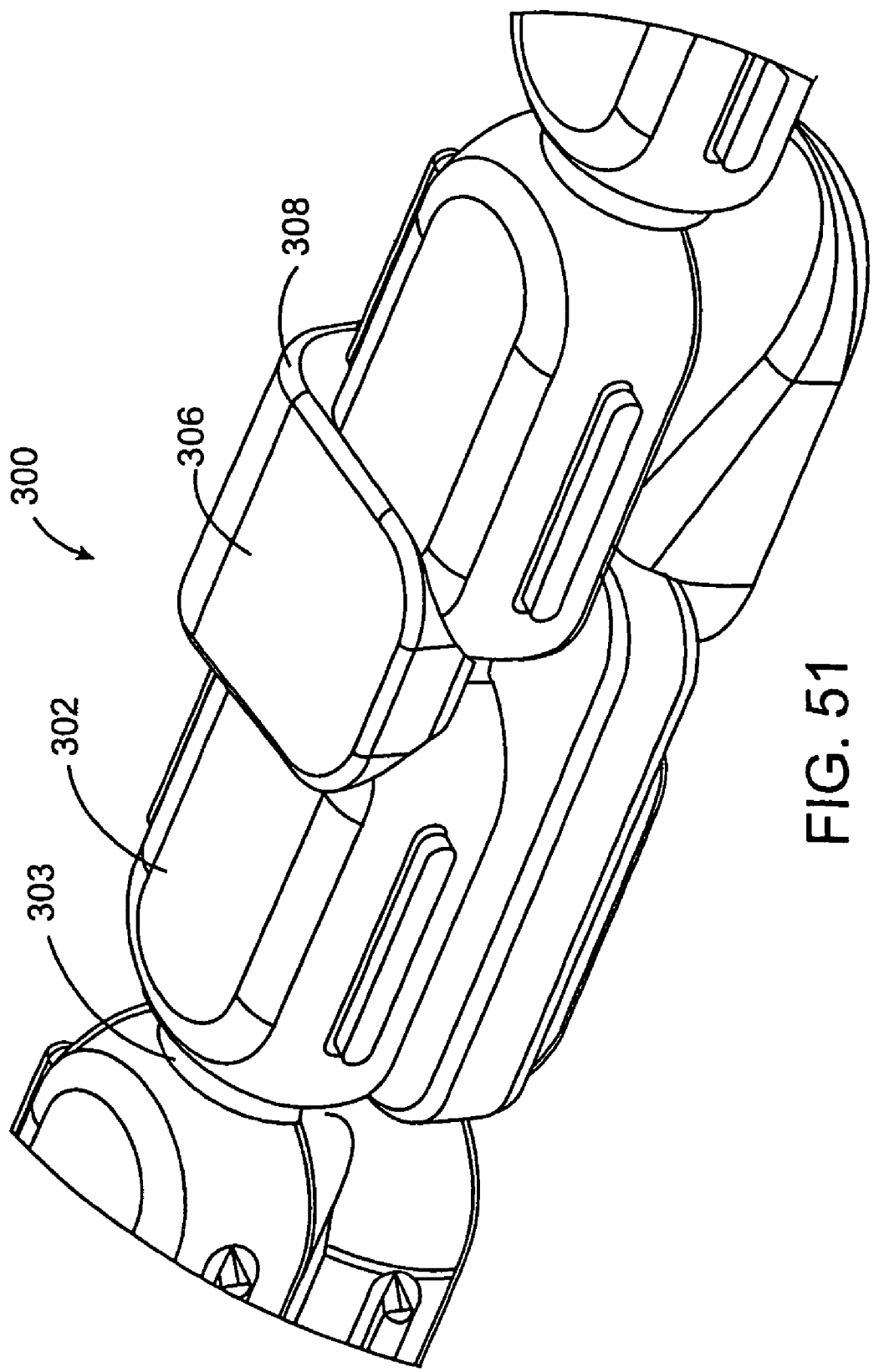

FIG. 51 shows another buckle for forming the closed loop with the ablating device.

Figure 52:
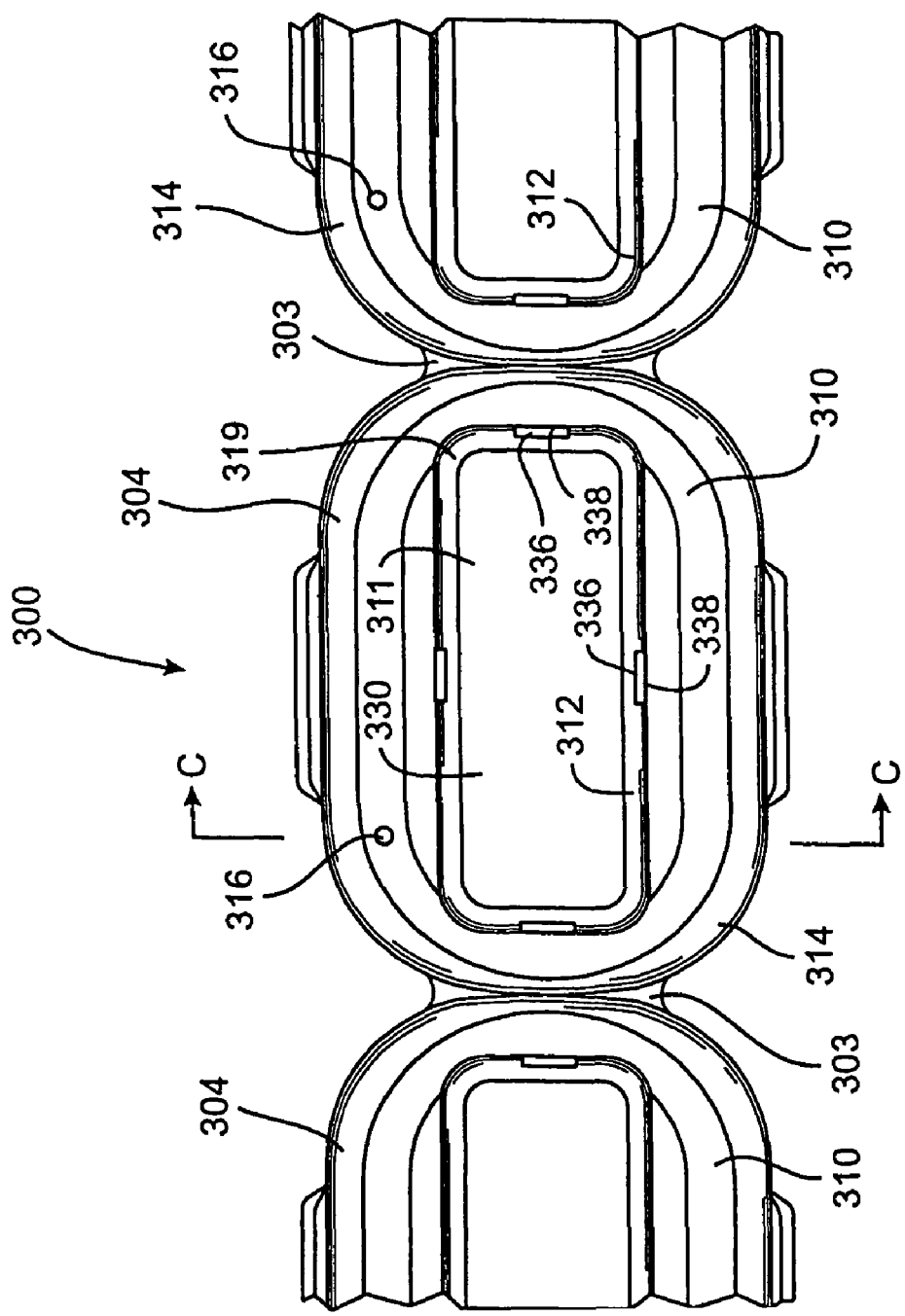

FIG. 52 shows a bottom side of the ablating device of FIG. 49.

Figure 53A:
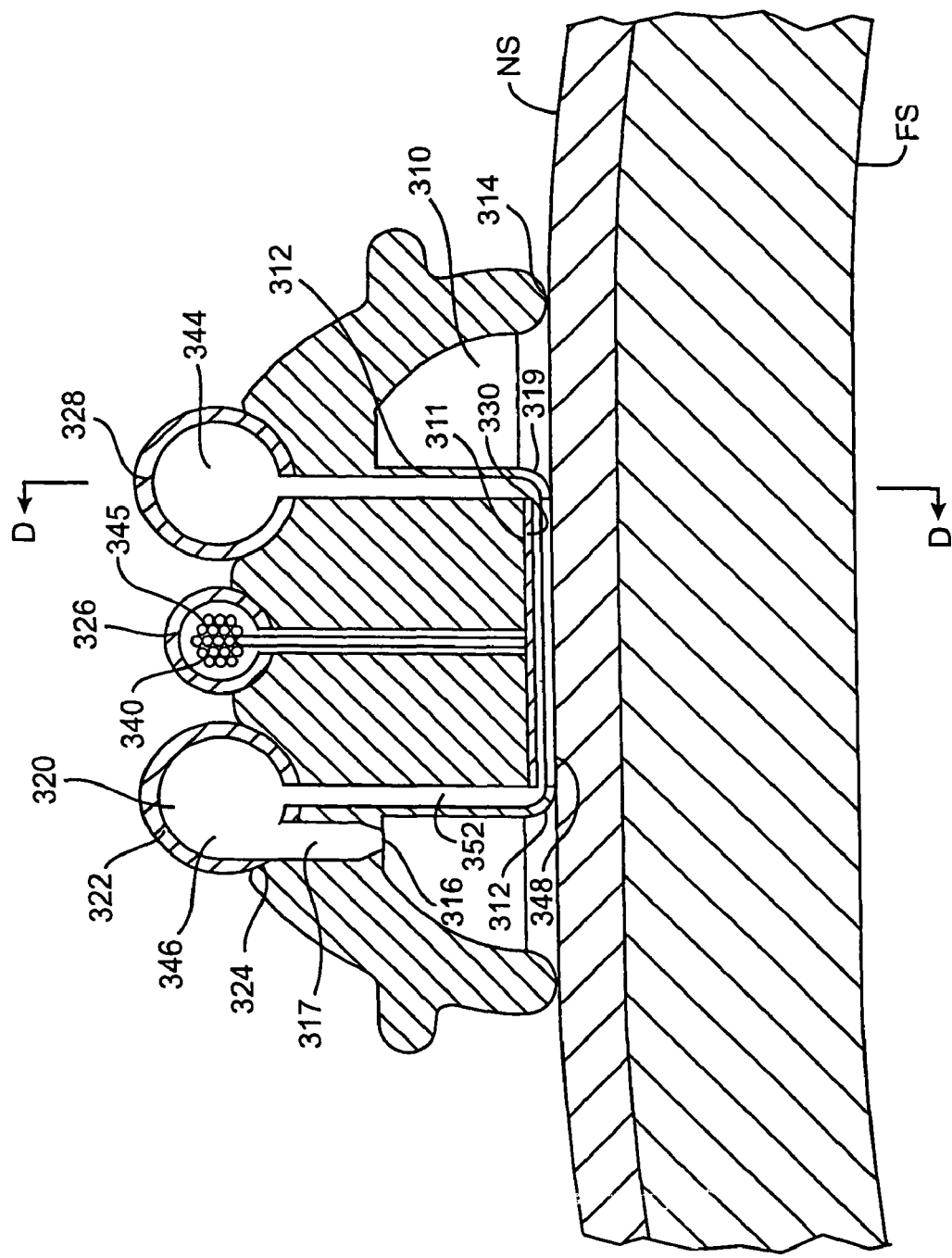

FIG. 53A is a cross-sectional view of the ablating device along line C-C of FIG. 52.

Figure 53B:
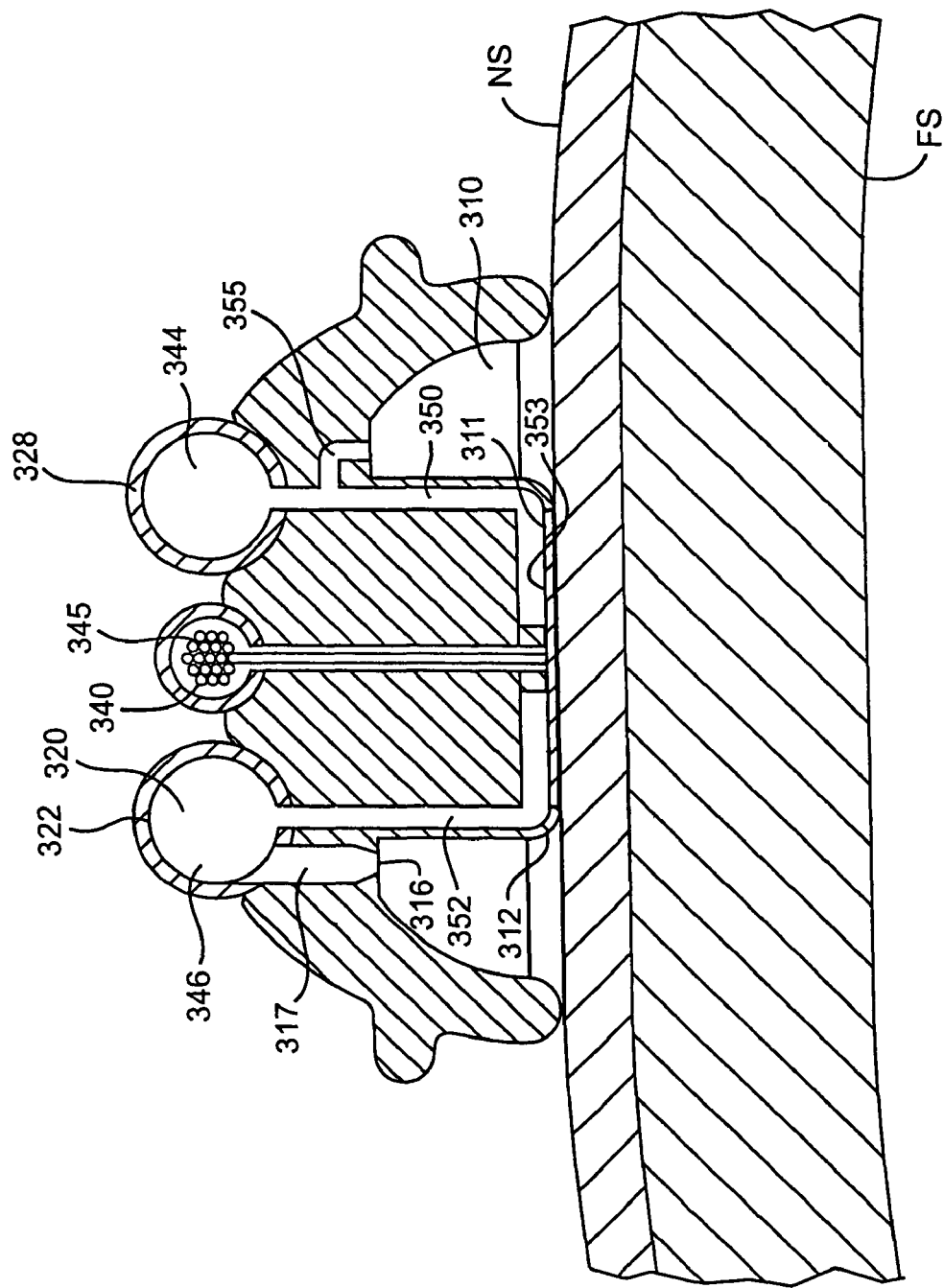

FIG. 53B is an alternative cross-sectional view of the ablating device along line C-C of FIG. 52.

Figure 54:
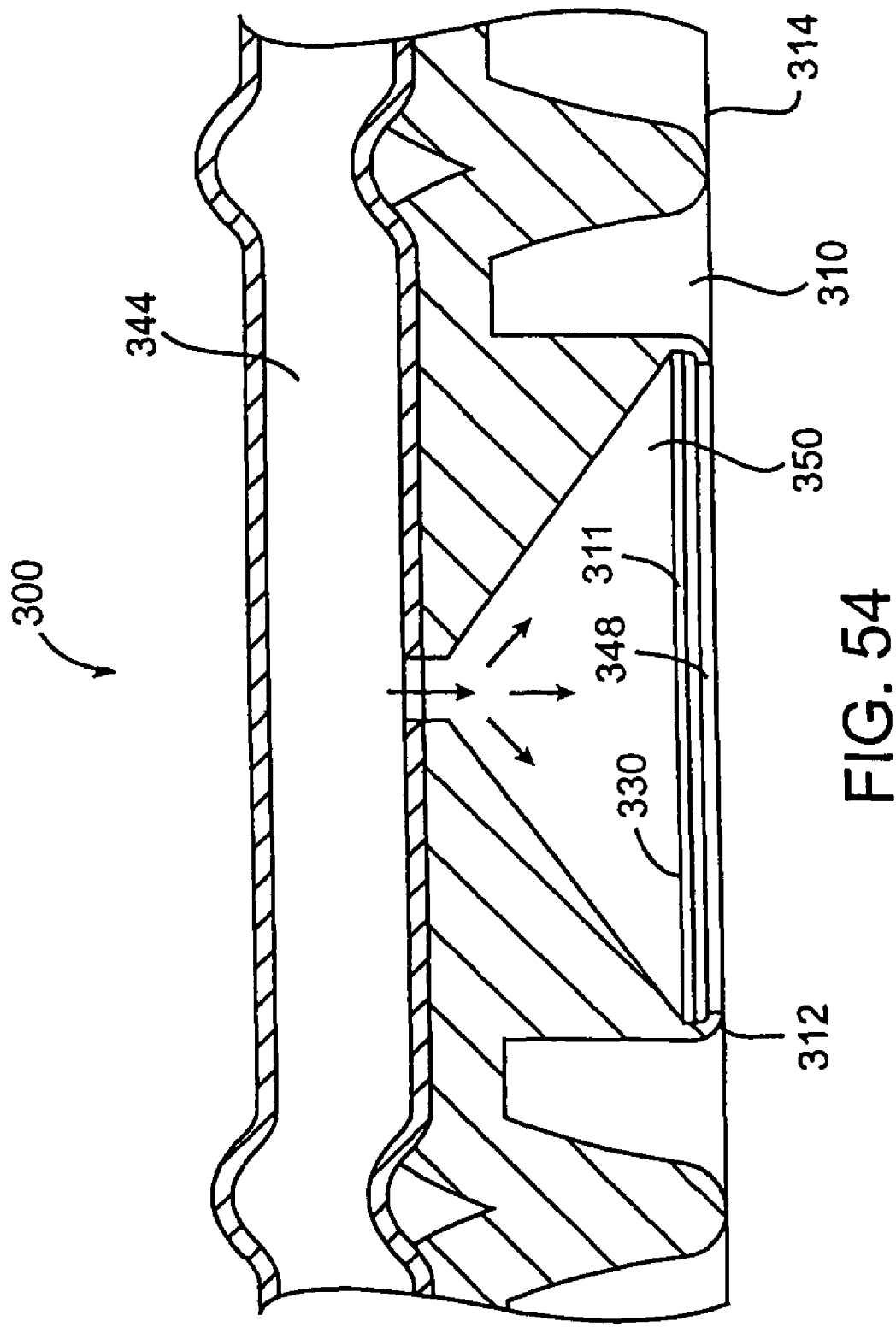

FIG. 54 is a cross-sectional view of the ablation device along line D-D of FIG. 53A showing a fluid inlet manifold.

Figure 55:
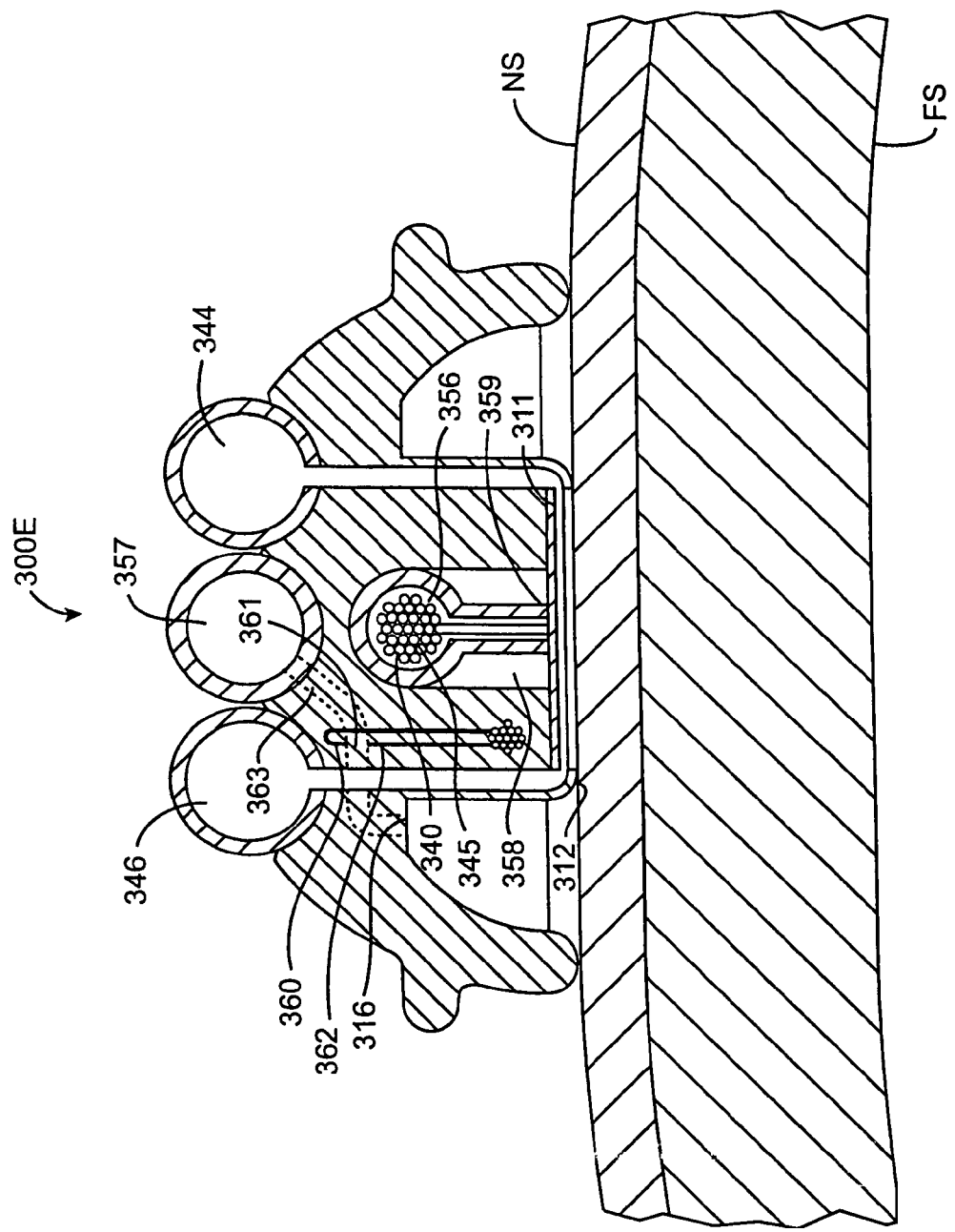

FIG. 55 is a cross-sectional view of an alternative embodiment of the device.

Figure 56:
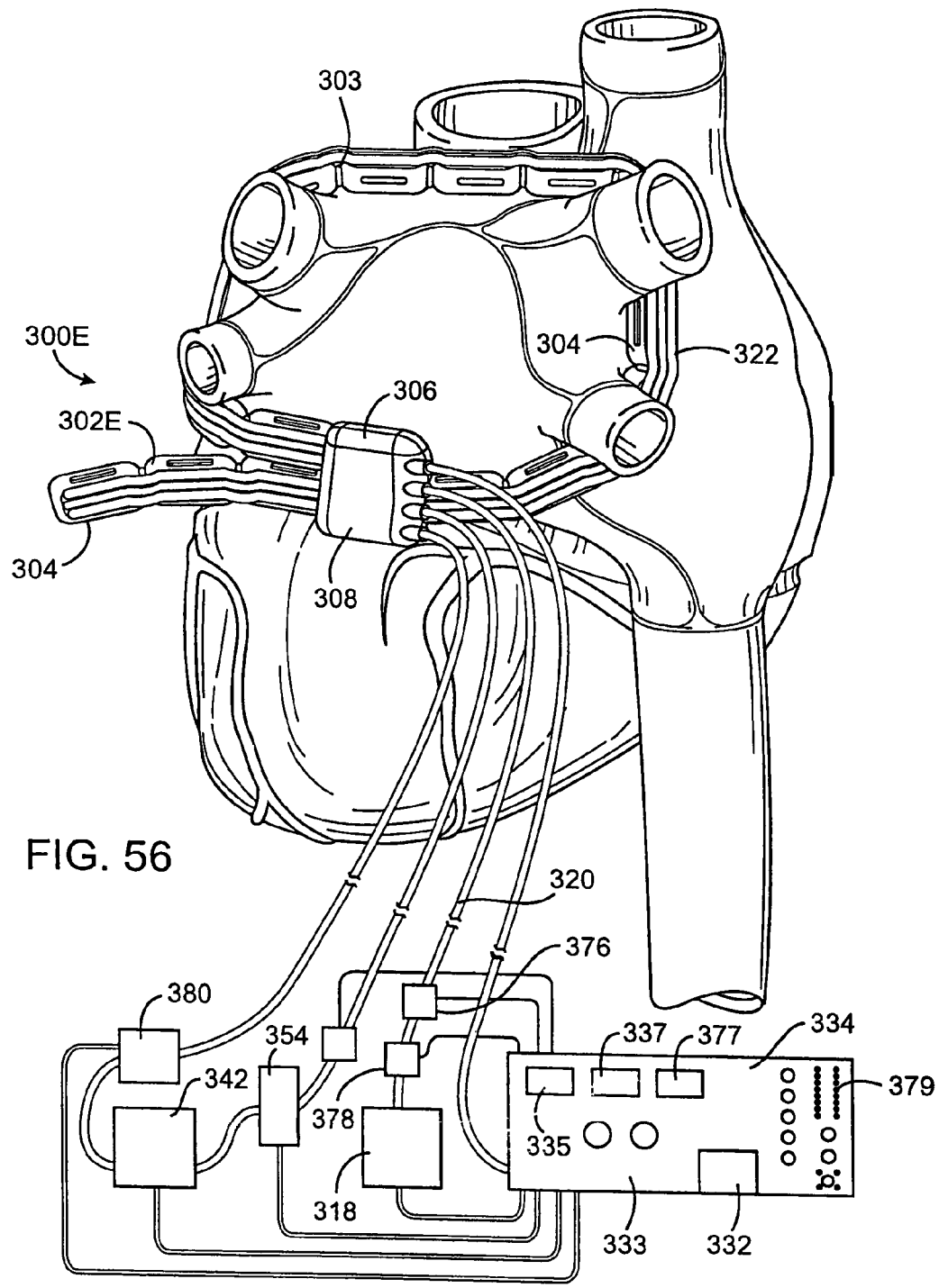

FIG. 56 shows a system for controlling the ablation device of FIG. 55.

Figure 57:
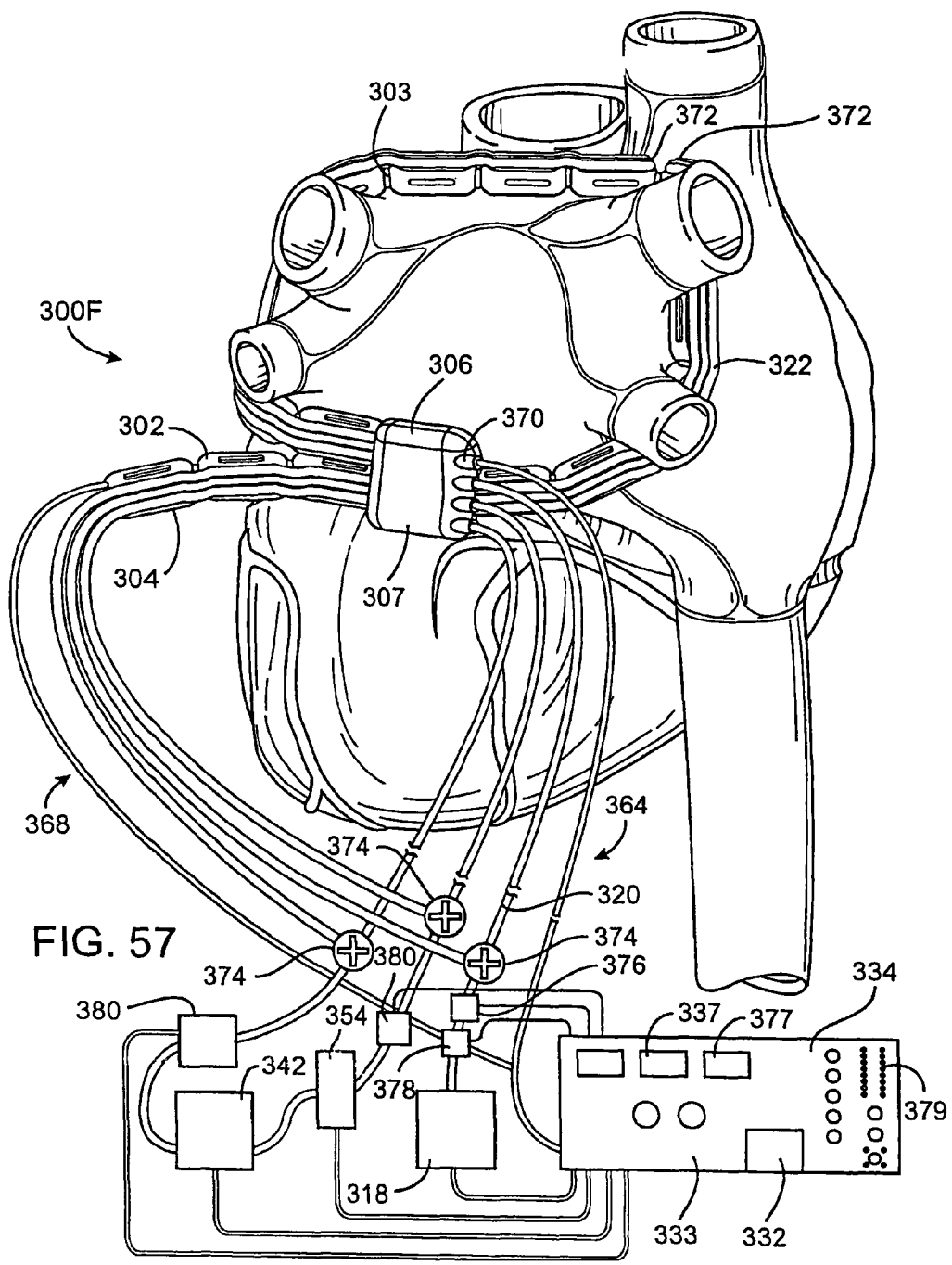

FIG. 57 shows the device having two sets of lumens extending from each end of the device toward the middle of the device.

Figure 58:
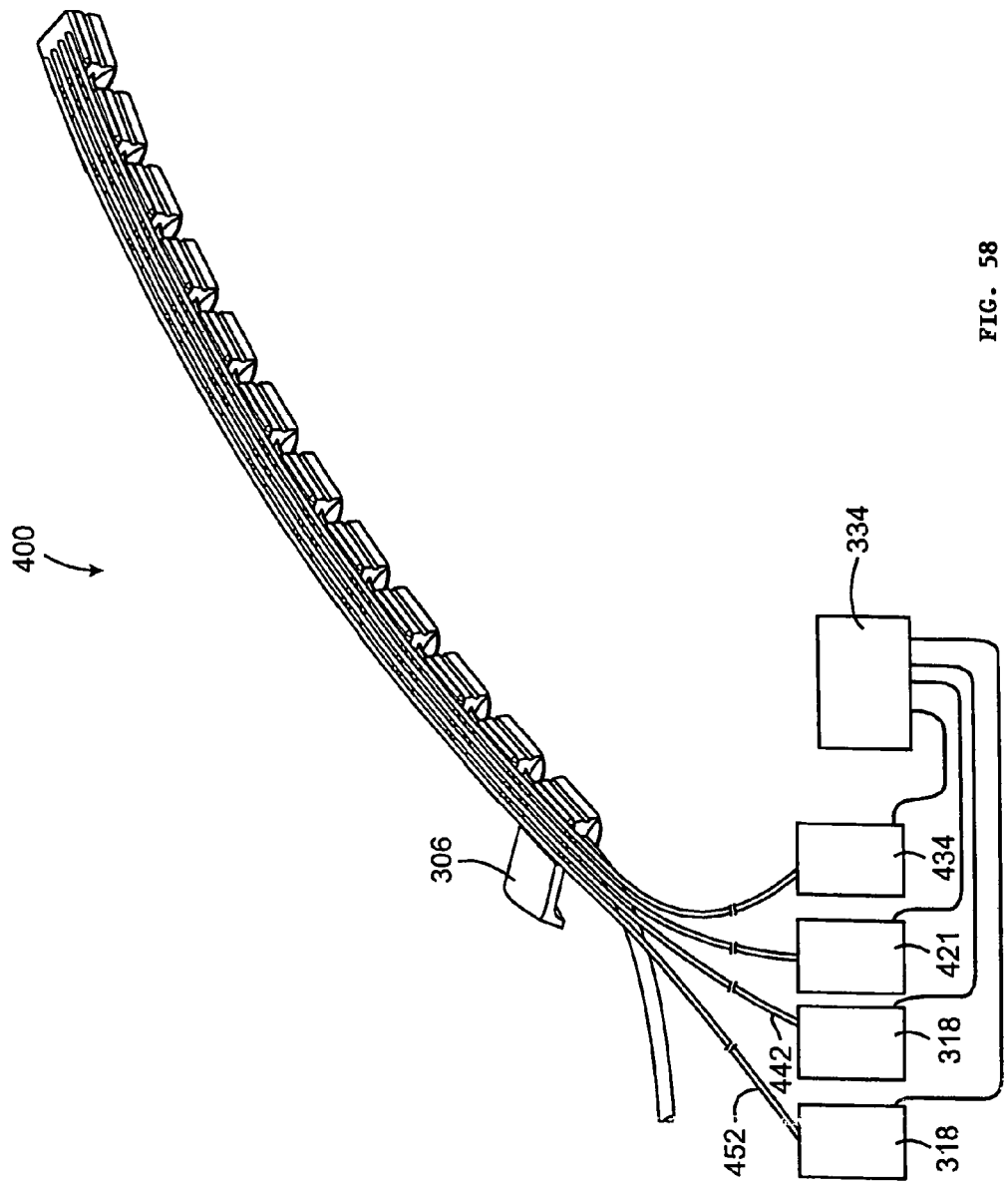

FIG. 58 shows another ablating device.

Figure 59:
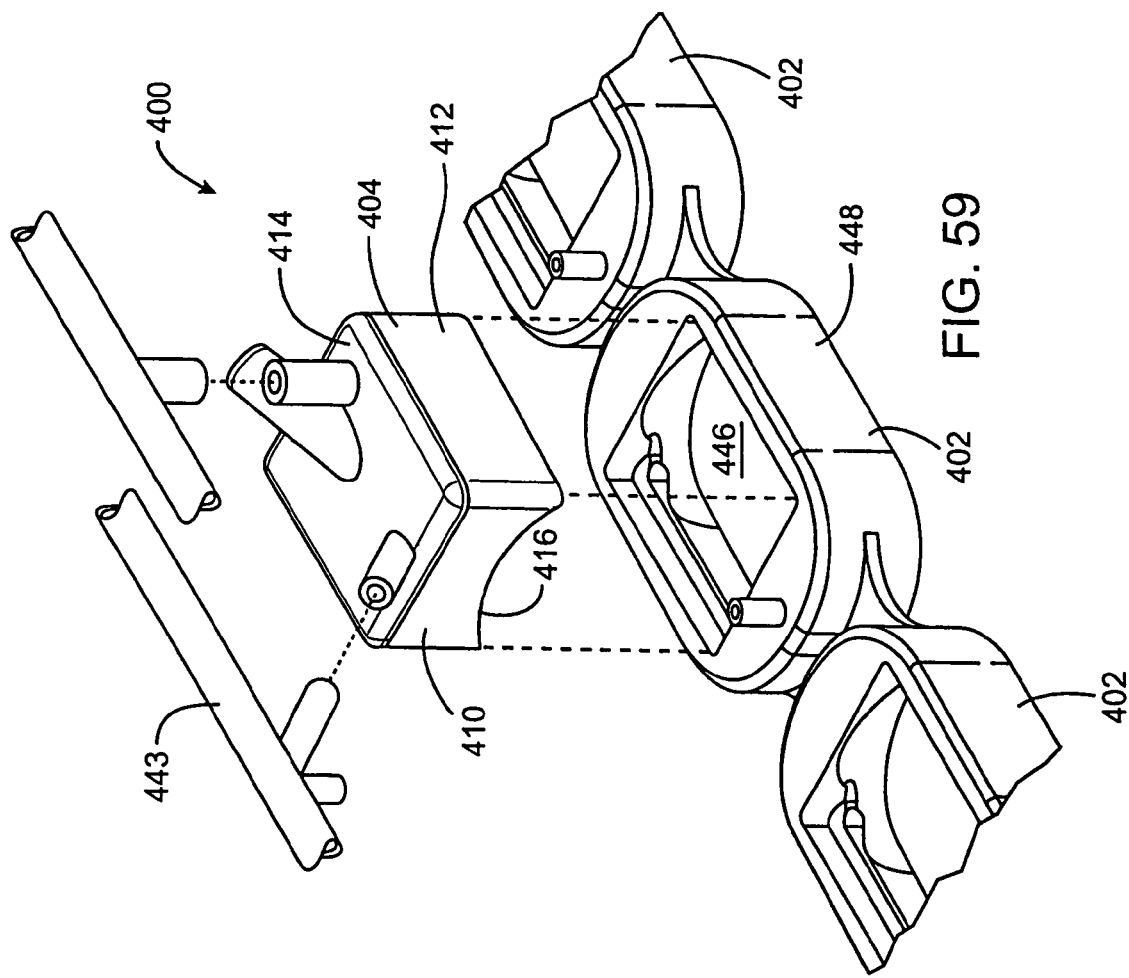

FIG. 59 is an exploded view of a cell of the ablating device.

Figure 60:
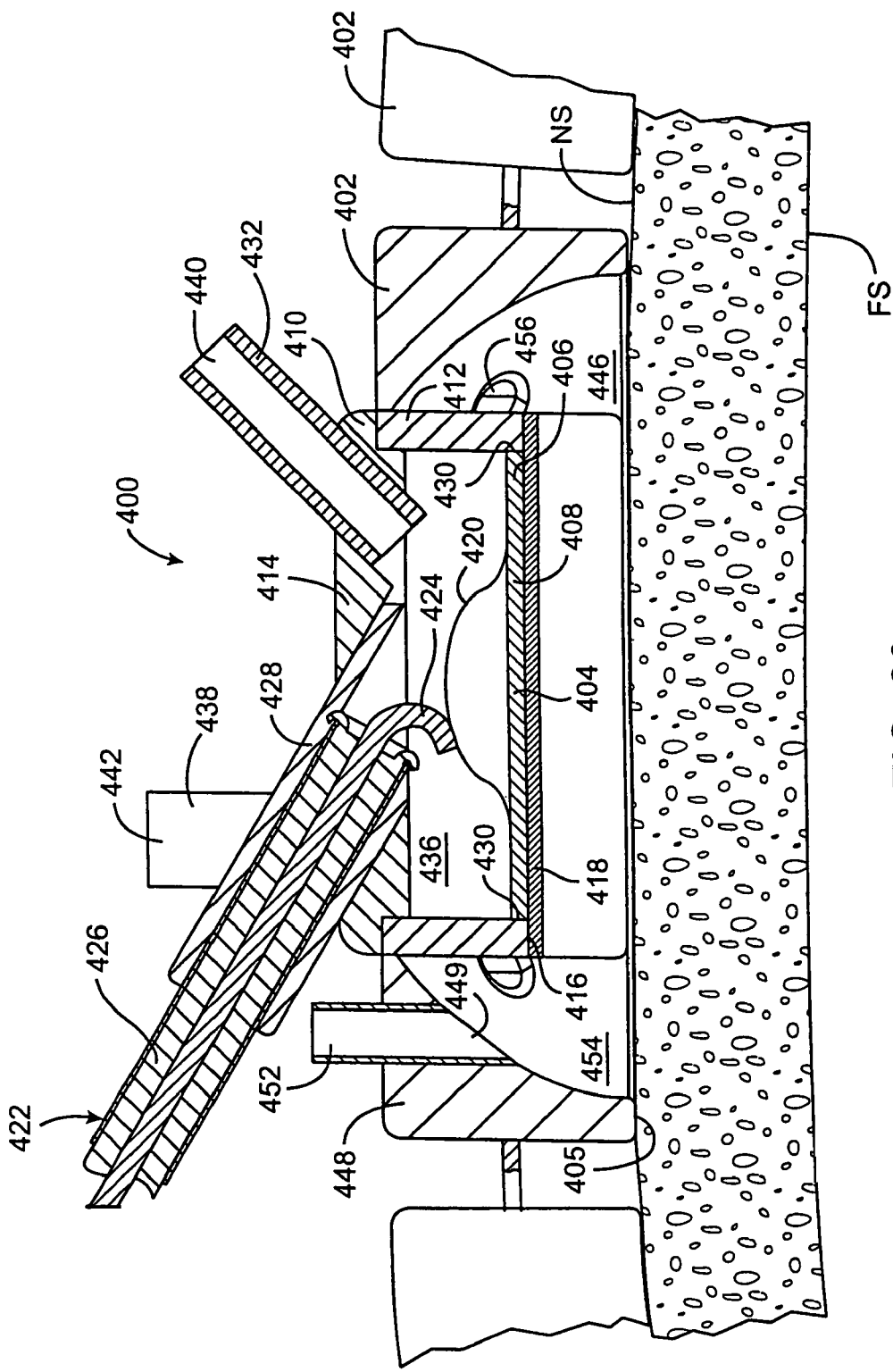

FIG. 60 is a cross-sectional view of the ablating device of FIG. 60.

Figure 61:
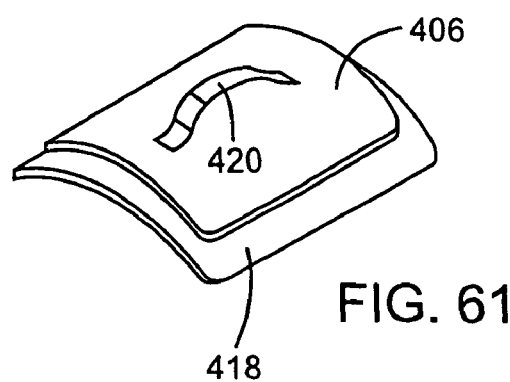

FIG. 61 is a perspective view of a transducer with a layer attached thereto.

Figure 62:
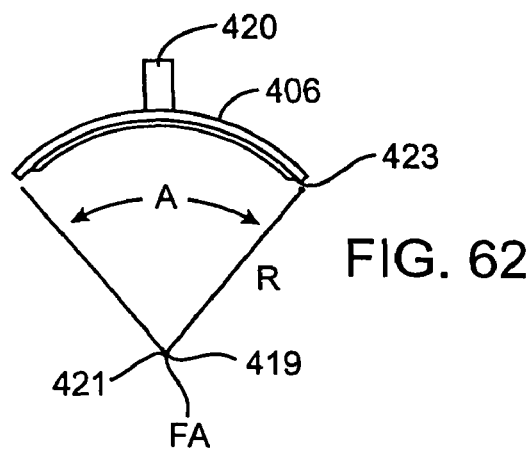

FIG. 62 is an end view of the transducer and layer.

Figure 63:
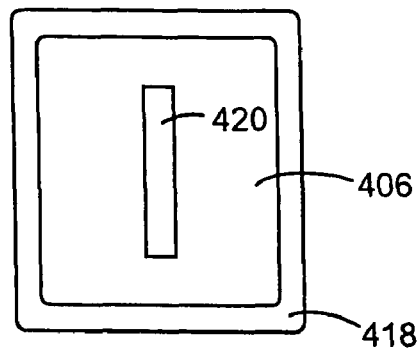

FIG. 63 is a plan view of the transducer and layer.

Figure 64:
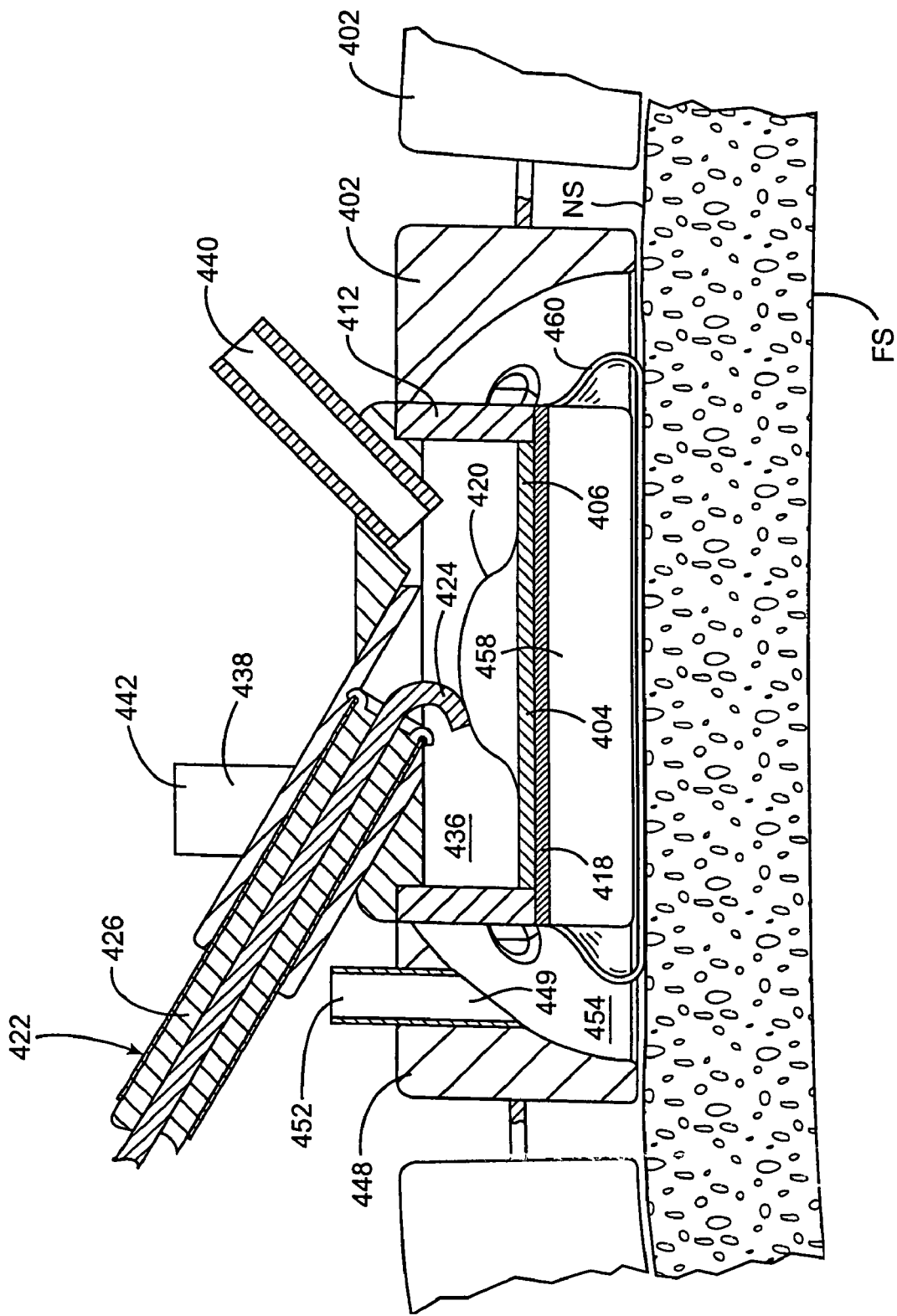

FIG. 64 shows another ablating device with a membrane filled with a substance with transmits energy from the transducer to the tissue.

Figure 65:
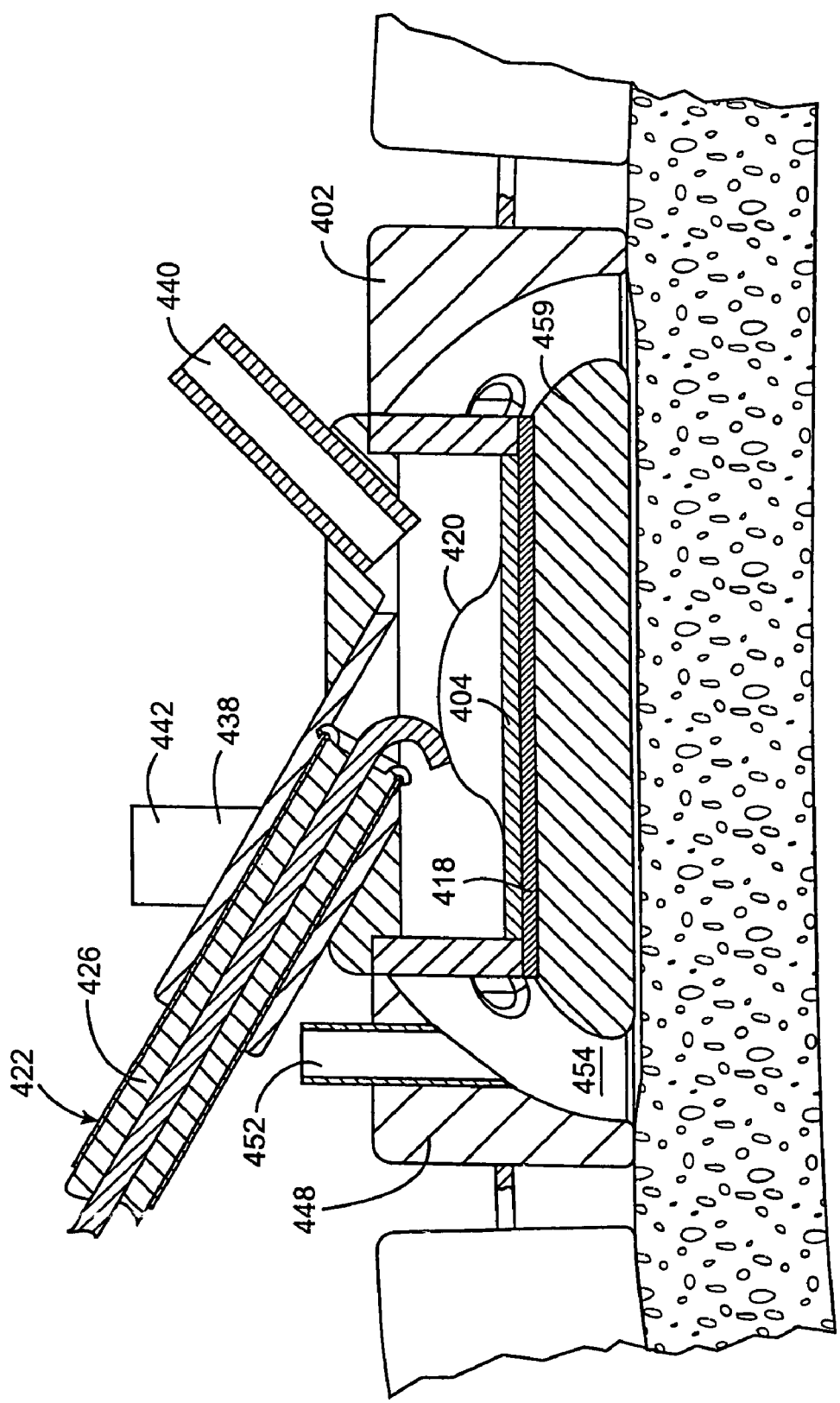

FIG. 65 shows the membrane inflated to move the focus relative to the tissue.

Figure 66:
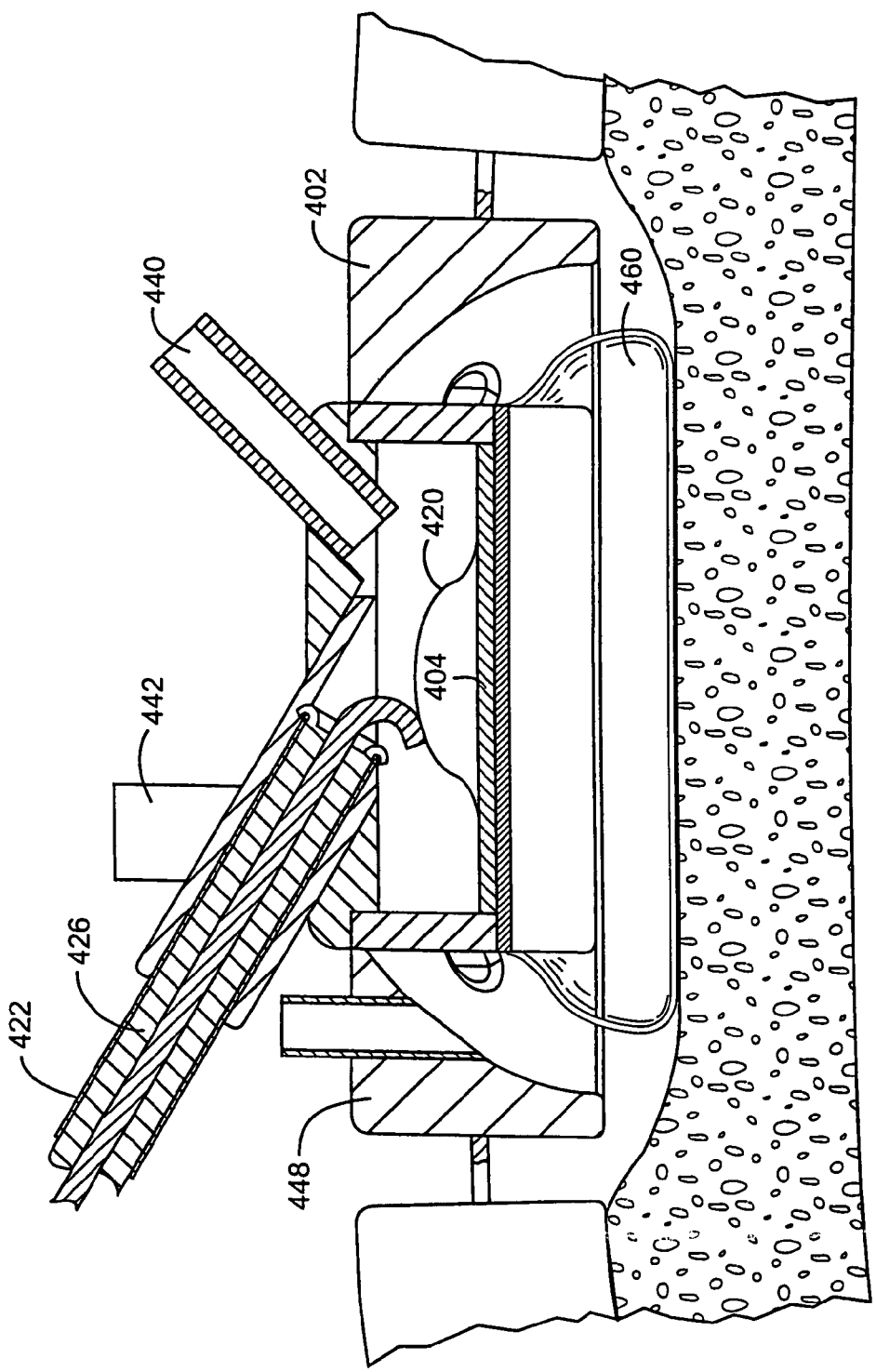

FIG. 66 shows another ablating device with a membrane which tilts the device when inflated.

Figure 67:
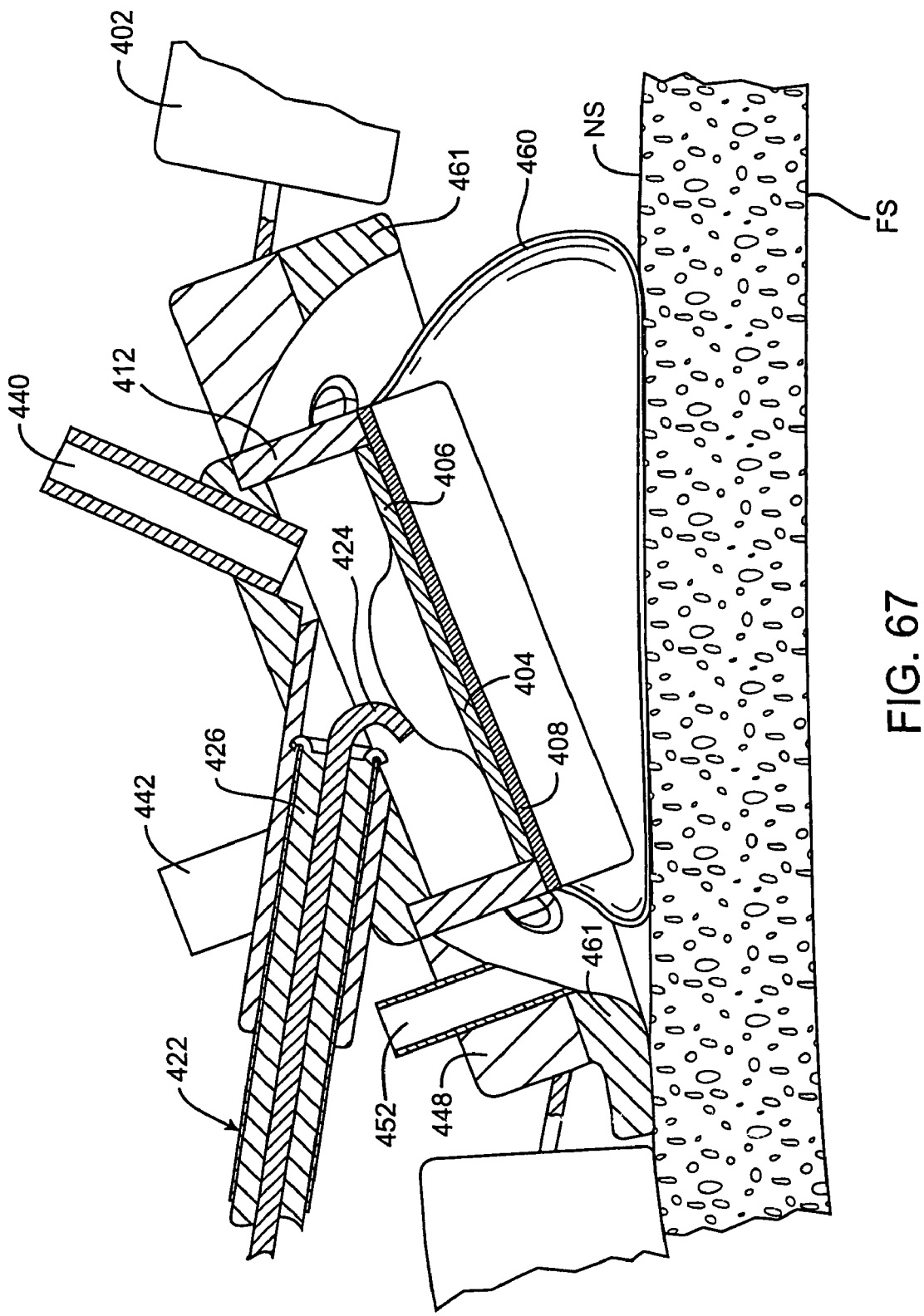

FIG. 67 shows another ablating device.

Figure 68:
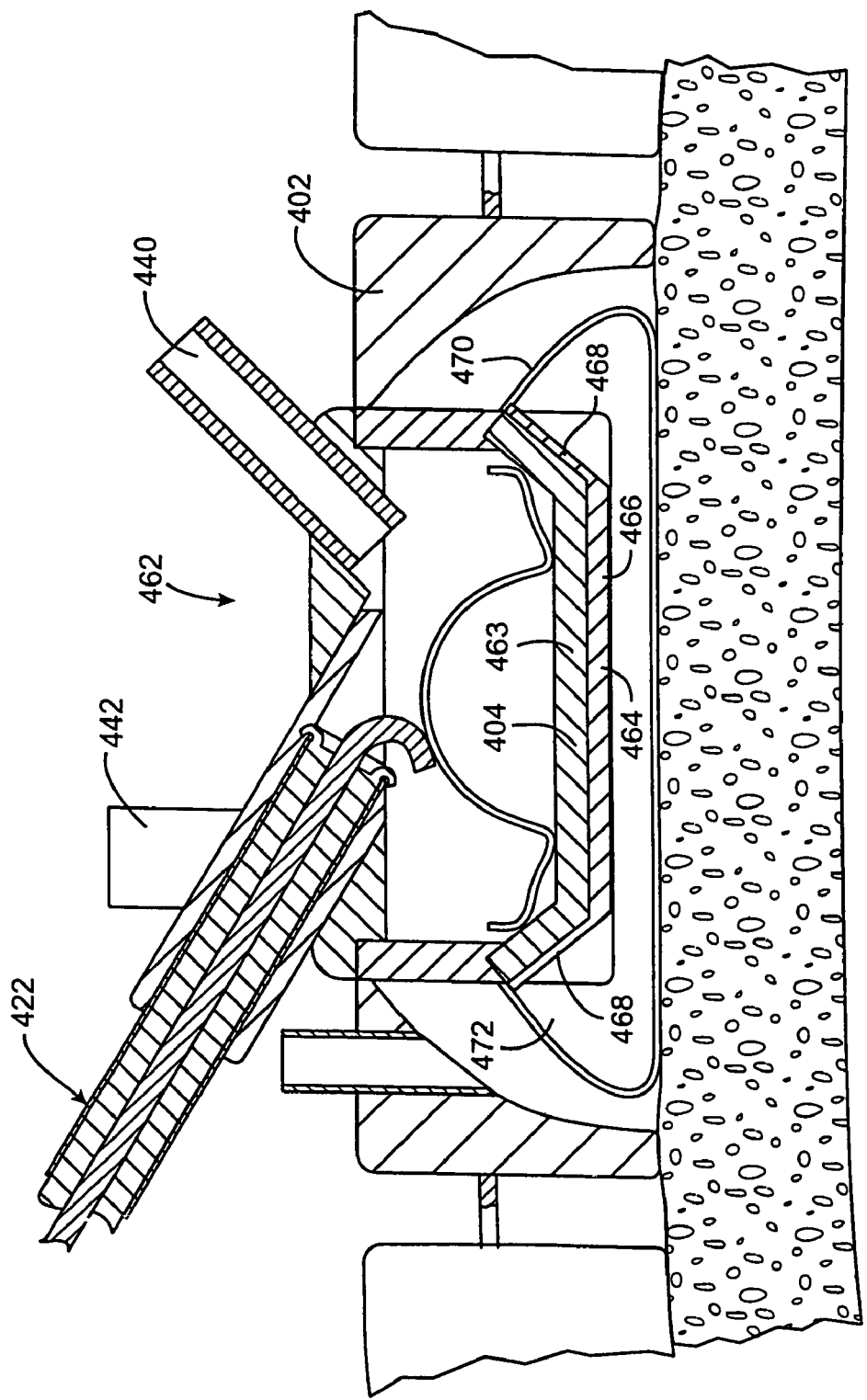

FIG. 68 shows still another ablating device having at least two ablating elements which have different ablating characteristics.

Figure 69:
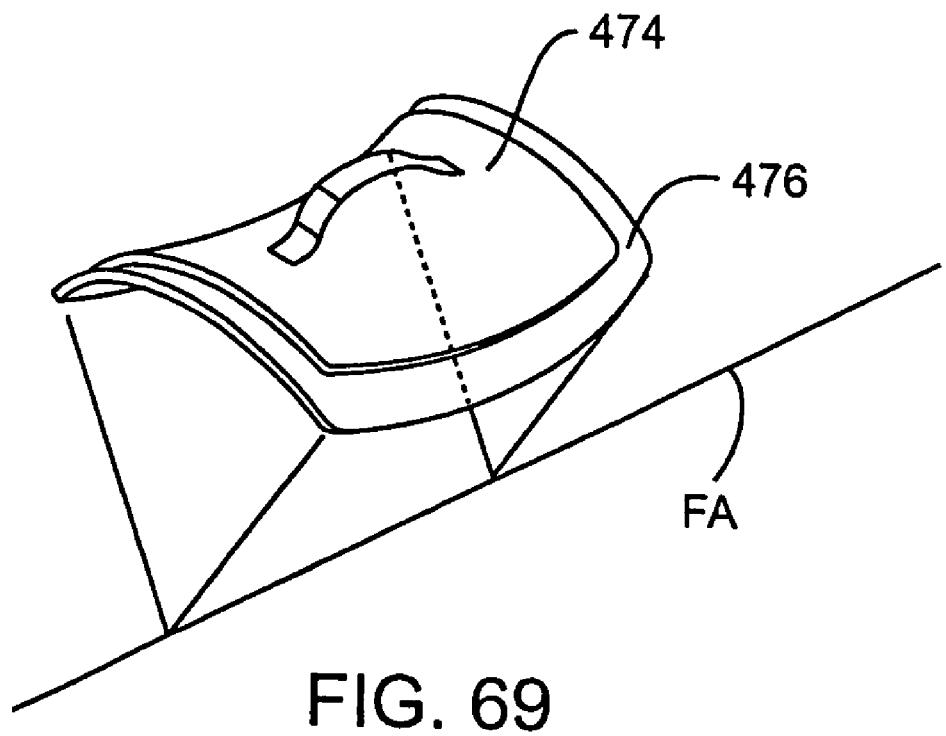

FIG. 69 is an isometric view of another ablating element which diverges in at least one dimension to ablate tissue beneath gaps between ablating elements.

Figure 70:
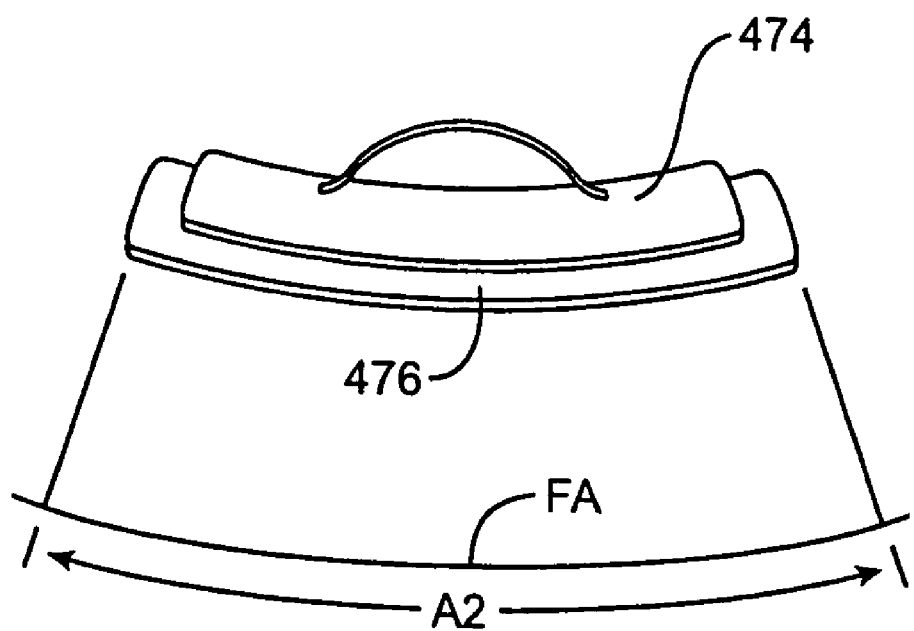

FIG. 70 is a side view of the ablating element of FIG. 69.

Figure 71:
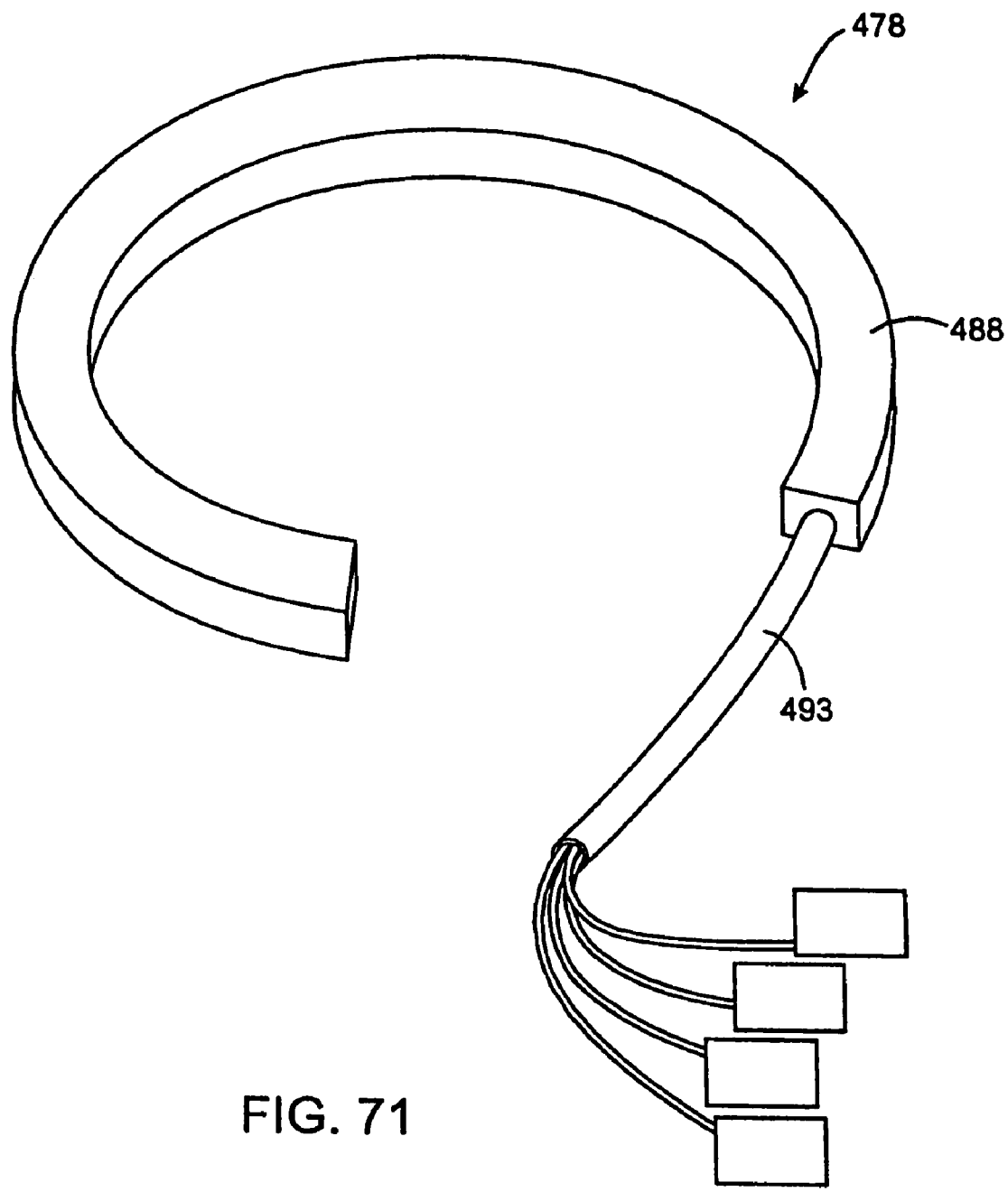

FIG. 71 shows still another device for ablating tissue.

Figure 72:
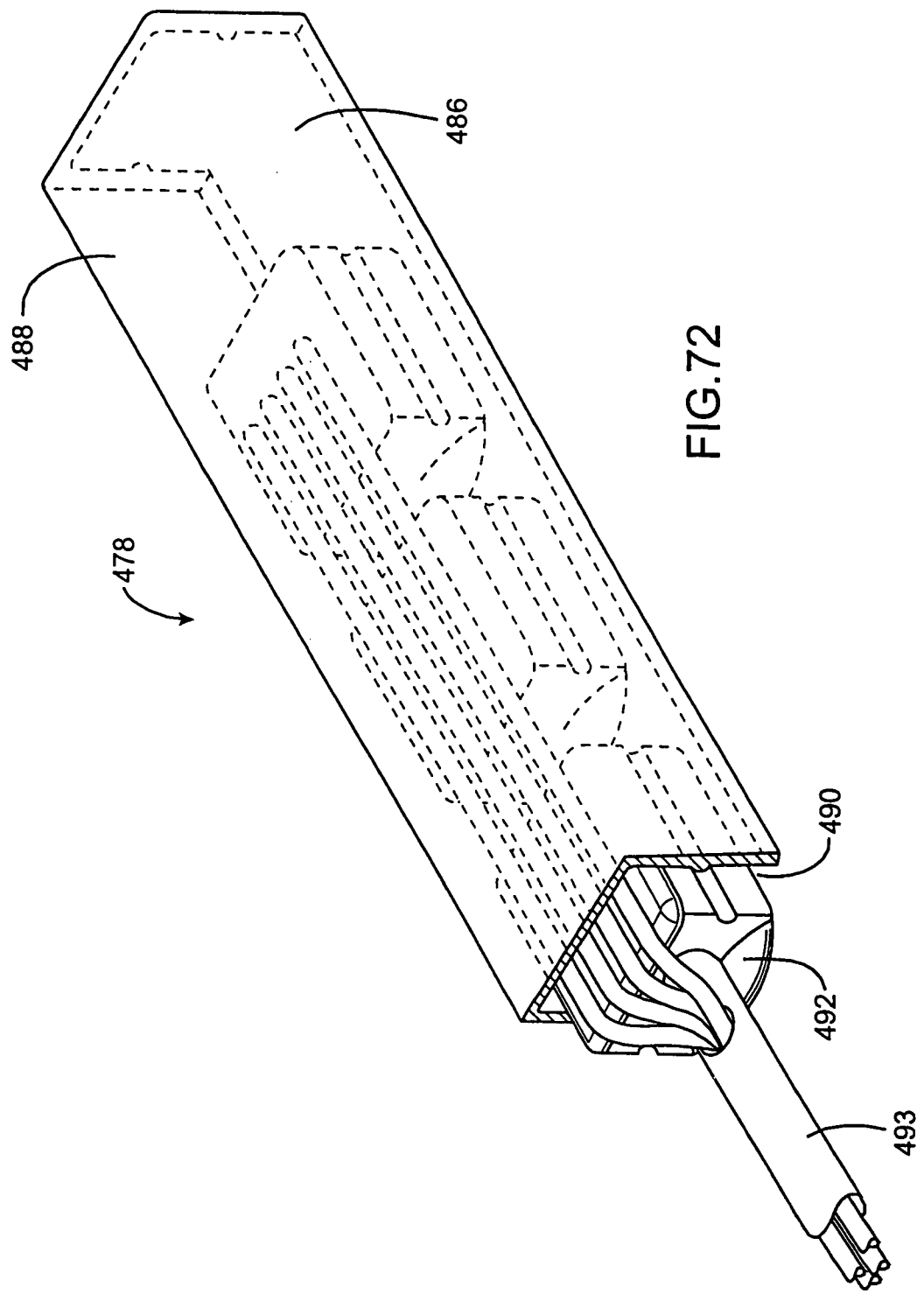

FIG. 72 is a partial cross-sectional view showing three ablating elements which are movable within a body of the device.

Figure 73:
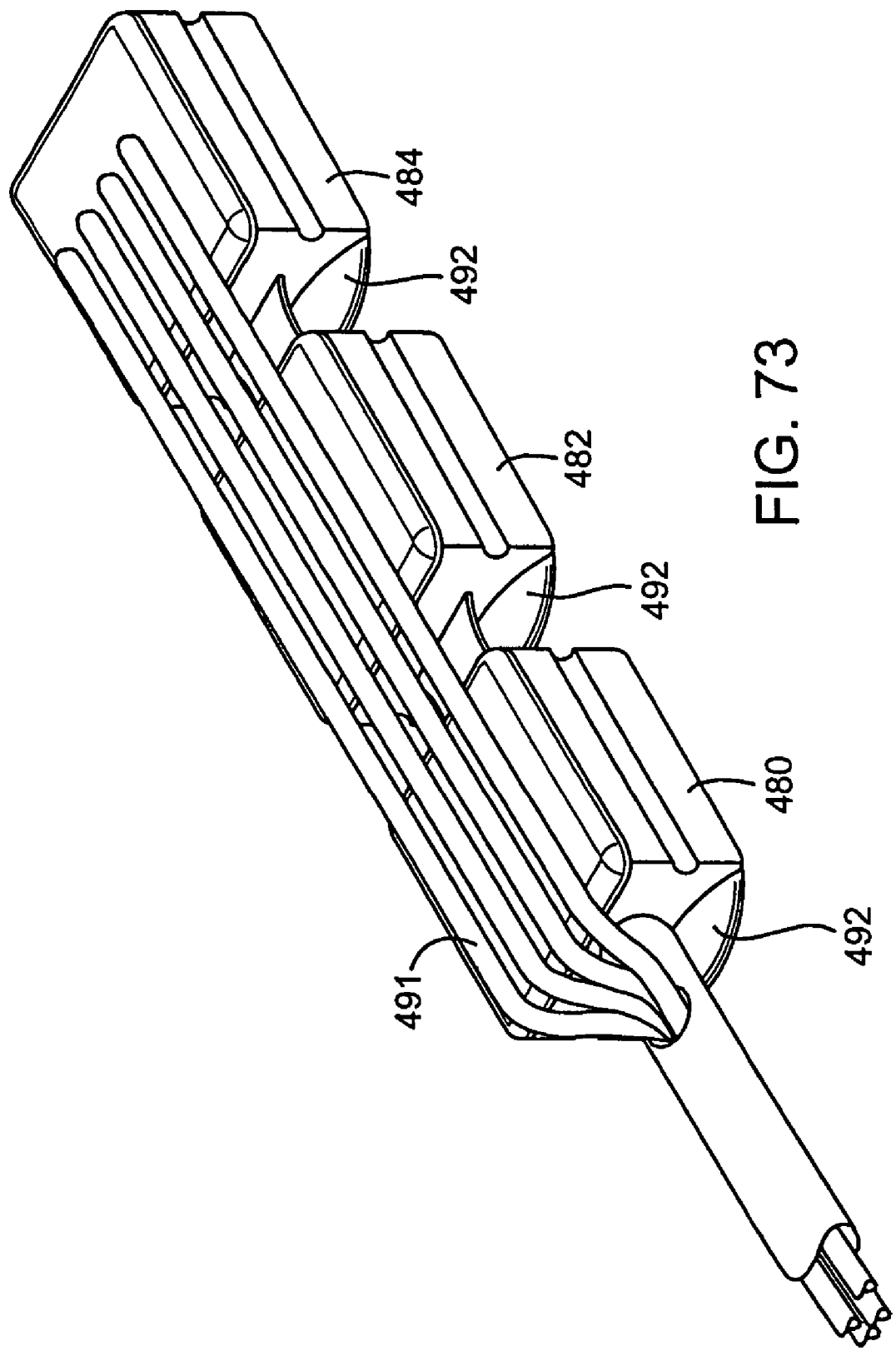

FIG. 73 shows the ablating elements with the body removed.

Figure 74:
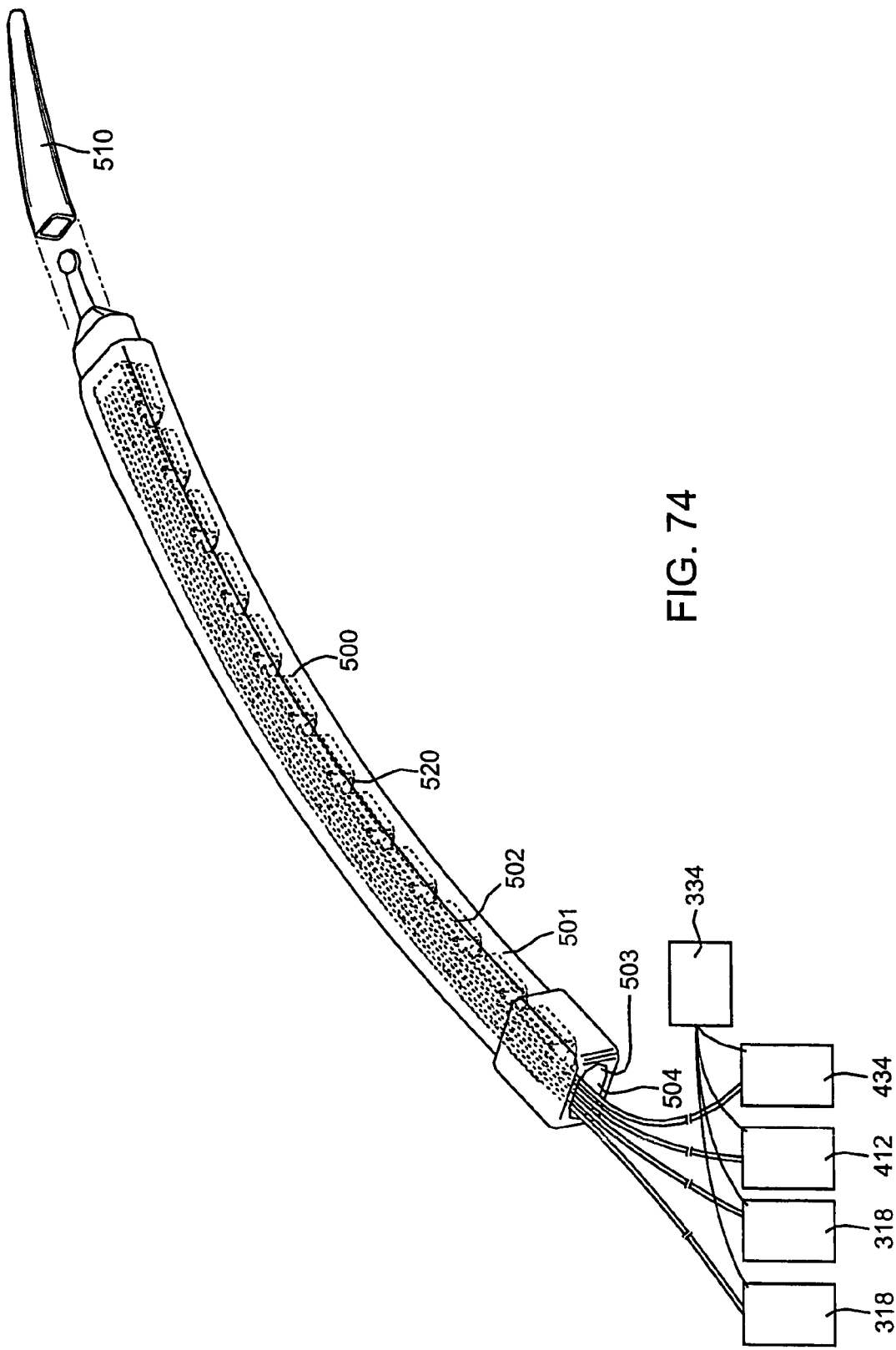

FIG. 74 shows the ablating device having a cover.

Figure 75:
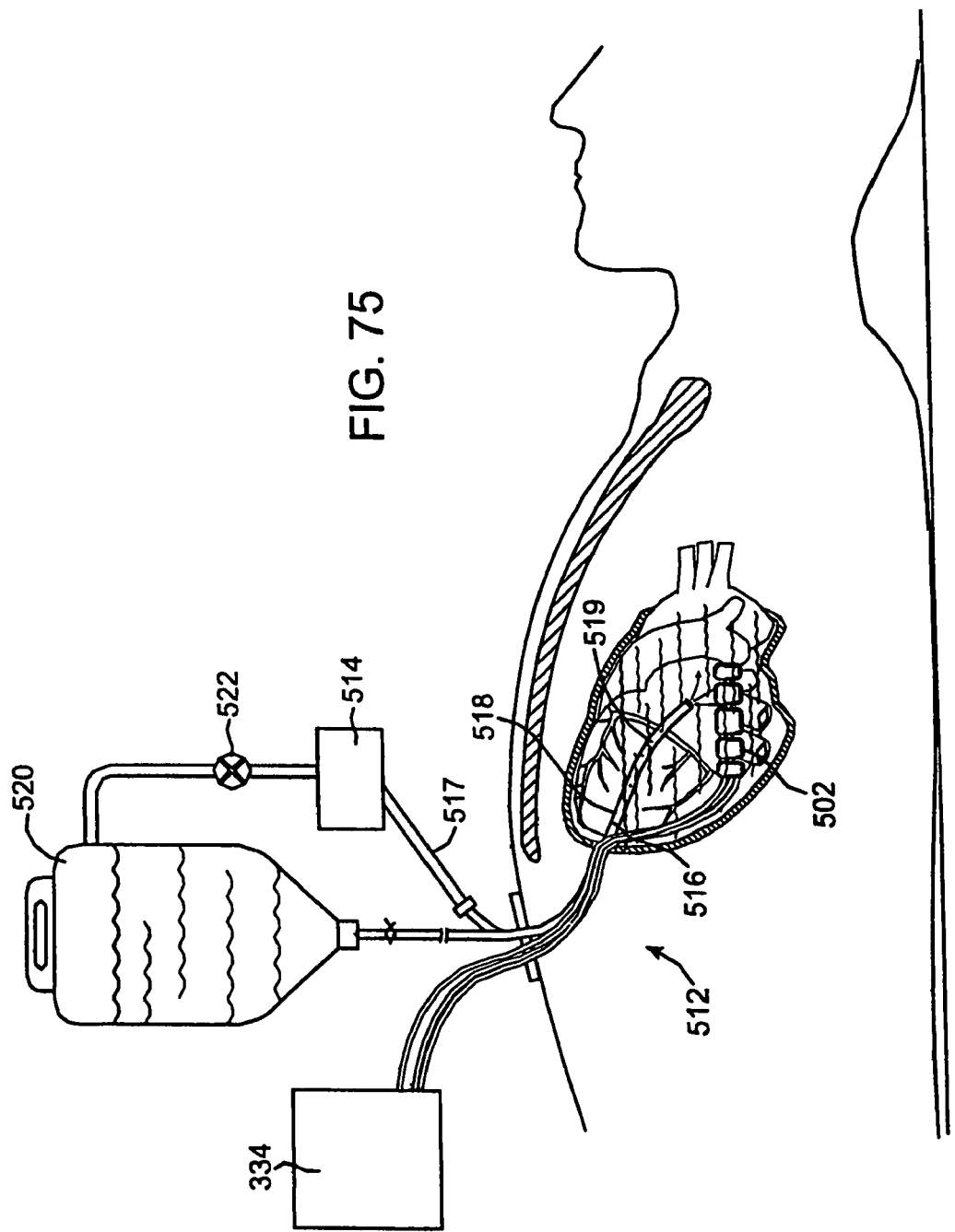

FIG. 75 shows a system for ablating tissue which provides a liquid environment around the heart.

Figure 76:
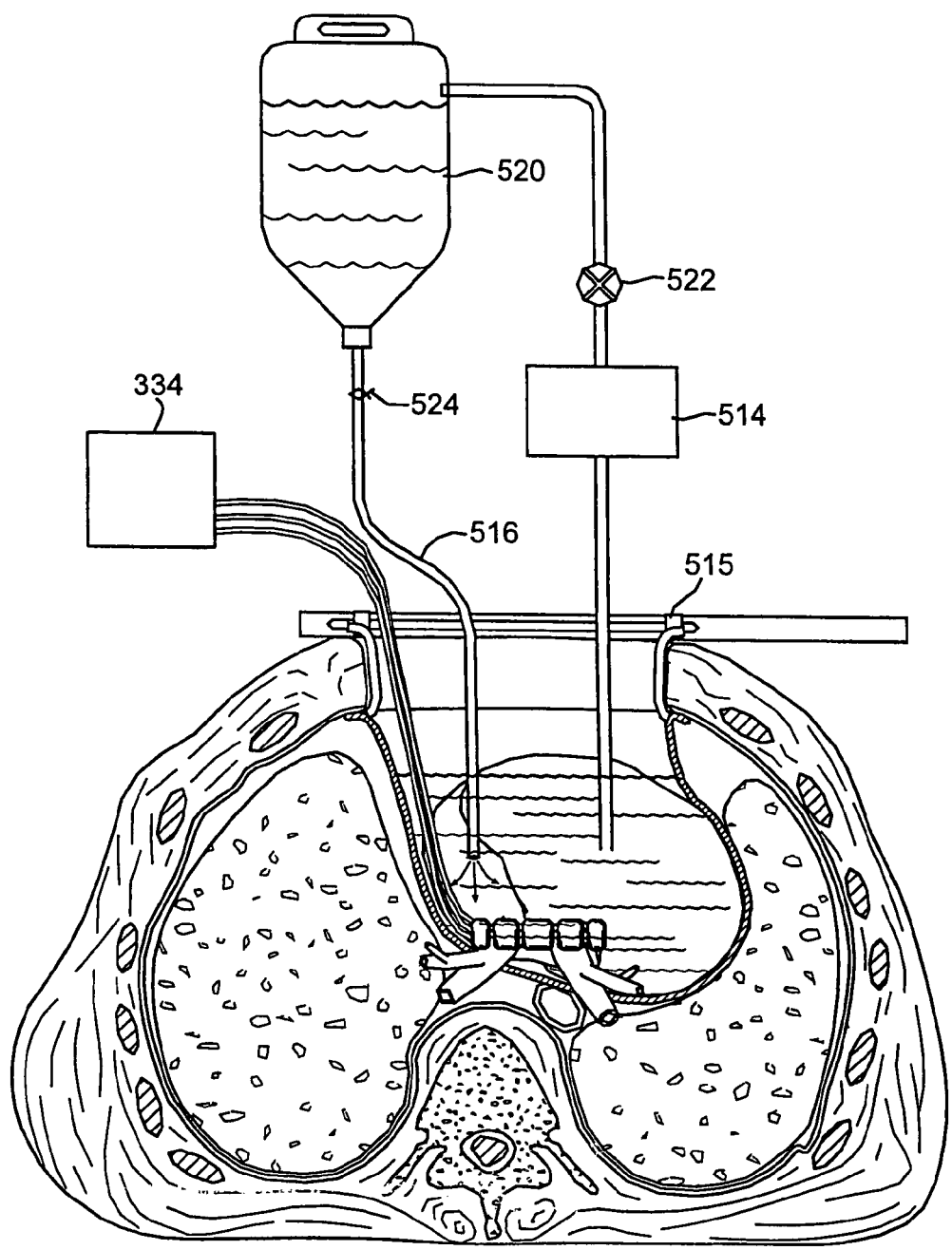

FIG. 76 shows another system for providing a liquid environment around the heart.

Figure 77:
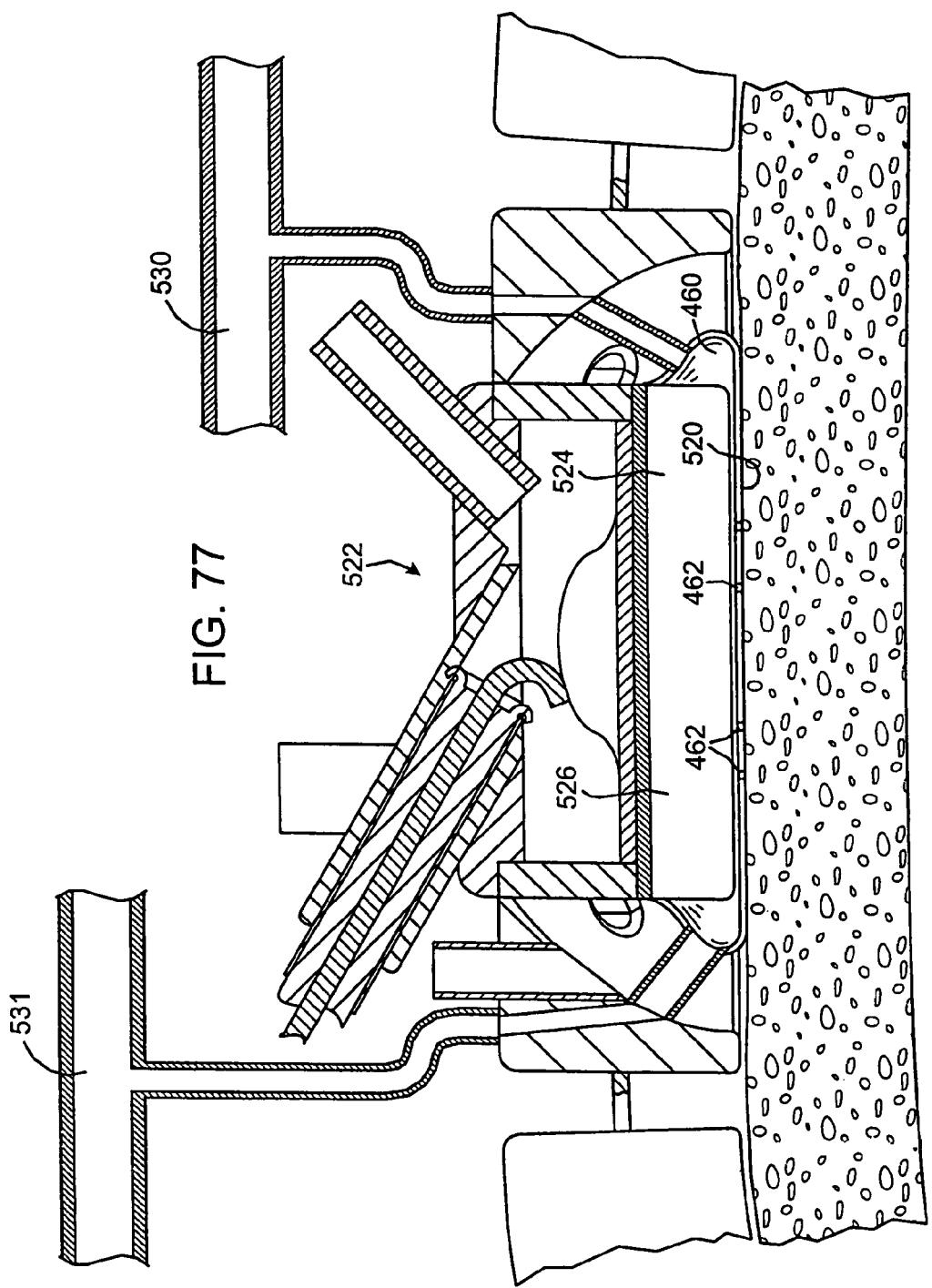

FIG. 77 shows another system for ablating tissue with a membrane extending over the ablating element.

Figure 78:
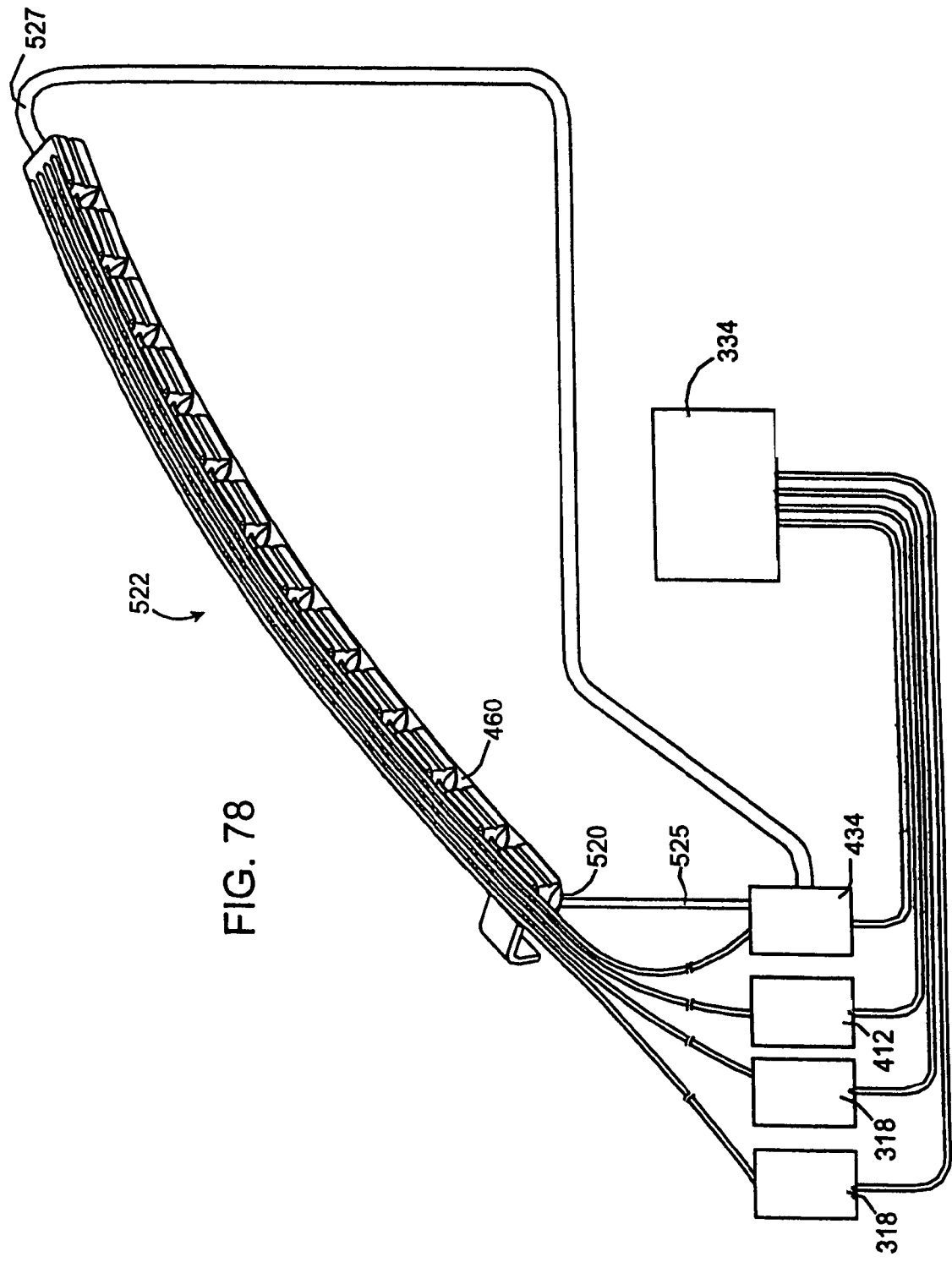

FIG. 78 shows the membrane extending over a number of ablating elements.

Figure 79:
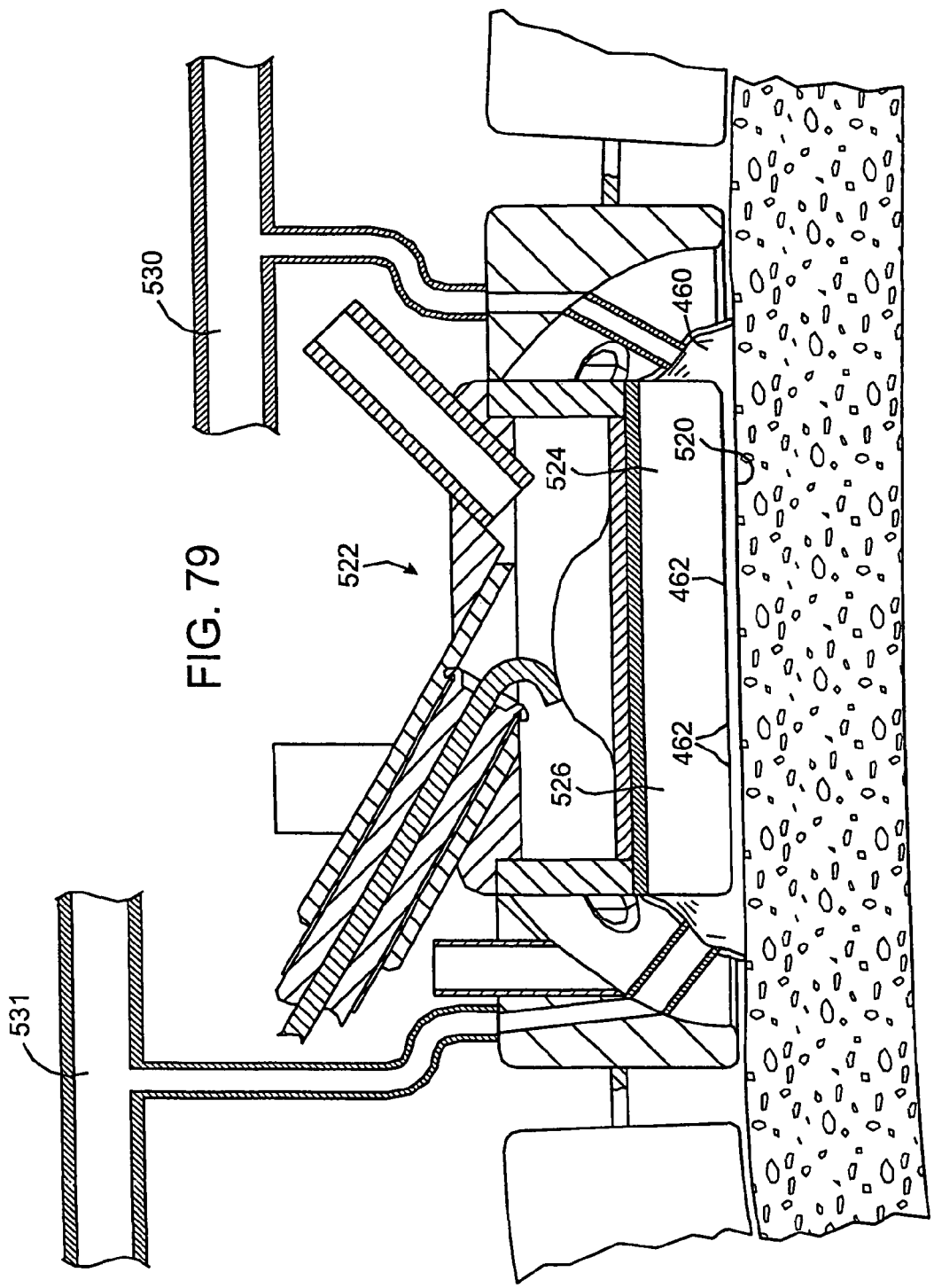

FIG. 79 shows a flexible skirt surrounding the ablating element.

Figure 80:
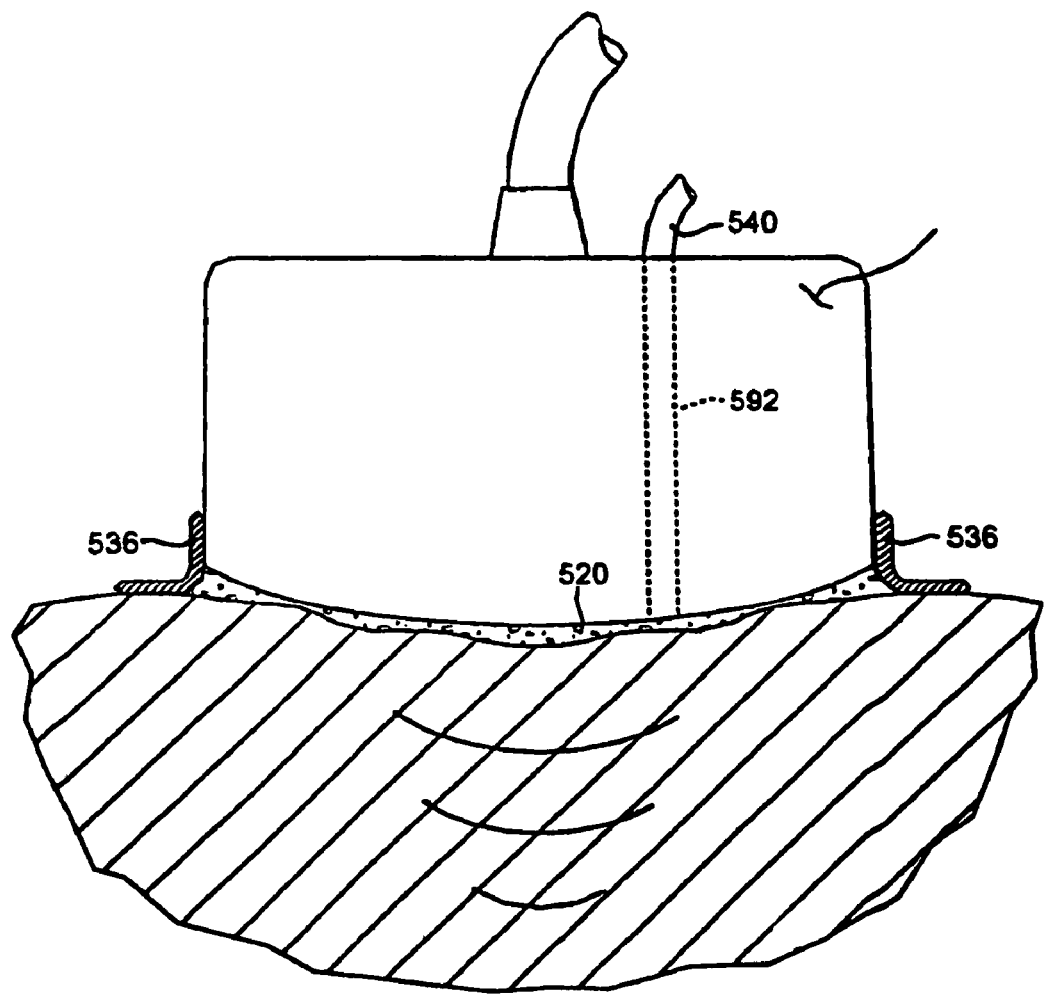

FIG. 80 shows another embodiment of the flexible skirt.

DETAILED DESCRIPTION OF PREFERRED EMBODIMENTS

Figure 1B:
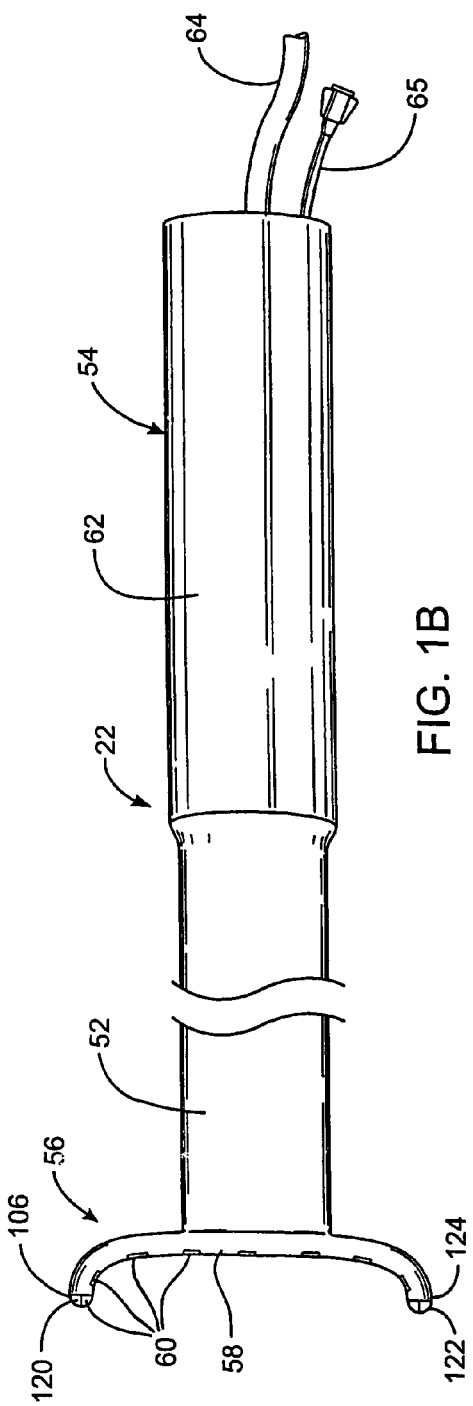
FIG. 1B is a side view of a right ablation probe according to the invention.

FIGS. 1A-1B illustrate a first embodiment of the apparatus of the invention. In this embodiment, the apparatus comprises a left ablation probe 20, shown in FIG. 1A, and a right ablation probe 22, shown in FIG. 1B, which work in tandem to form a transmural lesion isolating the pulmonary veins from the surrounding myocardium. Left ablation probe 20 has a flexible shaft 21 extending to a working end 24 configured for insertion into the chest cavity through a small incision, puncture or access port. Opposite working end 24, shaft 21 is attached to a control end 26 used for manipulating the working end 24 from outside the chest. Shaft 21 is dimensioned to allow introduction through a small incision in the chest, preferably in a subxiphoid location, and advanced to the pulmonary veins on the posterior side of the heart. Preferably, shaft 21 is configured to be flexible about a first transverse axis to allow anterior-posterior bending and torsional flexibility, but relatively stiff about a second transverse axis perpendicular to the first transverse axis to provide lateral bending stiffness. In an exemplary embodiment, shaft 21 has a length in the range of about 10-30 cm, and a guide portion 25 having a rectangular cross-section with a width-to-height ratio of about 2-5, the cross-sectional width being about 6-35 mm and the cross-sectional height being about 3-17 mm. The guide portion 25 aligns the device between the epicardium and pericardium to ablate tissues as described below. Shaft 21 is made of a flexible biocompatible polymer such as polyurethane or silicone, and preferably includes radiopaque markers or a radiopaque filler such as bismuth or barium sulfate.

Working end 24 includes a plurality of ablating elements 27. The ablating elements 27 are preferably a plurality of electrodes 28 for delivering radiofrequency (RF) current to the myocardium so as to create transmural lesions of sufficient depth to block electrical conduction. Electrodes 28 may be partially-insulated solid metal rings or cylinders, foil strips, wire coils or other suitable construction for producing elongated lesions. Electrodes 28 are spaced apart a distance selected so that the lesions created by adjacent electrodes contact or overlap one another, thereby creating a continuous, uninterrupted lesion in the tissue underlying the electrodes. In an exemplary embodiment, electrodes 28 are about 2-20 mm in length and are spaced apart a range of 1-6 mm. It is understood that the term electrodes 28 as used herein may refer to any suitable ablating element 27. For example, as an alternative to RF electrodes, the ablating elements 27 may be microwave transmitters, cryogenic element, laser, heated element, ultrasound, hot fluid or other types of ablation devices suitable for forming transmural lesions. The heated element may be a self-regulating heater to prevent overheating. Electrodes 28 are positioned so as to facilitate lesion formation on the three-dimensional topography of the left atrium. For example, lateral electrodes 28a face medially to permit ablation of the myocardium on the lateral side of the left inferior pulmonary vein and medial electrodes 28b face anteriorly to permit ablation of the posterior surface of the myocardium adjacent to the left inferior pulmonary vein.

Working end 24 further includes a locating mechanism which locates the working end at one of the pulmonary veins and helps to maintain it in position once located. In a preferred embodiment, working end 24 is bifurcated into two branches 30, 32, and the locating mechanism is a notch 34 disposed between the two branches. Notch 34 tapers into a concave surface 36 so as to receive one of the pulmonary veins between branches 30, 32 and to atraumatically engage the pulmonary vein against concave surface 36. In an exemplary embodiment, notch 34 is about 10 to 30 mm in width at its widest point between branches 30, 32 and tapers toward concave surface 36 which has a radius of curvature of about 4 to 15 mm, so as to conform to the outer curvature of the pulmonary vein. Preferably, notch 34 is sized and positioned for placement against the left inferior pulmonary vein, as described more fully below. Alternatively, the locating mechanism may be configured to engage another anatomic structure such as the inferior vena cava, superior vena cava, pericardial reflections, pulmonary vein, aorta, pulmonary artery, atrial appendage, or other structure in the space between the pericardium and the myocardium. The various shapes of the ablating devices described and shown herein are, of course, useful in locating various structures to position the ablating elements against predetermined tissues to be ablated.

Working end 24 further includes a superior sub-probe 38 and an inferior sub-probe 40 which are slidably extendable from working end 24, as further described below.

Control end 26 includes a handle 42 and a plurality of slidable actuators 44A-44E, which are used to extend superior sub-probe 38 and inferior sub-probe 40 from working end 24, and to perform other functions as described below. An electrical connector 46 suitable for connection to an RF generator is mounted to handle 42 and is electrically coupled to electrodes 28 at working end 24. Also mounted to handle 42 are a working port 48 in communication with a working channel 92, described below, and a connector 50 for connection to a source of inflation fluid or suction, used for purposes described below.

Right ablation probe 22 has a flexible shaft 52 extending from a control end 54 to a working end 56. Working end 56 has a cross-member 58 to which are mounted a plurality of electrodes 60. Cross member 58 preferably has tips 59 which are pre-shaped or deflectable into a curve so as to conform to the right lateral walls of the right pulmonary veins, and which are separated by a distance selected so that the two right pulmonary veins may be positioned between them, usually a distance of about 20-50 mm. Electrodes 60 are sized and positioned so as to create a continuous lesion along the right side (from the patient's perspective) of the pulmonary veins as described more fully below. In an exemplary embodiment, electrodes 60 are about 2-20 mm in length, and are spaced apart about 1-6 mm. Shaft 52 is dimensioned to allow introduction through a small incision in the chest, preferably in a subxiphoid location, and advanced to the pulmonary veins on the posterior side of the heart. Shaft 52 will have dimensions, geometry and materials like those of shaft 21 of left ablation probe 20, described above.

Control end 54 includes a handle 62. An electrical connector 64 adapted for connection to an RF generator is attached to handle 62 and is electrically coupled to electrodes 60 at working end 56. An inflation or suction connector 65 is mounted to handle 62 and adapted for connection to a source of inflation fluid or suction, for purposes described below. Handle 62 may further include a working port (not shown) like working port 48 described above in connection with left ablation probe 20.

Figure 2A:
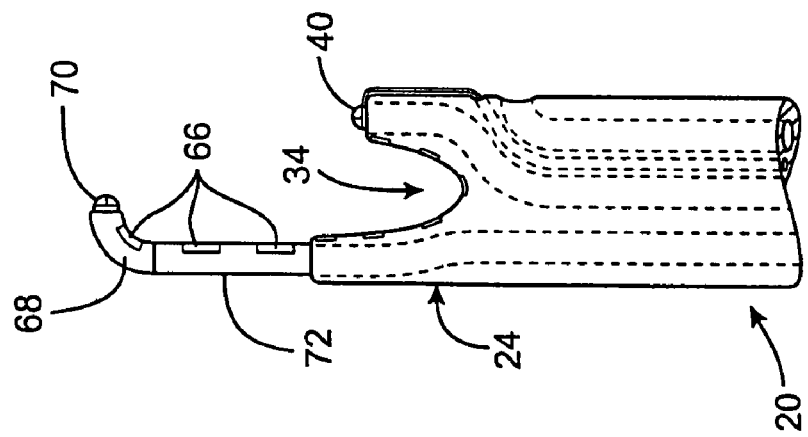
Figure 2B:
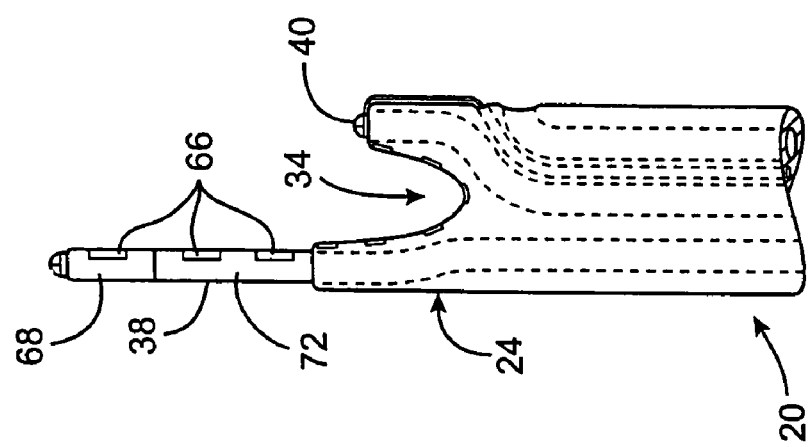
Figure 2C:
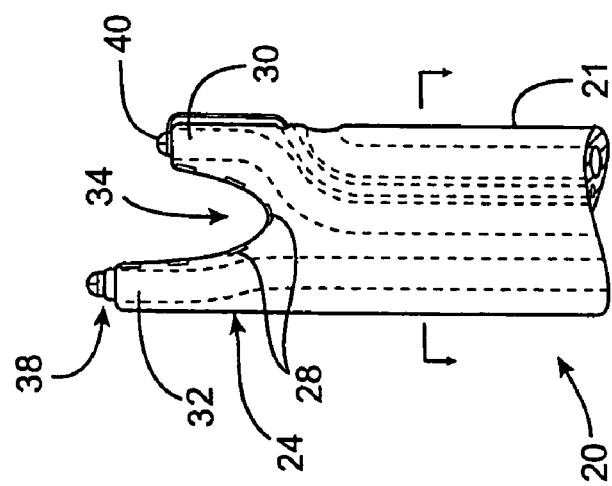

FIGS. 2A-2E illustrate the deployment of the various components of working end 24 of left ablation probe 20. Superior sub-probe 38 is slidably extendable from working end 24 as shown in FIG. 2B. A plurality of electrodes 66 are mounted to superior sub-probe 38 and are sized and positioned to create a continuous lesion along the left side of the pulmonary veins. Superior sub-probe 38 has an articulated or steerable section 68 which can be selectively shaped into the position shown in FIG. 2C, with its distal tip 70 pointing in a lateral direction relative to the more straight proximal portion 72.

As shown in FIG. 2D, an inner probe 74 is slidably extendable from superior sub-probe 38 and is directed by steerable section 68 in a lateral direction opposite notch 34. Inner probe 74 is separated from notch 34 by a distance selected such that inner probe 74 may be positioned along the superior side of the pulmonary veins when the left inferior pulmonary vein is positioned in notch 34. In an exemplary embodiment, the maximum distance from concave surface 36 to inner probe 74 is about 20-50 mm. A plurality of electrodes 76 are mounted to inner probe 74 and positioned to enable the creation of a continuous transmural lesion along the superior side of the pulmonary veins as described more fully below.

Referring to FIG. 2E, inferior sub-probe 40 is slidably extendable from working end 24. Its distal tip 78 is attached to a tether 80 extending through a lumen in shaft 21. Tether 80 may be selectively tensioned to draw distal tip 78 away from inner probe 74 (toward control end 26), imparting a curvature to inferior sub-probe 40. Inferior sub-probe 40 is constructed of a resilient, bendable plastic which is biased into a straight configuration. When inferior sub-probe 40 has been advanced sufficiently, tether 80 may be released, whereby the resiliency of inferior sub-probe 40 causes it to conform to the pericardial reflection and the medial and/or inferior sides of the four pulmonary veins. Inferior sub-probe 40 further includes a plurality of electrodes 82 sized and positioned to produce a continuous transmural lesion in the myocardium along the inferior side of the pulmonary veins, as described more fully below.

Figure 3:
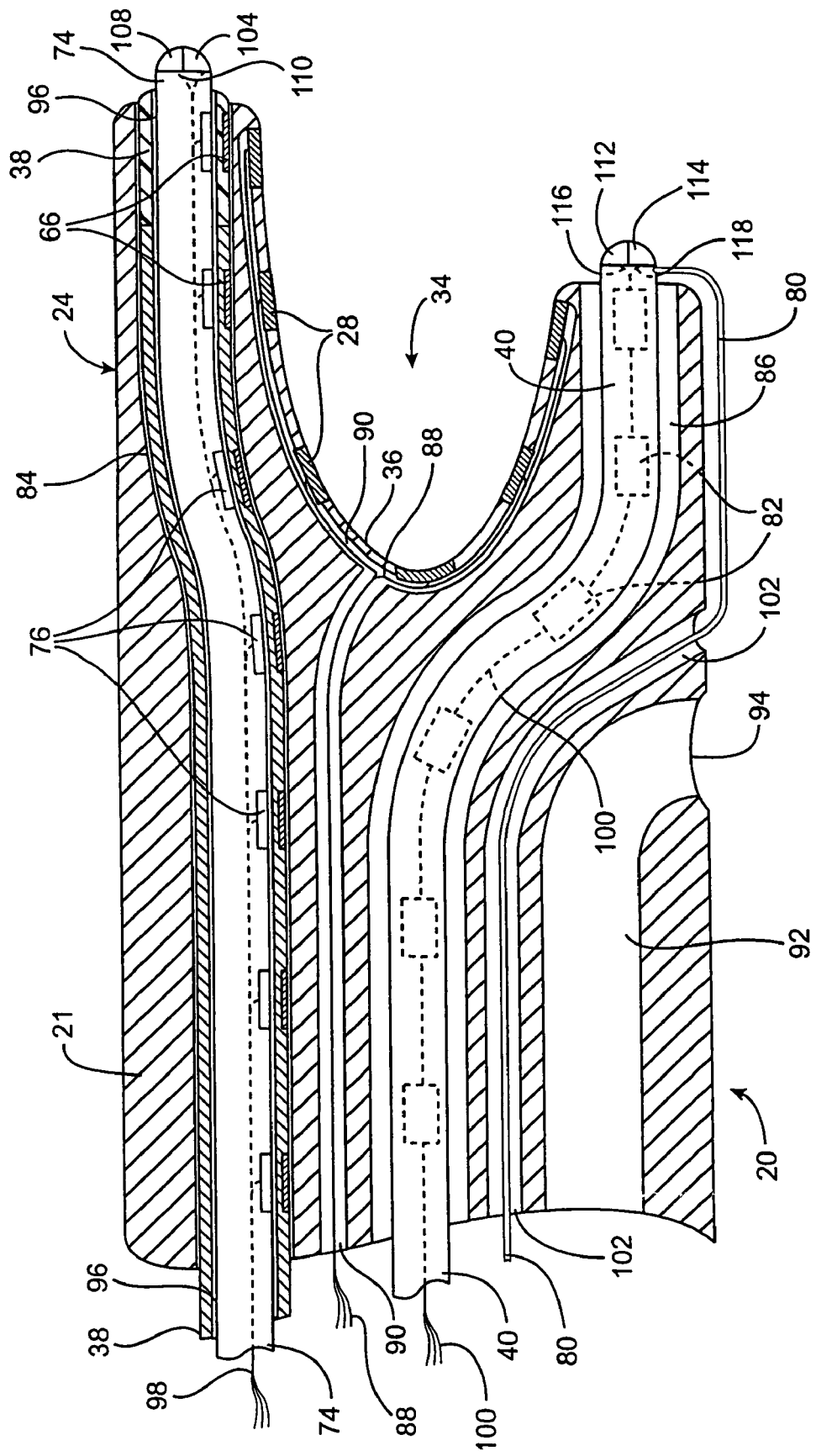
FIG. 3 is a side cross-section of the working end of the left ablation probe of FIG. 1A.
Figure 4:
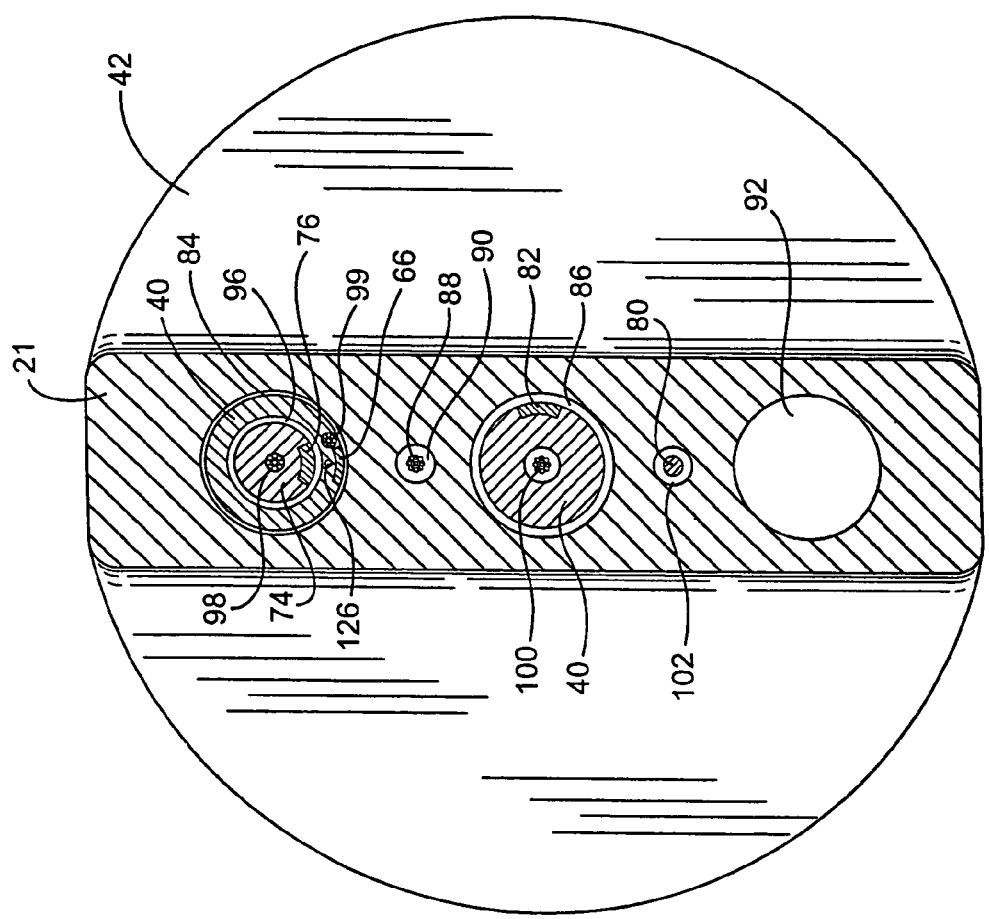
FIG. 4 is a transverse cross-section of the shaft of the left ablation probe of FIG. 1A.

Referring to FIGS. 3 and 4, superior sub-probe 38 is slidably disposed in a first lumen 84 and inferior sub-probe 40 is slidably disposed in a second lumen 86 in shaft 21. Electrodes 28 along notch 34 are coupled to wires 88 disposed in a wire channel 90 running beneath electrodes 28 and extending through shaft 21. Each electrode is coupled to a separate wire to allow any electrode or combination of electrodes to be selectively activated. Shaft 21 also includes a working channel 92 extending to an opening 94 in working end 24 through which instruments such as endoscopes, suction/irrigation devices, mapping and ablation devices, tissue retraction devices, temperature probes and the like may be inserted.

Superior sub-probe 38 has an inner lumen 96 in which inner probe 74 is slidably disposed. Electrodes 76 on inner probe 74 are coupled to wires 98 extending through inner probe 74 to connector 46 on handle 42, shown in FIG. 1A. Similarly, electrodes 66 on superior sub-probe 38 are coupled to wires 99 (FIG. 4) and electrodes 82 on inferior sub-probe 40 are coupled to wires 100, both sets of wires extending to connector 46 on handle 42. Tether 80 slidably extends through tether lumen 102 in shaft 21.

The distal end of inner probe 74 has a tip electrode 104 for extending the transmural lesion produced by electrodes 76. Preferably, inner probe 74 further includes a device for approximating the tip of inner probe 74 with the superior tip 106 of right ablation probe 22 (FIG. 1B) when the two are separated by a pericardial reflection. In a preferred embodiment, a first electromagnet 108 is mounted to the distal end of inner probe 74 adjacent to tip electrode 104. First electromagnet 108 is coupled to a wire 110 extending to handle 42, where it is coupled to a power source and a switch (not shown) via connector 46 or a separate connector. Similarly, a second electromagnet 112 is mounted to distal tip 78 of inferior sub-probe 40, adjacent to a tip electrode 114, which are coupled to wires 116, 118 extending to a connector on handle 42. As shown in FIG. 1B, a third electromagnet 120 is mounted to superior tip 106 of right ablation probe 22, and a fourth electromagnet 122 is mounted to inferior tip 124 of right ablation probe 22. Electromagnets 120, 122 are coupled to wires (not shown) extending to a connector on handle 62 for coupling to a power source and switch. In this way, superior tip 106 and inferior tip 124 may be approximated with inner probe 74 and inferior sub-probe 40 across a pericardial reflection by activating electromagnets 108, 112, 120, 122.

It should be noted that thermocouples, thermistors or other temperature monitoring devices may be mounted to the working ends of either left or right ablation probes 20, 22 to facilitate temperature measurement of the epicardium during ablation. The thermocouples may be mounted adjacent to any of the electrodes described above, or may be welded or bonded to the electrodes themselves. The thermocouples will be coupled to wires which extend through shafts 21, 52 alongside the electrode wires to connectors 46, 64 or to separate connectors on handles 42, 62, facilitating connection to a temperature monitoring device.

FIGS. 5A-5C illustrate the operation of superior sub-probe 38. Superior sub-probe 38 has a pull wire 126 movably disposed in a wire channel 128 in a sidewall adjacent to inner lumen 96. Pull wire 126 is fixed at its distal end 130 to steerable section 68 of superior sub-probe 38. Steerable section 68 is constructed of a flexible, resilient plastic such that by tensioning pull wire 126, steerable section 68 may be deformed into a curved shape to direct inner probe 74 in a transverse direction relative to the straight proximal portion 72, as shown in FIG. 5B. Once in this curved configuration, inner probe 74 may be slidably advanced from superior sub-probe 38 as shown in FIG. 5C.

Referring to FIG. 6, actuator 44D is slidably disposed in a longitudinal slot 132 in handle 42 and is coupled to the proximal end of inferior sub-probe 40. Actuator 44E is slidably disposed in a longitudinal slot 134 in handle 42 and is coupled to the proximal end of tether 80. When sub-probe 40 is to be deployed, actuator 44D is slid forward, advancing inferior sub-probe 40 distally. Actuator 44E may be allowed to slide forward as well, or it may be held in position to maintain tension on tether 80, thereby bending sub-probe 40 into the curved shape shown in FIG. 2E. When sub-probe 40 has been fully advanced, actuator 44E may be released, allowing distal end 78 of sub-probe 40 to engage the pericardial reflection along the inferior surfaces of the pulmonary veins, as further described below.

Actuators 44A-C are slidably disposed in a longitudinal slot 136 in handle 42, as more clearly shown in FIG. 7. Actuator 44A is attached to the proximal end of superior sub-probe 38, and may be advanced forward to deploy the sub-probe from working end 24, as shown in FIG. 2A. Actuator 44B is attached to inner probe 74, which is frictionally retained in inner lumen 96 such that it is drawn forward with superior sub-probe 38. Actuator 44C is attached to pull wire 126 which is also drawn forward with superior sub-probe 38. In order to deflect the steerable section 68 of superior sub-probe 38, actuator 44C is drawn proximally, tensioning pull wire 126 and bending steerable section 68 into the configuration of FIG. 2C. Finally, to deploy inner probe 74, actuator 44B is pushed forward relative to actuators 44A and 44C, advancing inner probe 74 from superior sub-probe 38 as shown in FIG. 2D.

The slidable relationship between the shafts and probes 74, 40, 38 helps to guide and direct the probes to the tissues to be ablated. The shafts have various features, including the ablating elements 27, however, the shafts may be simple sheaths which locate structures and/or direct the probes into various regions of the pericardial space.

Referring now to FIGS. 8-11, a preferred embodiment of the method of the invention will be described. Initially, left ablation probe 20 and right ablation probe 22 are connected to an RF generator 140. RF generator 140 will preferably provide up to 150 watts of power at about 500 kHz, and will have capability for both temperature monitoring and impedance monitoring. A suitable generator would be, for example, a Model No. EPT-1000 available from the EP Technologies Division of Boston Scientific Corp. of Natick, Mass. Retraction, visualization, temperature monitoring, suction, irrigation, mapping or ablation devices may be inserted through working port 142. Left ablation probe 20 may further be connected to a source of suction or inflation fluid 144, for reasons described below. If electromagnets are provided on left and right ablation probes 20, 22 as described above, an additional connection may be made to a power supply and switch for operating the electromagnets, or power may be supplied by RF generator 140 through connectors 46, 64.

A subxiphoid incision (inferior to the xiphoid process of the sternum) is made about 2-5 cm in length. Under direct vision through such incision or by visualization with an endoscope, a second small incision is made in the pericardium P (FIG. 9). Left ablation probe 20 is introduced through these two incisions and advanced around the inferior wall of the heart H to its posterior side under fluoroscopic guidance using fluoroscope 146. Alternative methods of visualization include echocardiography, endoscopy, transillumination, and magnetic resonance imaging. Left ablation probe 20 is positioned such that left inferior pulmonary vein LI is disposed in notch 34 as shown in the posterior view of the heart in FIG. 10.

Superior sub-probe 38 is then advanced distally from working end 24 until its steerable section 68 is beyond the superior side of the left superior pulmonary vein LS. Steerable section 68 is then deflected into the curved configuration shown in FIG. 10 such that its distal end 70 is superior to the left superior pulmonary vein LS and pointing rightward toward the right superior pulmonary vein RS. Inner probe 74 is then advanced toward the right until its distal tip is very close to or contacting the pericardial reflection PR superior to the right superior pulmonary vein RS.

Inferior sub-probe 40 is next advanced from working end 24 while maintaining tension on tether 80 such that the inferior sub-probe engages and conforms to the shape of the pericardial reflection PR between the left inferior and right inferior pulmonary veins. When inferior sub-probe 40 has been fully advanced, tension is released on tether 80 so that distal tip 78 moves superiorly into engagement with the right inferior pulmonary vein RI adjacent to pericardial reflection PR inferior thereto.

Right ablation probe 22 is placed through the subxiphoid incision and pericardial incision and advanced around the right side of the heart as shown in FIG. 8. Under fluoroscopic guidance, right ablation probe 22 is positioned such that cross-member 58 engages the right superior and inferior pulmonary veins, as shown in FIG. 10. In this position, superior tip 106 and inferior tip 124 should be generally in opposition to distal tip 75 of inner probe 74 and distal tip 78 of inferior sub-probe 40, respectively, separated by pericardial reflections PR. In order to ensure close approximation of the two tip pairs, electromagnets 108, 120, 114, 122 may be energized, thereby attracting the tips to each other across the pericardial reflections RS.

It should be noted that the pericardium P attaches to the heart at the pericardial reflections PR shown in FIGS. 10-11. Because of the posterior location of the pulmonary veins and the limited access and visualization available, cutting or puncturing the pericardial reflections in the vicinity of the pulmonary veins poses a risk of serious injury to the heart or pulmonary veins themselves. The apparatus and method of the present invention avoid this risk by allowing the pericardial reflections to remain, intact, without any cutting or puncturing thereof, although the pericardial reflections may also be cut without departing from the scope of the invention.

RF generator 140 is then activated to deliver RF energy to electrodes 28, 60, 66, 76, 82, 104, and 112 on left and right ablation probes 20, 22, producing the transmural lesion L shown in FIG. 11. Preferably, power in the range of 20-150 watts is delivered at a frequency of about 500 kHz for a duration of about 30-180 seconds, resulting in localized myocardial temperatures in the range of 45-95.degree. C. Ultrasound visualization may be used to detect the length, location and/or depth of the lesion created. Lesion L forms a continuous electrically-insulated boundary encircling the pulmonary veins thereby electrically isolating the pulmonary veins from the myocardium outside of lesion L.

Ablation probes 20, 22 may further be used for mapping conduction pathways in the heart (local electrocardiograms) for the diagnosis of electrophysiological abnormalities. This is accomplished by selecting any of the electrodes on the ablation probes and monitoring the voltage. A commercially available electrophysiology monitoring system is utilized, which can select any electrode on the ablation probes and monitor the voltage. Various electrodes and various locations on the heart wall may be selected to develop a map of potential conduction pathways in the heart wall. If ablation treatment is then required, the steps outlined above may be performed to create transmural lesions at the desired epicardial locations.

During any of the preceding steps, devices may be placed through working port 142 and working channel 92 to assist and supplement the procedure. For example, a flexible endoscope may be introduced for visualization to assist positioning. Ultrasound probes may be introduced to enhance visualization and for measuring the location and/or depth of transmural lesions. Suction or irrigation devices may be introduced to clear the field and remove fluid and debris. Tissue manipulation and retraction devices may be introduced to move and hold tissue out of the way. Cardiac mapping and ablation devices may also be introduced to identify conduction pathways and to supplement the ablation performed by left and right ablation probes 20, 22.

Furthermore, mapping and ablation catheters, temperature monitoring catheters, and other endovascular devices may be used in conjunction with the left and right ablation probes of the invention by introducing such devices into the right atrium or left atrium either through the arterial system or through the venous system via the right atrium and a transeptal puncture. For example, an ablation catheter may be introduced into the left atrium to ablate any region of the myocardium not sufficiently ablated by left and right ablation probes 20, 22 in order to ensure complete isolation of the pulmonary veins. Additionally, ablation catheters may be introduced into the right chambers of the heart, or epicardial ablation devices may be introduced through incisions in the chest, to create other transmural lesions.

In some cases, it may be desirable to actively ensure adequate contact between the epicardium and the electrodes of left and right ablation probes 20, 22. For this purpose, left ablation probe 20 and/or right ablation probe 22 may include one or more expandable devices such as balloons which are inflated in the space between the heart and the pericardium to urge the ablation probe against the epicardial surface. An exemplary embodiment is shown in FIG. 12, in which a balloon 150 is mounted to the outer surface of inner probe 74 opposite electrodes 76 on left ablation probe 20. Inner probe 74 further includes an inflation lumen 152 in communication with an opening 154 within balloon 150 and extending proximally to inflation fitting 50 on handle 42, through which an inflation fluid such as liquid saline or gaseous carbon-dioxide may be delivered. When inflated, balloon 150 engages the inner surface of the pericardium P and urges inner probe 74 against the epicardial surface of heart H. This ensures close contact between electrodes 76 and the epicardium, and protects extracardiac tissue such as the pericardium and phrenic nerve from injury caused by the ablation probes. Balloons or other expandable devices may similarly be mounted to superior sub-probe 38, inferior sub-probe 40, or right ablation probe 22 to ensure sufficient contact between the epicardium and the electrodes on those components.

Alternatively or additionally, suction ports may be provided in the ablation probes of the invention to draw the electrodes against the epicardium, as shown in FIG. 13. In an exemplary embodiment, suction ports 156 are disposed in inner probe 74 between or adjacent to electrodes 76. Suction ports 156 are in communication with a suction lumen 158 which extends proximally to suction fitting 48 on handle 42. In this way, when suction is applied through suction port 156, inner probe 74 is drawn tightly against the heart, ensuring good contact between electrodes 76 and the epicardium. In a similar manner, superior sub-probe 38, inferior sub-probe 40 and right ablation probe 22 may include suction ports adjacent to the electrodes on those components to enhance contact with the epicardium.

Referring to FIGS. 14A, 15, 16 and 17, the ablating device 20 is shown with various features described above. The embodiments are specifically referred to as ablating device 20A and like or similar reference numbers refer to like or similar structure. The ablating device 20A may have any of the features of the ablating devices 20, 22 described above and all discussion of the ablating devices 20, 22 or any other ablating device described herein is incorporated here. As mentioned above, the ablating device 20A may have a preshaped portion 160 or a flexible or bendable portion 162 as shown in FIGS. 14 and 15, respectively. A stylet 164 or sheath (not shown) is used to shape the ablating device 20A as described below. The stylet 164 passes through a working channel 166 which may receive other devices as described above. The working channel 166 may also be coupled to a source of fluid 169, such as fluoroscopic contrast, which may be used for visualization. The contrast may be any suitable contrast including barium, iodine or even air. The fluoroscopic contrast may be introduced into the pericardial space to visualize structures in the pericardial space.

Referring to FIG. 14A, the pre-shaped portion 160 has a curved or L-shape in an unbiased position. The distal portion of the device 20A may have any other shape such as a hook or C-shape to pass the device 20A around a structure. The stylet 164 holds the pre-shaped portion 160 in any other suitable geometry, such as dotted-line 167, for introduction and advancement of the ablating device 20A. The stylet 164 may also be malleable. When the ablating device 20A is at the appropriate position, the stylet 164 is withdrawn thereby allowing the distal end 160 to regain the angled or curved shape. The device 20A may also be shaped with a sheath (not shown) through which the device 20A passes in a manner similar to the manner of FIGS. 2 and 5.

Referring to FIG. 15, the ablating device 20A has the flexible distal portion 162 which is shaped by the stylet 164 into the dotted line 168 position. The pre-shaped portion 160 may be used to position or advance the ablating device 20A between the epicardium and pericardium. FIG. 18 shows the pre-shaped portion positioned around the left superior pulmonary vein as described below. A number of different stylets 164 may be used to shape the flexible portion 162 around various structures.

The ablating device 20A also has an anchor 170 to anchor a portion of the device 20A while moving another part of the device 20A. When the anchor 170 is the balloon 150, the balloon may have a number of chambers 171, preferably three, which can be inflated as necessary to position the device as shown in FIGS. 16 and 17. The chambers 171 are coupled to a source of inflation fluid 173 via inflation lumens 175. The anchor 170 is preferably an expandable element 172 such as the balloon 150, but may also be tines which grab the epicardium, pericardium or pericardial reflection. The anchor 170 may also be one or more suction ports 156, as described above (see FIG. 13). The suction ports 156 may be used to anchor the device to the pericardium, epicardium, pericardial reflection or any other structure in the space between the pericardium and epicardium. Although only one anchor 170 is located at the distal end, the anchor 170 may be positioned at any other location and more than one anchor 170 may be provided without departing from the scope of the invention.

Referring to FIGS. 18-21, a specific use of the ablating device 20A is now described. The ablating devices described herein may, of course, be used to ablate other tissues when positioned in the space between the epicardium and pericardium. The ablating device 20A is preferably introduced in the same manner as the ablating device 20 or in any other suitable manner. When the ablating device 20A is at the entrance to the transverse pericardial sinus, the ablating device 20A may be given the angled or curved shape by advancing or withdrawing the stylet 164 (see FIGS. 14 and 15) or with the sheath (see FIGS. 2 and 5). The device 20A is then advanced until the tip meets the pericardial reflection at the end of the sinus as shown in FIG. 18. The anchor 170, such as the balloon 150, is then actuated to resist movement of the distal end when displacing other parts of the ablating device 20A (FIG. 19). At this time, the ablating device 20A may be used to ablate tissue in the manner described above from a position superior to the right superior pulmonary vein, around the left superior pulmonary vein and to the left inferior pulmonary vein. Thus, the ablating device 20A is similar to the ablating device 20 described above in that the device 20A extends through the transverse pericardial sinus and to the left inferior pulmonary vein.

The ablating device 20A, like the ablating device 20, may also have a portion 176 which is moved to ablate tissue inferior to the left and right inferior pulmonary veins. Stated another way, the portion 176 is moved to a position inferior to the inferior pulmonary veins. The portion 176 is moved into the position shown in FIG. 20 by simply pushing the device 20A to displace the portion 176 or by advancing or withdrawing the stylet 164. After the ablating device 20A is properly positioned, the ablating elements 27 are activated as described above to create transmural lesions.

Still referring to FIG. 20, another ablating device 22A may also be used to ablate tissue in the same manner as the ablating device 22 described above. The ablating device 22A is introduced in the manner described above and is advanced until distal end 177 is positioned at a desired location. FIG. 20 shows the distal end 177 superior to the right superior pulmonary vein adjacent to the pericardial reflection. A portion 179 of the ablating device 20A is then moved to the position of FIG. 21 in any manner described above such as by introduction or withdrawal of the stylet 164. The ablating device 20A is then used to ablate tissue as described above.

The ablating device 20A, 22A are also similar to the ablating devices 20, 22 in that the ablating devices 20A, 22A create continuous lesions on both sides of the pericardial reflections extending between the vena cava and the right superior and right inferior pulmonary veins. Tissue beneath the pericardial reflections is ablated using at least one of the ablating devices 20A, 22A. The ablating devices 20A, 22A may be approximated using any suitable technique or device such as with magnetic force described above. Other methods and devices for creating a continuous lesion beneath a pericardial reflection are described below.

Referring now to FIG. 22, another system and method for approximating the ablating devices 20, 22 and 20A, 22A is now described. An energy emitter 180, such as a light source 182, emits energy from the ablating device 20A which is received by a sensor 184 on the other ablating device 22A to determine when the devices 20A, 22A are positioned on opposite sides of a pericardial reflection. The emitter 180 and sensor 184 preferably pass through the working channel 166 but may also be integrated into the devices 20A, 22A. When the ablating devices 20A, 22A are aligned across the pericardial reflection, the sensor 184 detects proper alignment so that the lesion may be formed continuously on both sides of the pericardial reflection.

Yet another method to make sure that the ablating devices 20A, 22A are aligned across a pericardial reflection is to mark a location on the pericardial reflection where a lesion has been created as shown in FIG. 23. The device 20A has a needle 185 introduced through the working channel 166. The needle 185 delivers a marker 186, such as a radiopaque dye, which can be visualized. The device 20A may also deliver a solid marker such as a platinum wire. An advantage of using the marker 186 is that both ablating devices 20A, 22A do not need to be positioned on opposite sides of the pericardial reflection at the same time. Thus, only one ablating device 20A may be necessary to create a continuous lesion beneath the pericardial reflection since the same device 20A can mark the pericardial reflection on one side, locate the mark 186 on the other side, and continue the lesion on the other side of the pericardial reflection.

Referring again to FIG. 10, the ablating device 20 has the guide portion 25. As mentioned above, the guide portion 25 preferably has a width to height ratio of about 2 to 5. The guide portion 25 aligns the ablating element 27 against a predetermined structure, such as the pulmonary veins, to ablate tissue. The relatively flat configuration of the guide portion 25 aligns the device 20 between the epicardium and the pericardium so that the ablating elements 27 are directed toward the myocardium.

Referring now to FIG. 24, an ablating device 20B is shown which has a number of discrete guide portions 25A. Four guide portions 25A are shown in FIG. 24 with each guide portion 25A being shaped similar to a fin 29. The ablating device 20A may also have a beaded or scalloped appearance. The ablating device 20A preferably has flexible sections 188 between the guide portions 25A which provide torsional flexibility so that the guide portions 25A can rotate relative to one another. The guide portions 25A may be positioned between the pulmonary veins as shown in FIG. 27A. The ablating device 20B may have any of the features of the other ablating devices 20, 20A described herein.

Referring to FIG. 25, another ablating device 20C is shown which has guide portions 25B which may also be deployed after the ablating device 20C has been positioned so that the guide portion 25B does not interfere with advancement and placement. The guide portion 25B has one or more expanding elements 192, such as the balloons 150, which may be expanded during advancement or after the device 20A is at the desired location. The expanding elements 192 are positioned on opposite sides of the ablating device 20C, however, the expanding elements 192 may be positioned only on one side of the device 20C. The guide portions 25A may be positioned between the pulmonary veins as shown in FIG. 27B. The expanding elements 192 may also be mechanically actuated elements such as bending arms or an expandable mesh.

The expanding elements 192 may also be inflated at selected locations corresponding to discrete ablation sites as shown in FIG. 26. An advantage of individual expansion of the expanding elements 192 is that other portions of the device 20C may rotate and displace as necessary to provide good contact at the desired ablation site 193.

Another ablating device 20D is now described with reference to FIGS. 28-31. The ablating device 20D is advanced over a guide 260 which is advanced ahead of the device 199. The guide 200 is preferably a guidewire 202 having the anchor 170 to anchor an end 204 of the guide 200. The guide 200 is advanced and positioned along the intended ablation path. The ablating device 20D is then retracted or advanced along the guide 200 to create a continuous lesion along the intended ablation path. The guide 200 may also be locked into a desired orientation with a coaxial cable or with a mechanism similar to locking arms used to hold surgical devices. The ablating device 20D has an expanding device 201, such as the balloon 150, to move the ablating element 27 into contact with the tissue to be ablated. The balloon 150 preferably has a number of chambers 203, preferably at least two, coupled to inflation lumens 205, 207 which are coupled to the source of inflation fluid 173 (FIG. 14A). Electrodes 191, 193 are coupled to wires 209, 211 passing through the device 20D. The guide 200 passes through the working channel 166. Wires 213 are also provided to steer, rotate and position the device 20D.

The ablating device 20D and/or the guide 200 preferably includes a device 206 for aligning the ablating element with a previously created lesion. The aligning device 206 may be electrodes 191, 193 which simply measure electrical impedance. When the electrodes 191, 193 measure a large increase in electrical impedance an ablation is positioned beneath the electrodes 191, 193. In this manner, the ablating element 27 can be aligned and positioned to create a continuous lesion through the tissue. Referring to FIG. 29, the electrodes 191, 193 may also be used to locate the previously created lesion 195 as shown in FIG. 29. The electrode 191 will sense a higher amplitude of activity than the electrode 193 since the electrode is positioned over the previously created lesion while the electrode 191 is not.

Still referring to FIG. 28, the ablating device 20D may have first and second electrodes 194, 196 on opposite sides of the ablating element 27. The first electrode 194 may be a pacing electrode 195 which emits an electrical impulse and the second electrode 196 may be a sensing electrode 197 which receives electrical impulses. When the first electrode 194 emits a stimulus, launching a cardiac impulse, the impulse is transmitted through tissue to the sensing electrode 197 if a discontinuity exists in the lesion. A number of sensing electrodes 197 may be positioned along the ablating device 20A which may be used to determine the location of a discontinuity. Both electrodes 194, 196 may also be sensing electrodes 197 with both electrodes 194, 196 merely sensing normal activity. When only one of the electrodes 194, 196 senses the activity an effective, continuous, transmural lesion has been created. The electrodes described herein may be coupled to any suitable device including an ECG with electrogram amplitudes being measured.

The electrodes 194, 196 may also be used to locate the end of a previously created lesion. The time between emission of the pacing stimulus to receipt of the cardiac impulse at the sensing electrode increases when a transmural ablation has been created between the electrodes 194, 196. When such an increase is detected, it is known that the previously created lesion is positioned between the electrodes 194, 196. The time between emission and receipt of the cardiac impulse may also be used in simple time of flight analysis to determine the location of a discontinuity in the ablation. For example, the electrodes 194, 196 are positioned at a discontinuity in an ablation when the time of flight is lowest.

A method of using the device is shown in FIGS. 32-35. The guide 200 is advanced to a desired location and the anchor 170 is actuated. The ablating device 20D is then advanced over the guide 200, the balloon 150 is inflated, and a first ablation 215 is performed. The balloon 150 is then deflated and the ablating device 20C is then moved to another location. The electrodes 191, 193 or 194, 196, or other suitable aligning device, is used to position and align the ablating device 20D and a second ablation 217 is then performed which is continuous with the first ablation 215. The device 20D is then moved again and a third ablation 219 is formed continuous with the second ablation 217.

Referring to FIGS. 36-38, another ablating device 210 is shown wherein the same or similar reference numbers refer to the same or similar structure. The ablating device 210 has an expandable structure 209, preferably a balloon 150A, movable along the ablating device 210 to selectively anchor and align the device 210. An advantage of the system of FIGS. 36-38 is that the structure 209 can be moved to various locations on the ablating device 210 for moving various ablating elements into contact with tissue to be ablated. The ablating device 210 also has the anchor 170, such as the balloon 150B, to anchor a part of the ablating device 210 and to move the ablating elements 27 into contact with the tissue to be ablated. The balloon 150B is coupled to a source of inflation fluid 211 via inflation lumen 223.

The expandable device 209 is mounted to a body 211 having a scalloped appearance to provide flexibility although any other suitable design may be used. The body 211 has a C-shaped cross-section which engages a flange 221 on the ablating device 210. The expandable device 209 is preferably the balloon 150A but may be a mechanically actuated device. For example, the expandable device 209 can be an extendable arm, a wire loop or an expandable mesh. The anchor 170 may be selectively expandable to guide, rotate, and move the ablating device 210 as necessary. The balloon 150A preferably has at least two separately inflatable chambers 212 and FIG. 38 shows the balloon 150A having three independently inflatable chambers 212. The chambers 212 are coupled to inflation lumens 219 which are coupled to a source of inflation fluid 213. The chambers 212 may be inflated as necessary to move and rotate the ablating device 210 and press the ablating element 27 against the tissue to be ablated. The expandable structure 209 is moved to various positions along the ablating device 210 to move various ablating elements 27 into contact with the tissue. The body 211 may also have pull wires 218 for further manipulation of the ablating device 210.

As mentioned above, penetrating the pericardial reflections carries inherent risks. However, the methods and devices of the invention may, of course, be used when penetrating the pericardial reflections. The ablating devices 20, 22, 20A, 22A may have a penetrating element 220 as shown in FIGS. 39-43 for penetrating the pericardial reflections. The penetrating element 220 is movable from a retracted position (FIG. 40) to an extended position (FIG. 41). The penetrating element 220 passes through the working channel 166 of the ablating device 20A. The penetrating element 220 is preferably positioned in the working channel 166 but may also be integrated into the ablating device 20A or may be a separate device altogether. The first and second ablating devices 20A, 22A are positioned on opposite sides of the pericardial reflection as shown in FIG. 40 using the emitter and sensor arrangement described above in connection with FIG. 22 although any other devices or techniques may be used. The penetrating element 220 is then used to penetrate the pericardial reflection and the two devices 20A, 22A are interlocked as shown in FIG. 41.

Referring to FIGS. 42 and 43, the ablating device 22A has a locking mechanism 224 which holds the penetrating element 220. The locking mechanism 224 has a stationary jaw 230 and a movable jaw 231. The movable jaw 231 is movable in the direction of arrow 223 for releasing the device 20A. The locking mechanism 224 is also positioned in the working channel 166 of the ablating device 22A but may be integral with the device 22A. The penetrating element 220 preferably has a conical tip 222 or other cutting element for piercing the pericardial reflection but may also be a laser, ultrasonic dissector, or electrosurgical device. The penetrating element 220 may also be a blade, needle or other structure for cutting or piercing the pericardial reflection. After ablating tissue, the locking mechanism 224 is released, the penetrating element 220 is retracted and the ablating devices 20A, 22A are removed. The ablating devices 20A, 22A may have any other interlocking configuration and the ablating device 22A may interlock with some other structure other than the penetrating element 220. Referring to FIG. 48, the ablating devices 20, 22 may interlock with one another in the manner described above. Referring to FIG. 44, the ablating device 20 may penetrate through one or more pericardial reflections and interlock with another part of the ablating device 20. Referring to FIG. 45, the ablating device 20 and the ablating device 22 may also interlock across the pericardial reflections using the penetrating element 220 or other suitable device.

Referring to FIGS. 46-49, another method of penetrating and advancing through the pericardial reflection is shown. The end of the ablating device 20A may be adhered to the pericardial reflection using suction through the working channel 166. The penetrating element 220 is then advanced through the working channel 166 while suction is maintained so that the piercing element is guided directly to the pericardial reflection. The penetrating element 220 is then used to penetrate the pericardial reflection as shown in FIG. 45. The ablating device 20A is then advanced through the pericardial reflection as shown in FIG. 46.

Referring to FIG. 14B, another anchor 170A for anchoring the device is shown. Any of the anchors described herein may be used with any of the devices described herein without departing from the scope of the invention. The anchor 170A is a relatively flat balloon having a thickness of about 1 cm and a width of about 0.3 cm when the balloon is inflated. Referring to FIG. 14C, yet another inflatable anchor 170B is shown which forms a hook-shaped element 171 which can engage a vessel such as the aorta, superior or inferior vena cava or any other vessel mentioned herein. Referring to FIG. 14D, still another anchor 170C is shown which has a mechanically expanding coiled section 173. As mentioned above, the anchors of the present invention are expanded to hold the devices at a particular location. For example, the anchors may be used to anchor a part of the device between blood vessels such as the superior vena cava and the aorta. When positioned between blood vessels or when engaging a vessel with the hook-shaped element of FIG. 14C, tension may be applied to the device to wrap the device around a vessel or vessels, such as the pulmonary veins, in the manner described above.

Referring to FIG. 49-54, another device 300 for ablating tissue, such as cardiac tissue, is shown. The device 300 may also be used in any manner described herein and may have the features and dimensions of other devices described herein without departing from the scope of the invention. The device 300 encircles the pulmonary veins and is particularly suited for conventional open chest surgery but may also be used in less and minimally invasive procedures. Although ablation of tissue around the pulmonary veins is described as a specific use of the device 300, the device 300 may be used on other parts of the heart and in other areas of the body.

The device 300 has a body 302 having a length of 5-12 inches, preferably about 10 inches, and a width of 0.2-0.7 inch preferably about 0.5 inch. The body 302 is preferably made of an polymeric material such as silicone or urethane and is formed by injection molding although any suitable material and method may be used to form the body 302. The body 302 has a number of cells 304 coupled together by integrally formed hinges 303 in the body 302. Of course, the cells 304 may be coupled together with mechanical connections rather than the integrally formed hinges 303 without departing from the scope of the invention. The device 300 preferably has 5-30 cells, more preferably 10-25 cells and most preferably about 16 cells although any number of cells 304 may be used depending upon the specific application. For example, the device 300 may be used to extend around a single vessel, such as the aorta, pulmonary vein, SVC or IVC in which case the device 300 preferably has 4-12 cells 304 and preferably about 8 cells 304.

The device 300 has a locking mechanism 306, preferably a buckle 308, which engages another part of the device 300 to form a closed loop 307. Referring to FIG. 49, the device 300 extends around the pulmonary veins with the locking mechanism 306 to form the closed loop 307 around the pulmonary veins. The buckle 308 forms a side-by-side (FIG. 50) or one on top of the other (FIG. 51) locking engagement with another part of the device 300. Although the buckle 308 is preferred, the locking mechanism 306 may have any other suitable structure for locking one part of the device 300 to another part of the device 300.

Referring now to FIGS. 49, 52, 53A and 54, the cells 304 have a suction well 310 for adhering the device to the tissue to be ablated. The suction well 310 may take any form and is preferably formed between an inner lip 312 and an outer lip 314. The suction well 310 has a suction port 316 coupled to a vacuum source 318 through a lumen 320. The vacuum source 318 is activated to cause the suction well 310 to hold the cell 304 against the tissue to be ablated. The lumen 320 is preferably formed by a separate tube 322 bonded to the body 302. The lumen 320 may, of course, be formed integral with the rest of the body 302. The upper surface of the cells 304 has three longitudinal recesses 324 in which the tubes 322, 326, 328 are positioned. The tubes 322, 326, 328 have slack between the cells 304 to permit the cells 304 to wrap around structures without significant resistance from the tubes 322, 326, 328.

The suction port 316 preferably has a cross-sectional size which is no more than 10% of the cross-sectional size of the lumen 320. In this manner, if suction is lost at one of the cells 304, suction can be maintained at the other cells 304 since the relatively small suction port 316 produces low flow. Of course, another part of the vacuum flow path 317 other than the suction port 316 may be sized small to reduce losses through cells 304 not adhered to the tissue.

An ablating element 311 is positioned within a closed wall 319 formed by the inner lip 312 so that the ablating element 311 is surrounded by the suction well 310. The ablating element 311 may be any ablating element mentioned herein and a preferred element is an RF electrode 330. The RF electrode 330 is coupled to an RF generator 332 which transmits RF energy to the electrode. The RF electrode 330 is preferably a stainless steel or gold plated copper electrode although any suitable electrode may be used. The ablating element 311 preferably has a width of 1-6 mm, preferably about 3 mm, and a length of 2-25 mm, preferably about 12 mm. When the ablating element 311 is the RF electrode, the ablating element 311 is preferably spaced apart from the target tissue, or from a bottom of the inner lip 312, by a distance of 0.5-3 mm and more preferably about 1.5 mm. The locking mechanism 306 preferably has at least one ablating element 311 to create a continuous lesion in tissue beneath the locking mechanism 306.

The ablating elements 311 are coupled to a control system 334 with wires 345. The control system 334 controls ablation in the manner described below. The RF generator 332 may form part of the control system 334 or may be separate from the control system 334. One or more temperature sensors 336, preferably thermocouples 338, are positioned within recesses in the inner and/or outer lips 312, 314 to measure temperature. The temperature sensors 336 are coupled to the control system 334 for use as described below. Wires 340 extending through the tube 326 couple the temperature sensors 336 to the control system 334.

Fluid is delivered to cool the tissue and/or conduct energy from the ablating element 311 to the tissue. Fluid is supplied from a source of fluid 342 to an inlet lumen 344 formed by tube 328. Fluid is withdrawn through the lumen 320 in the tube 322 so that the lumen 320 produces suction at the suction well 310 and withdraws fluid. As mentioned above, the lumens 344, 346 are preferably formed by the tubes 322, 328 but may be integrally formed with the rest of the body 302. The fluid is preferably a conductive solution, such as saline or hypertonic saline, which conducts RF energy from the electrode 330 to the tissue to be ablated.

Referring to FIGS. 53A and 54, fluid flows from the inlet lumen 344 into an inlet manifold 350 which distributes fluid along the length of the ablating element 311 as shown in the cross-sectional view of FIG. 54. Fluid then flows into a fluid chamber 348 formed between the ablating element 311, inner lip 312 and tissue. Fluid passes across the fluid chamber 348 and is received at a fluid outlet manifold 352. The fluid outlet manifold 352 is coupled to the lumen 320 so that the lumen 320 withdraws fluid and provides suction for the suction well 310 as mentioned above.

The fluid inlet and outlet 350, 352 are preferably positioned on opposite sides of the short axis of the fluid chamber 348, however, the fluid inlet and fluid outlet 350, 352 may be positioned anywhere within the fluid chamber 348 without departing from the scope of the invention. Fluid is preferably supplied at an average flow rate of at least 0.24 cc/sec, more preferably at least 0.50 cc/sec and most preferably at least 1.0 cc/sec to each cell 304 although lower or higher flows may be used. Fluid is preferably delivered to the inlet lumen 344 at a set pressure which results in the desired average flow rate through the cells 304. The fluid may be cooled, or even heated, by passing the fluid through a heat exchanger 354. The fluid is preferably delivered at a temperature of no more than 40.degree. C. and more preferably no more than 20.degree. C. to cool the tissue and/or ablating element 311. A fluid permeable, porous structure, such as gauze (not shown), may be positioned in the fluid chamber 348 to hold the fluid and prevent direct contact between the ablating element 311 and tissue.

Referring to FIG. 53B, the device 300E may also provide cooling to a backside 353 of the ablating element 311. Fluid from the inlet lumen 344 passes across the backside 353 of the ablating element 311 and is removed on the other side through the lumen 320. The embodiment of FIG. 53B may include any of the features and advantages of the embodiment of FIG. 35, for example, the fluid flow rate and temperature may be the same as described in relation to FIG. 53A. The inlet lumen 344 is also coupled to the suction well 310 via a conduit 355 for supplying fluid to the suction well 310. In this manner, the fluid may also be used to cool tissue adjacent to the ablating element 311. Fluid introduced into the suction well 310 is withdrawn through the lumen 320 in the manner described above. Although the fluid in the suction well 310 is exposed to the near surface NS of the tissue, the cooling fluid may also be contained within a closed circuit so that the near surface NS of the tissue is not in direct contact with the fluid. Furthermore, the fluid preferably cools tissue around the entire ablating element 311 but may also cool tissue only along one side of the device or only on the two lateral sides of the device without departing from the scope of the invention.

Referring to FIGS. 55 and 56, another device 300E is shown where the same or similar reference numbers refer to the same or similar structure. Use and dimensions of the device 300 are equally applicable for the device 300E. The device 300E has a lumen 356 contained within a cavity 358 in the body 302E. The lumen 356 carries the wires 340, 345 for the temperature sensors 336 and ablating elements 311. The lumen 356 is coupled to the control system 334 for control in the manner described below. The lumen 346 is a dedicated lumen for withdrawing fluid so that the fluid can be recycled as shown in FIG. 56. The system of FIG. 56 is described in greater detail below in connection with use of the devices 300, 300E. The lumen 356, wires 340, 345, ablating elements 311, and temperature sensors 336 form a strip 359 which is bonded to the rest of the body 302, preferably with an interlocking engagement.

A pair of wires 360, 362 is positioned across a gap 361 in suction path 363 (shown in dotted-line) to determine when the inner lip 312 is not adequately adhered to the tissue. When the inner lip 312 is not adequately adhered to the tissue, fluid leaks under the inner lip 312 and is drawn into the vacuum outlet 316. The fluid, which is preferably cooled hypertonic saline, conducts electricity across the gap 361 thereby indicating that the inner lip 312 may not be adequately sealed. The wires 360, 362 may be embedded in the body 302E or may travel through one or more of the lumens.

Referring to FIG. 57, another device 300F is shown which has two sets of lumens 364, 368 extending from both ends of the device 300F. The two sets of lumens 364, 368 perform the same functions as the lumens described above and all discussion of the device 300 is equally applicable here. An advantage of using two sets of lumens 364, 368 is that suction and/or fluid containment does not need to be maintained at all cells 304 at the same time. Connectors 370 at the buckle 308 are disconnected to wrap the device 300F around the pulmonary veins and are then reconnected to form the closed loop. Each set of lumens 364, 368 terminates near the middle of the device 300F at ends 372. Valves 374 are provided to selectively couple the lumens 362, 368 to the vacuum source 318 and/or fluid supply 342.

Referring to FIGS. 49 and 52-57 the control system 334 is coupled to the temperature sensors 336, ablating elements 311, fluid source 342 and vacuum source 318 for controlling the devices 300, 300E, 300F. The control system 334 may also be coupled to a pressure sensor 376 and/or a flow rate sensor 378 positioned along the inlet line of the vacuum source 318 (FIGS. 56 and 57). The pressure and/or flow rate sensors 376, 378 determine when the cells 304 are adequately secured to the tissue. If suction is not adequate, the pressure and/or flow rate will be higher than expected. Fluid flow indicators 380 can also be used to measure fluid flow into and out of the devices 300E, 300F to determine whether fluid is leaking from the cells 304 which also indicates a poor seal.

The cells 304 are preferably numbered and the control system 334 indicates whether each cell 304 is adequately adhered to the tissue. In this manner, the user may apply manual pressure to a particular cell 304 if an adequate seal is not present. The readout may be a digital readout 377 or lights 379 for each cell 304. The control system 334 also preferably has a temperature display 335 and a timer 337 for timing the duration of ablation.

The control system 334 preferably activates the ablating elements 311 in a predetermined manner. In one mode of operation, ablation is carried out at adjacent cells 304. Ablation may also be carried out at a number of pairs of adjacent cells such as the first and second cells 304 and the fifth and sixth cells 304. After ablation is carried out at these adjacent cells 304, another pair or pairs of adjacent cells are activated such as the third and fourth cells 304 and the seventh and eighth cells 304. The continuity of the ablation between the adjacent cells 304 may be confirmed in any suitable manner including those described herein. In another mode of operation, the control system 334 energizes every other cell, every third cell or a limited number of cells 304 such as no more than four. The control system 334 may also activate less than 50% and even less than 30% of the total ablation area at one time. For the device 300, a percentage of the total ablation area is essentially a percentage of the total number of ablation elements 311.

The ablation at each cell 304 may be controlled based on temperature measured at the temperature sensors 336. For example, the control system 334 may be configured to maintain a near surface NS temperature of 0-80.degree. C., more preferably 20-80.degree. C. and most preferably 40-80.degree. C. The temperature can be adjusted by changing the fluid flow rate and temperature and/or the power delivered to the ablating element 311. The control system 334 may also have a multiplexer 333 which delivers energy to only the cells 304 having a temperature below the threshold temperature. Alternatively, the multiplexer 333 may deliver energy to only the coldest cells 304 or only a number of cells 304 which register the coolest temperatures.

The control system 334 may also be configured to measure a temperature response of the tissue to be ablated. The temperature response of the tissue is measured to provide a tissue characterization which can be used to select the appropriate ablation technique. The ablation technique is primarily selected to produce a temperature of at least 50.degree. C. at the far surface FS of the tissue. When ablating cardiac tissue, for example, the control system 334 determines the ablation technique required to form a transmural lesion which requires a far surface FS temperature of 50-80.degree. C. and more preferably 50-60.degree. C. Measuring temperature at the far surface FS is somewhat difficult so the temperature of the near surface NS is used in conjunction with the methods and devices described herein. Of course, the temperature of the far surface FS may be measured to determine when the ablation is complete rather than using the temperature response described below.

The temperature response of the tissue is performed in the following manner. The tissue to be ablated is heated or cooled and the temperature response over time is measured with the temperature sensors 336. The temperature response over time at the near surface NS provides a rough indication of the thermal properties of the tissue to be ablated. The thermal properties of the tissue is affected by a number of variables including tissue thickness, amount of fat and muscle, blood flow through the region and blood flow and temperature at the far surface FS. These factors all play a role in the temperature response of the tissue. The tissue thickness, for example, affects the temperature response in the following manner. When a thin tissue layer is heated, the temperature at the near surface will generally increase more slowly than with a thick layer since the flow of blood at the far surface will draw heat away quicker with the thin tissue layer. The control system preferably measures the temperature response for at least two temperature sensors 336 for each ablating element with one of the temperature sensors being positioned laterally spaced to measure the temperature change at adjacent portions of the tissue.

After measuring the temperature change over time, the temperature response is then analyzed to determine the appropriate ablation technique. The analysis may be a comparison of the temperature response with temperature response curves of known tissue types. The temperature response curves may be developed empirically or may be calculated. The temperature response may also consider other variables input by the user including blood temperature and flow rate and the presence and amount of fat. When assessing the temperature response during heating with the ablating element, the amount of energy delivered to the tissue may also be used to characterize the tissue.

Using the results of the temperature response assessment, the control system 334 determines the appropriate ablation technique to produce the desired far surface FS temperature. In one mode of operation, the control system 334 determines the amount of time required to reach a desired far surface FS temperature when the near surface NS is maintained at a temperature of less than 60.degree. C. The control system 334 preferably maintains an adequate flowrate and temperature of fluid to maintain the desired near surface NS temperature. The control system 334 monitors the temperature of the near surface NS with temperature sensors 336. After the period of time has elapsed, the control system 334 automatically stops ablating. Alternatively, the ablation may take place until the near surface NS reaches a target temperature. The continuity of the ablation may then be checked in any manner described herein.

In use, the devices 300, 300E, 300F are wrapped around a structure, such as the pulmonary veins, with the locking mechanism 306 to form the closed loop 307. The vacuum source 318 is then activated to adhere the cells 304 to the epicardium. Manual pressure can be applied to cells 304 which are not sufficiently adhered to the tissue. The control system 334 then ablates tissue while delivering fluid to cool the tissue and conduct RF energy to the tissue. The continuity of ablation is then assessed by any suitable method including those described herein.

Referring to FIG. 58-63, still another device 400 is shown for ablating tissue wherein the same or similar reference numbers refer to the same or similar structure. The device 400 is particularly useful for ablating cardiac tissue but may be used for any other purpose without departing from various aspects of the invention. In a specific embodiment, the device 400 is used to ablate tissue around the pulmonary veins. The ablating device 400 has a number of cells 402 similar to the cells described above and description of the preferred characteristics above are equally applicable here. For example, the cells 402 may have the preferred dimensions and features of the cells 304 described above. The ablating device 400 has an ablating element 404 which is preferably an ultrasonic transducer 406 although various features of the invention may be practiced with any other type of ablating element 464 (FIG. 68).

The device 400 preferably delivers ultrasound which is focused in at least one dimension. In particular, the device 400 preferably delivers focused ultrasound having a focal length of about 2 to 20 mm, more preferably about 2 to 12 mm and most preferably about 8 mm. Stated another way, a focal axis FA is spaced apart from a bottom or contact surface 405 of the device within the stated ranges. The focused ultrasound also forms an angle of 10 to 170 degrees, more preferably 30 to 90 degrees and most preferably about 60 degrees as defined relative to the focal axis A. The ultrasonic transducer 406 is preferably a piezoelectric element 408. The transducer 406 is mounted within a housing 410. The housing 410 has an enclosure 412 and a top 414 which fits over the enclosure 412. The enclosure 412 has curved lips 416 on both sides of the enclosure 412 which generally conform to the curvature of the transducer 406. The transducer 406 is curved to focus the ultrasound energy for the reasons discussed below. The transducer 406 has a length of about 0.43 inch, a width of about 0.35 inch and a thickness of about 0.017 inch. The transducer 406 has a radius of curvature R (FIG. 62) consistent with the preferred focal lengths described above. The transducer 406 forms an angle A with the focus F within the preferred angle ranges described above.

A layer 418, which is preferably aluminum but may be any other suitable material, is bonded or otherwise acoustically coupled to a concave side 423 of the transducer 406. The layer 418 has a length of about 0.51 inch, a width of about 0.43 inch and a thickness of about 0.012 inch. The layer 418 preferably has the same radius of curvature as the transducer 406 so that the layer 418 mates with the transducer 406. The layer 418 is attached to the curved lips 416 of the enclosure 412 with an epoxy.

An advantage of using focused ultrasonic energy is that the energy can be concentrated within the tissue. Another advantage of using focused ultrasound is that the energy diverges after reaching the focus thereby reducing the possibility of damaging tissue beyond the target tissue as compared to collimated ultrasonic energy. When ablating epicardial tissue with collimated ultrasound, the collimated ultrasound energy not absorbed by the target tissue travels through the heart chamber and remains concentrated on a relatively small area when it reaches the endocardial surface on the other side of the chamber. The present invention reduces the likelihood of damage to other structures since the ultrasonic energy diverges beyond the focus and is spread over a larger area.

Although the focused ultrasonic energy is preferably produced with the curved transducer 406 and the layer 418, the focused ultrasonic energy may be produced with any suitable structure. For example, acoustic lensing may be used to provide focused ultrasound. The acoustic lens can be used with a flat piezoelectric element and matching layer. Furthermore, although the ultrasound energy is preferably emitted directly toward the tissue the ultrasound energy may also be reflected off a surface and directed toward the tissue without departing from the scope of the invention. The energy may also be produced by a number of small transducers which are oriented to focus or concentrate ultrasonic energy, such as at least 90% of the energy, within the preferred angle ranges and radius of curvature described herein when viewed along a longitudinal axis 419 or along the focal axis FA. For example, a multielement acoustic phased array may be used to provide an acoustic beam-steering capability from one or more cells. One skilled in the art can also appreciate the use of multiple matching layers, focusing acoustic lenses and non-focusing acoustic windows and the like. Thus, the focused energy may be produced in a number of different ways, including other ways not mentioned here, without departing from the scope of the invention.

A distributing element 420 is attached to the transducer 406 at two locations to distribute energy that drives the transducer 406. The element 420 is preferably a piece of copper ribbon 0.020 inch wide and 0.0005 inch thick soldered to the transducer 406 at two locations. A coaxial cable 422 delivers power to the transducer 406 from a source of power 421 and also provides a ground path. The coaxial cable 422 has a power lead 424 coupled to the distributing element 420 to power the transducer 406. A braided portion 426 of the cable 422 serves as a ground. The braided portion 426 is soldered to a tube 428 and/or the top 414. The ground path leads from the transducer 406 to the layer 418 and then to the housing 410 at the curved lips 416. The ground path then passes to the top 414 and finally to the braided portion 426 either directly or via the tube 428. The tube 428 and top 414 are preferably made of brass and the enclosure 412 is preferably made of aluminum although any other suitable materials may be used. Polyimide tape 430 is adhered to the inside of the enclosure 412 and on the transducer 406 to electrically separate the two structures.

The transducer 406 may be cooled during operation although cooling may not be required. A cooling inlet 432 having an inlet lumen 440 extends through the top 414 and is coupled to a source of cooling medium 434. The cooling medium, which is preferably forced air, passes into a chamber 436 so that the cooling medium is in direct contact with the transducer 406. A cooling outlet 438 having an outlet lumen 442 removes the cooling medium from the chamber 436. Although the lumens 440, 442 are preferably separate and independent from the housing 420, the lumens 440, 442 may also be integrated into the housing 420 without departing from the scope of the invention.

The cells 402 may also be adhered or acoustically coupled to the tissue with suction in the manner described above although various features of the invention may be practiced without using suction. The housing 410 is mounted within an opening 446 in a suction body 448. The body 448 has a port 449 coupled to a lumen 452 leading to the vacuum source 318. The lumen 452 is coupled to the outlet lumen 442 with tubing 443 so that the outlet lumen 442 provides suction and withdraws the cooling medium (FIG. 59). Of course, the lumen 452 may also be completely independent of the outlet lumen 442. FIG. 58 shows separate cooling outlet and vacuum lumens. The port 450 leads to recesses 454 on two sides of the transducer 406. The recesses 454 also may be formed by individual suction pods, a linear segment, or any other suitable structure without departing from the scope of the invention. A channel 456 extends from one side of the enclosure 412 to provide communication between the two recesses 454. The channel 456 prevents only one recess 454 from being adhered to the tissue. The body 448 is preferably made of polycarbonate but may be made of any other suitable material.

The ablating device 400 may also be used with a substance, such as a gel or saline, applied to the target tissue to eliminate air gaps between the transducer 406 and target tissue. Air gaps between the transducer 406 and target tissue impede delivery of ultrasonic energy to the tissue. When using suction as described below, use of the substance may be unnecessary since the transducer 406 assembly can be forced into intimate contact with the target tissue with the suction force.

The ablating device 400 may also have a membrane 460 (FIG. 64) filled with the substance 458 or a solid element 459 (FIG. 65) which transmits the ultrasonic energy to the tissue. An advantage of the membrane 460 is that the membrane 460 may be made flexible and compliant to conform to the tissue. Another advantage of the membrane 460 is that the distance between the transducer 406 and the tissue may be varied. When ablating thick tissue, the membrane 460 can be deflated so that the transducer 406 is close to the tissue (FIG. 64). When ablating thin tissue, the membrane 460 is inflated so that the transducer 406 is further from the tissue (FIG. 66). Adjacent cells preferably maintain contact with the tissue to maintain the orientation of the device. The membrane 460 may also be inflated and deflated during or between activations of the transducer 406 to move the focus relative to the tissue. For example, the membrane 460 may be inflated and deflated to move the focus relative to the tissue and, in particular, to different depths. The membrane 460 is adhered to the device around the bottom of the enclosure 412. The membrane 460 is preferably compliant and may be made of any suitable material such as silicone or urethane. The membrane 460 may be pre-filled with the substance or the substance may be added later through another lumen (not shown).

Referring to FIG. 67, the membrane 460 may also take a shape which tilts the transducer 406. The transducer 406 is preferably tilted to direct the ultrasound energy to tissue positioned beneath gaps between adjacent transducers 406 as will be explained in greater detail below. A flexible flange 461 deflects to permit tilting of the device. The transducer 406 may be angled, pivoted or tilted in any other suitable manner. For example, the transducer 406 may have a mechanical pivot which moves the transducer 406 or a movable foot on the bottom of the device 400 which is advanced and retracted to tilt the transducer 406.

Referring to FIG. 68, another device 462 for ablating tissue is shown wherein the same or similar reference numbers refers to the same or similar structure. The device 462 has the ablating element 404 which is preferably an ultrasonic transducer 463. The transducer 463 is designed to deliver ultrasonic energy to tissue beneath the transducer 463 and to tissue beneath the gaps between adjacent cells 402. In this manner, the device may be operated without moving or tilting the transducers 463 to create a continuous lesion beneath the device. The transducer 463 is a flat transducer 463 with a layer 464 attached thereto. The layer has a flat bottom portion 466 and angled sides 468 which direct energy at tissue lying beneath the gaps between adjacent transducers 463. The device 462 has a membrane 470 adhered over the bottom of the cell 402. The membrane 460 is filled with a substance 472, such as a gel or saline, which transmits the ultrasonic energy to the tissue. The device 462 may be operated in any mode or method described herein.

Referring to FIGS. 69-70, another transducer 474 is shown which may be used with any of the devices described herein and is particularly useful with the devices of FIGS. 59-68 and all uses and features of the devices described herein are incorporated here. The transducer 474 preferably provides focused ultrasound relative to a focal axis FA within focal lengths and/or angle ranges described above. The transducer 474 also provides diverging ultrasound energy when viewed along an axis transverse to the focal axis (FIG. 70). The ultrasound diverges to form an angle A2 of about 10 to 120 degrees and preferably about 45 degrees. The focused and diverging ultrasound is preferably formed with the saddle-shaped transducer 474 with a similarly shaped layer 476 attached or otherwise acoustically coupled thereto. Of course, the focused and diverging ultrasound may be produced in any other suitable manner including those described herein. An advantage of the diverging nature of the ultrasound energy is that tissue lying beneath gaps between cells can be ablated with the ablating elements while still providing a relatively focused energy. The term focal axis FA, as defined herein, is intended to include both linear and non-linear shapes. For example, the focal axis FA of the transducer of FIGS. 69 and 70 is curved.

Referring to FIGS. 71-73, still another ablating device 478 is shown wherein the same or similar reference numbers refer to the same or similar structure. The ablating device 478 has a first ablating element 480, a second ablating element 482 and a third ablating element 484 which differ. Although only three different ablating elements are shown, the device 478 could include any number of ablating elements. The ablating elements differ to provide different ablating characteristics. For example, the ablating elements may produce focused ultrasound with the first ablating element having a different focal length than the second or third ablating elements. Such a configuration permits the user to select the appropriate ablating element for the particular tissue structure. The ablating elements 480, 482 and 434 may also be designed to operate at different frequencies and/or powers.

The ablating elements are movable within a lumen 486 in a body 488. The body 488 forms two suction channels 490 to adhere the device to the target tissue. The body 488 preferably forms a closed loop but may be shaped in any other manner. Each of the ablating elements has an element 492 which transmits the ultrasound energy to the target tissue. The ablating elements may also have the membrane (see FIG. 64) or may be used without the element or membrane (see FIG. 60). Lumens 491 for supply of energy, suction and inlet and outlet for the cooling medium are provided. The lumens 491 extend through a manipulator 493. The manipulator 493 forms a seal with the body 488 to adhere the body 488 to the tissue with a suction.

An advantage of using ultrasound for ablation is that the transducer may also be used to measure temperature. Measuring temperature is particularly helpful in operating the transducer for feedback control of the ablating element in any manner described above. Of course, the thermocouples described above or any other suitable methods or devices for measuring temperature may be used.

Another advantage of using the transducer is that the transducer can be used to determine whether the transducer itself is in good contact with the tissue to be ablated. Any air gap between the transducer and the near surface NS can dramatically affect the ability to deliver the ultrasonic energy in a controlled manner. The adequacy of contact is determined by measuring the electrical impedance which is generally large when an air gap exists between the transducer and tissue. Monitoring suction as described above is another method of assessing contact between the device and tissue.

Yet another advantage of using the transducer is that the transducer can provide flow velocity data using conventional doppler techniques. The doppler flow techniques can be used to characterize the amount of cooling at the far surface FS which can be used to select the appropriate tissue ablation technique.

Still another advantage of the transducer is that the transducer can provide the thickness of one or more layers of tissue using known pulse-echo or a-line techniques. For example, the transducer may be operated to provide total tissue thickness or the thickness of fat and muscle or other layers. The thickness of fat, muscle, and total thickness may be used when characterizing the tissue to determine the appropriate ablation technique. For example, the ablating element may be operated in response to the tissue thickness measurement with or without one or more additional measurements. A single transducer may be used to emit ultrasonic energy and receive reflected energy or one transducer may emit and a different transducer can receive the reflected ultrasound energy.

The transducer may also be used to determine the distance to tissue beyond the target tissue such as endocardial tissue on the opposite side of a cardiac chamber. Such measurements can be useful in selecting the appropriate transducer. For example, if the tissue structure beyond the target tissue is relatively far away, a longer focal length can be used since the ultrasound energy will be spread over a larger area. On the other hand, if the tissue structure is near the target tissue, shorter focal lengths may be preferred to avoid damaging the tissue structure beyond the target tissue.

These above-described aspects of the ablating element may be combined with any of the other features and advantages of the invention. For example, the transducer 406 may be used for temperature feedback control of the control system 334 in any manner described herein and the flow velocity measurements may be used to characterize the amount of blood cooling at the far surface FS.

A method of ablating tissue is now described. The method is described in connection with the ablating device 400 described above, however, the method may be practiced with any other suitable structure or device. The ablating device 400 is positioned against tissue to be ablated and suction is initiated to hold the cells 402 to the tissue to be ablated. The ablating device 400 may use any of the methods and devices described above, such as temperature feedback control or methods of checking the adequacy of contact, which are incorporated here. As will be explained below, the transducer 406 itself may be used to determine the adequacy of the contact between the device and the tissue. In particular, the transducer 406 may also be used to determine whether any air gaps exist between the transducer 406 and the tissue. After it has been determined that the cells 402 are adequately adhered to the tissue, one or more of the cells 402 are activated to begin ablating tissue.

In another aspect of the invention, the device is operated during two different time periods while varying at least one characteristic of the device such as the frequency, power, position of the focus relative to the tissue and/or ablating time. For example, the ablating device 400 may be operated at varying frequencies over time to ablate tissue in a controlled manner. Specifically, the ablating device is preferably operated to create a transmural lesion by controlling the delivery of energy to the tissue. Although it is preferred to vary the frequency when ablating the tissue, the device may, of course, be operated at a single frequency without departing from various other aspects of the invention In a first treatment method of the present invention, the transducer 406 is activated at a frequency of 2-7 MHz, preferably about 3.5 MHz, and a power of 80-140 watts, preferably about 110 watts, in short bursts. For example, the transducer 406 may be activated for 0.01-1.0 second and preferably about 0.4 second. The transducer 406 is inactive for about 2-90 seconds, more preferably 5-80 seconds, and most preferably about 45 seconds between activations. In this manner, a controlled amount of accumulated energy can be delivered to the tissue in short bursts to heat tissue at and near the focus and minimizes the impact of blood cooling at the far surface FS. Ablation at this frequency may continue until a controlled amount of energy is delivered such as about 0.5-3 kilojoules. Treatment at this frequency in relatively short bursts produces localized heating at the focus. At the first frequency, energy is not absorbed as quickly in tissue as it is at higher frequencies so that heating at the focus is not significantly affected by absorption of ultrasound energy in tissue before reaching the focus.

Following treatment at the first frequency, the transducer 406 is operated for longer periods of time, preferably about 1-4 seconds and more preferably about 2 seconds, to ablate tissue between the focus and the transducer 406. The frequency during this treatment is also 2-14 MHz, more preferably 3-7 MHz and preferably about 6 MHz. The transducer 406 is operated for 0.7-4 seconds at a power of 20-60 watts, preferably about 40 watts. The transducer 406 is inactive for at least 3 seconds, more preferably at least 5 seconds and most preferably about 10 seconds between each activation. In this manner, a controlled amount of energy can be delivered to heat tissue between the focus and the transducer. The treatment at this frequency may continue until a controlled amount of total energy is delivered such as about 750 joules.

As a final treatment, the ultrasonic transducer is activated at a higher frequency to heat and ablate the near surface NS. The transducer is preferably operated at a frequency of at least 6 MHz and more preferably at least 10 MHz and most preferably about 16 MHz. The transducer 406 is operated at lower power than the treatment methods above since the ultrasonic energy is rapidly absorbed by the tissue at these frequencies so that the near surface NS is heated quickly. In a preferred method, the transducer is operated at 2-10 watts and more preferably about 5 watts. The transducer 406 is preferably operated until the near surface NS temperature reaches 70-85 degrees C.

Each of the treatments described above may be used by itself or in combination with other treatments. Furthermore, the combination of transducer size, power, frequency, activation time, and focal length may all be varied to produce the desired delivery of ultrasound energy to the tissue. As such, it is understood that the preferred embodiment may be adjusted by simply adjusting one or more of the characteristics and, thus, these parameters may be changed without departing from various aspects of the invention. The treatment sequence described above generally deliver energy closer to the near surface NS during the second treatment and even closer to the near surface NS for the third treatment.

The focus of the ultrasound energy may also be moved relative to the tissue to deliver energy to different depths in the tissue. When using the devices of FIGS. 66 and 67, for example, the device can be moved closer to and farther away from the target tissue with the membrane 460 conforming to the required shape to fill the gap between the transducer 406 and the tissue. The membrane is preferably inflated and deflated to move the focus, however, the device may also be moved with any other suitable mechanism such as the threaded foot described above. The focus may be moved while the ablating element is activated or may be moved between activations of the ablating element. Moving the focus of the ultrasound energy may be sufficient to create a transmural lesion without changing frequencies or may be used together with a change in frequencies as described above. The focus may be moved in any other manner such as with a phased array or variable acoustic lensing.

Referring again to FIG. 60, after the ablating elements have been activated to ablate tissue it may be necessary to ablate tissue in gaps between ablations from each of the cells. In one method, the entire device is shifted so that each of the ablating elements is positioned to ablate tissue beneath one of the gaps. Thus, after ablating tissue with all of the cells, the device is shifted and all of the cells are activated again to create a continuous lesion. Another method to ablate tissue beneath the gaps is to tilt the cells to ablate tissue beneath the gaps. In this manner, the device does not need to be moved. When using the device of FIG. 67, for example, the membrane is inflated to tilt the transducer which directs the ultrasound energy toward tissue beneath gaps between transducers.

The control system 334 may be designed to automatically ablate in any manner described herein. For example, the control system can change the frequency, power, focal length and/or operating time to provide the desired ablating technique. The change in frequency and power may be completely automatic or may require some user input such as visual indications of fat and/or tissue thickness. For example, the control system 334 may be designed to automatically sequence through two or more different ablating techniques such as those described above. Other techniques, of course, may be used depending on the tissue characteristics and the type and characteristics of the one or more ultrasound transducers 406. The control system 334 may also utilize feedback, such as temperature-based feedback or electrical impedance, to actively control the ablations. Furthermore, although various methods have been described, the corresponding functionality of the control system is provided. Thus, all methods of the present invention provide corresponding devices and systems as controlled by the control system.

In still another aspect of the present invention, a cover 500 is provided in which an ablating device 502 is positioned during initial positioning of the device as shown in FIG. 74. The cover 500 may extend over only the bottom or contact surface of the ablating device 502 or may be a sleeve 501 which surrounds the device 502. The ablating device 502 may be any of the ablating devices, elements or systems described herein or any other suitable system and all aspects of the ablating devices described herein are incorporated here specifically for the ablating device 502. The cover 500 has a cavity 503 which contains a flowable material 504. The flowable material 504 provides an interface between the ablating device 502 and the tissue to be ablated. The ablating device 502 is loaded into the cover 500 to help reduce or eliminate air bubbles or gaps contained in the flowable material 504. Air bubbles or air gaps can reduce the performance of various energy sources such as RF and ultrasound.

The cover 500 is positioned at or near the desired ablating location and the cover 500 is then pulled, retracted or otherwise moved to expose the ablating device 502. When the cover 500 is moved to expose the ablating device 502, the flowable material 504 conforms to the shape of the target tissue to provide an interface of the flowable material 504 between the ablating device 502 and the target tissue. The cover 500 is moved by simply pulling the sleeve over the end of the ablating device 502 while maintaining the ablating device in substantially the desired ablating position. Alternatively, the ablating device 502 may be moved out of the cover 500, however, removal of the cover 500 is preferred to prevent loss of the flowable material 504 as the ablating device 502 is moved along the target tissue. The flowable material 504 may be any suitable material depending upon the ablating energy being used. When ultrasound energy is used, the flowable material is preferably PEG (polyethyleneglycol) or glycerine. The flowable material also preferably has a relatively high boiling point such as at least 100 degrees C. and a vapor pressure lower than that of water.

In still another aspect of the present invention, the ablating device 502 may also have a tip 510 which provides a flexible, atraumatic distal end as shown in FIG. 74. The flexible tip 510 facilitates advancement of the device 502 through the space between the epicardium and pericardium without damaging the heart or pericardium. The tip 510 may be removable so that the tip 510 does not interfere with the ablating process and can make it easier to form a closed loop as is shown in various embodiments contained herein. It can be appreciated that the tip 510 may be used with any of the ablating devices, systems or methods described herein without departing from this aspect of the invention. The tip 510 preferably has a length of at least two inches and more preferably at least four inches from the distal end 511. The tip 510 is preferably free of any ablating elements.

In another aspect of the present invention, another system and method for ablating tissue is shown in FIGS. 75 and 76. The system 512 provides a liquid environment around the heart. The liquid environment may help in energy transfer when using certain energy types, such as RF or ultrasound, and/or may serve to simply eliminate air bubbles or gaps which can hinder energy transfer. The liquid environment also helps in controlling the temperature since the temperature of the liquid can be regulated. For example, the liquid can be circulated through a heat exchanger 514 which heats or cools the liquid as desired. In one aspect of the invention, the liquid is cooled to remove heat generated by the ablating device 502. The temperature may be controlled in any manner described herein and such methods are specifically incorporated here.

The system 512 includes a liquid delivery element 516, such as a tube 518, connected to a liquid source 520, preferably sterile saline. Of course, the liquid must also be delivered and/or withdrawn with the ablating device 502. Liquid is delivered as necessary with conventional valves 522 and clamps 524 controlling the flow of liquid. The ablating device 502 is submerged within the liquid environment and may be any device described herein or other suitable device. The liquid delivery element 516 may form a fluid tight seal with the pericardium or the patient may be positioned so that the liquid environment can be created by penetrating the pericardium at an elevated position which does not require a hemostatic seal. The system 512 may be used in an open chest procedure with a rib retractor 515 as shown in FIG. 76. The pericardium is snared, sutured or otherwise anchored or suspended as is known in the art. The system 512 may also be used in a less or minimally invasive manner as shown in FIG. 75 wherein the chest is accessed via a subxyphoid approach. The delivery element 516 has two lumens with one of the lumens 517 being an outlet lumen coupled to openings 519.

In another aspect of the invention, any of the ablating devices described herein may have a convex contact surface 520 as shown in FIGS. 73 and 74. The convex contact surface 520 helps to squeeze or eliminate air bubbles or gaps from the area between the device and the target tissue. Air bubbles or gaps can inhibit energy transfer and, in particular, can reduce the efficiency of ultrasound and RF energy transfer. The convex surface 520 may form part of the ablating element itself or may be a separate element that is adhered, mounted or otherwise coupled to the ablating device as described above. Of course, the convex contact surface 520 may be used with any of the ablating devices described herein and is shown specifically in FIGS. 73 and 74. The convex contact surface 520 may be made of any suitable material such as polyurethane.

Referring to FIGS. 77 and 78, another ablating device 522 is shown which is similar to the device of FIG. 64 wherein all aspects of the device of FIG. 64 are incorporated here. The ablating device 522 has the membrane 460 which is spaced apart from the ablating element to form a fluid cavity 524 therebetween. The fluid cavity 524 contains a fluid 526 which can serve any one or more of the following functions. The fluid 526, of course, transmits energy from the ablating element. The membrane 460 also conforms to the shape of the target tissue. The fluid 526 may be delivered from the source of cooling medium 434 having a suitable heat exchanger as discussed above. The temperature of the fluid 526 may be controlled in any manner described herein and all such descriptions are incorporated specifically here for all purposes. For example, temperature control of the fluid provides the ability to control the near surface temperature of the tissue in any manner described herein.

Referring to FIG. 77, each fluid cavity 524 may extend over a single ablating element with each of the fluid cavities 524 being coupled to a common inlet lumen 530 and outlet lumen 531. Alternatively, the membrane 460 may extend over a number of ablating elements or along the entire device as shown in FIG. 78. The fluid 526 is circulated through the fluid cavity 524 from an inlet lumen 525 attached to one end and an outlet lumen 527 attached to the other end of the device. The fluid 526 is circulated through the fluid cavity 524 using the source of cooling medium 434. The membrane 460 may also have openings 462 (FIG. 77) therein or may be permeable so that some of the fluid 526 leaks through the membrane 460. The fluid 526 may help conduct energy or may simply reduce or eliminate air gaps. The membrane 460 may also form the convex contact surface 520 naturally or when fluid pressure is applied. The fluid 526 may also be pulsed to provide intermittent weeping or leaking of the fluid through the membrane 460. The pulsed fluid flow may also be used to deform the membrane by partially inflating/deflating the membrane which may help to sweep away bubbles or provide a flushing action for the fluid.

Referring now to FIG. 79, a flexible skirt 536 may be provided around the ablating element. The flexible skirt 536 may be used to contain the fluid 526 which is supplied in any suitable manner such as those described herein. Referring to FIG. 80, the flexible skirt may be used in connection with the convex contact surface 520. The fluid 526, or other flowable material, is introduced through an inlet 540 and travels down lumen 542 to the contact surface 520. The skirt 536 helps to contain the fluid 526 to inhibit the fluid 526 from flowing freely outward.

Finally, although the present methods have been described in connection with creating a continuous lesion around the pulmonary veins, it is understood that the methods are equally applicable for only ablating partially around the pulmonary veins or along only a segment. Furthermore, other lesions may be beneficial in treating electrophysiological conditions and the devices and methods described herein may be useful in creating such other lesions. Thus, the present invention should not be construed as being limited to creating lesions completely around the pulmonary veins.

While the above is a complete description of the preferred embodiments of the invention, various alternatives, substitutions and modifications may be made without departing from the scope thereof, which is defined by the following claims. For example, any of the ablating devices described herein may have the anchor, fins, lateral balloons, sensors, and/or electrodes without departing from the scope of the invention.

What is claimed is:

1. A system for ablating tissue with ultrasound energy, comprising
    a plurality of ultrasound ablating elements, each ablating element being adapted to emit focused ultrasound energy; and
    a control system coupled to the ablating elements, the control system programmed to control activation of the ablating elements and to automatically change a frequency of the ablating elements when ablating the same tissue structure,
    wherein the control system is programmed to activate each ablating element at a first frequency for a first time period and to activate each ablating element at a second frequency, which is a predetermined frequency different from the first frequency, for a second time period.

2. The system of claim 1, wherein the control system is adapted to move a focus of the ultrasound energy relative to a tissue structure being ablated.

3. The system of claim 2, wherein the control system is adapted to move the focus closer to a near surface of the tissue structure being ablated.

4. The system of claim 1, wherein the control system includes means for assessing the adequacy of contact between the ablating elements and the tissue structure being ablated.

5. The system of claim 4, wherein the assessing means is carried out by measuring an electrical impedance.

6. The system of claim 1, wherein the control system includes a sensor adapted to assess the adequacy of contact between the ablating elements and a tissue structure being ablated.

7. The system of claim 6, wherein the sensor is adapted to measure an electrical impedance.

8. The system of claim 1, wherein the control system is programmed to activate the plurality of ablating elements in a predetermined sequence.

9. The system of claim 1, wherein the control system is adapted to deliver 90% of the focused ultrasound energy within a focus area defined by a focal length of about 2-20 mm and an angle of about 10 to 170 degrees when viewed along a focal axis.

10. The system of claim 1, wherein at least one of the plurality of ablating elements has a concave ablating surface.

11. The system of claim 1, wherein the focused ultrasound has a focal length of about 2-20 mm.

12. The system of claim 1, wherein the first frequency is less than the second frequency.

13. The system of claim 1, wherein the first frequency is about 2-7 MHz and the second frequency is about 2-14 MHz.

14. The system of claim 1, wherein the first time period is less than the second time period.

15. The system of claim 1, wherein the first time period is less than about one second.

16. The system of claim 1, wherein the control system is programmed to activate each ablating element at the first frequency for a number of discrete time periods.

17. The system of claim 1, wherein the control system is programmed to activate each ablating element at a third frequency, which is different from the first and second frequencies, for a third time period.

18. The system of claim 17, wherein the third frequency is about 6-16 MHz.

19. The system of claim 1, wherein the control system is programmed to measure at least one of a tissue thickness, a fat thickness, a muscle thickness and a blood flow velocity.

20. The system of claim 1, wherein each ablating element further comprises a membrane, and wherein the membrane and the ablating element define a fluid cavity therebetween.

21. The system of claim 20, wherein the membrane is inflatable.

22. The system of claim 20, wherein the membrane is adapted to tilt the ablating element relative to a tissue surface.

* * * * *